US008618054B2

(12) United States Patent  (10) Patent No.: US 8,618,054 B2
Chemtob et al.  (45) Date of Patent: Dec. 31, 2013

(54) INTERLEUKIN-1 RECEPTOR ANTAGONISTS, COMPOSITIONS, AND METHODS OF TREATMENT

(75) Inventors: Sylvain Chemtob, Côte St-Luc (CA); Christiane Quiniou, Montréal (CA); William D. Lubell, Montréal (CA); Martin Beauchamp, Montréal (CA); Karl A. Hansford, Montréal (CA)

(73) Assignees: Valorisation-Rechereche Société en Commandite, Montreal (CA); Valorisation HSJ, Société en Commandite, Montreal (CA)

(*) Notice: Subject to any disclaimer, the term of this patent is extended or adjusted under 35 U.S.C. 154(b) by 147 days.

(21) Appl. No.: 11/122,989

(22) Filed: May 5, 2005

(65) Prior Publication Data

US 2006/0094663 A1  May 4, 2006

Related U.S. Application Data

(60) Provisional application No. 60/714,512, filed on May 5, 2004.

(51) Int. Cl.
*A61K 38/00* (2006.01)
*A61P 29/00* (2006.01)

(52) U.S. Cl.
USPC ........................................................ 514/12.2

(58) Field of Classification Search
None
See application file for complete search history.

(56) References Cited

U.S. PATENT DOCUMENTS

| | | | |
|---|---|---|---|
| 4,244,946 A | 1/1981 | Rivier et al. | |
| 4,305,872 A | 12/1981 | Johnston et al. | |
| 4,316,891 A | 2/1982 | Guillemin et al. | |
| 5,126,249 A | 6/1992 | Becker et al. | |
| 5,223,409 A | 6/1993 | Ladner et al. | |
| 5,639,725 A | 6/1997 | O'Reilly et al. | |
| 5,712,380 A | 1/1998 | Kendall et al. | |
| 5,854,221 A | 12/1998 | Cao et al. | |
| 5,952,199 A | 9/1999 | Davis-Smyth et al. | |
| 5,955,575 A | 9/1999 | Peri et al. | |
| 5,981,852 A * | 11/1999 | Van Assche et al. | 800/317.4 |
| 6,280,955 B1 * | 8/2001 | Cao | 435/7.1 |
| 6,300,312 B1 | 10/2001 | Chemtob et al. | |
| 6,777,388 B1 * | 8/2004 | Grasso et al. | 514/16 |
| 6,864,229 B2 | 3/2005 | Kuliopulos et al. | |
| 6,984,719 B1 | 1/2006 | Chemtob et al. | |
| 7,432,341 B2 | 10/2008 | Chemtob et al. | |
| 7,442,763 B2 | 10/2008 | Peri et al. | |
| 7,521,530 B2 | 4/2009 | Peri et al. | |
| 2004/0235749 A1 | 11/2004 | Chemtob et al. | |
| 2006/0166274 A1 | 7/2006 | Kuliopulos et al. | |
| 2007/0037210 A1 * | 2/2007 | Chemtob et al. | 435/7.1 |

FOREIGN PATENT DOCUMENTS

| | | |
|---|---|---|
| CA | 2235695 | 5/1997 |
| CA | 2372164 | 9/2000 |
| EP | 495049 | 4/1997 |
| WO | WO 93/14781 | 8/1993 |
| WO | WO 96/23067 | 8/1996 |
| WO | WO-00/78341 | 12/2000 |
| WO | WO 01/92340 | 12/2001 |
| WO | WO 03/014309 | 2/2003 |
| WO | WO 03/022991 * | 3/2003 |
| WO | WO 03/016571 * | 12/2003 |
| WO | WO 2005/105830 | 11/2005 |
| WO | WO 2007/004060 | 1/2007 |

OTHER PUBLICATIONS

Weaver Al, "The impact of new biologicals in the treatment of rheumatoid arthritis," Rheumatology (Oxford). Jun. 2004;43 Suppl 3:11117-11123.*
U.S. Appl. No. 11/919,941, filed Nov. 5, 2007, Chemtob et al.
Amit et al., "A membrane-fixed, truncated isoform of the human growth hormone receptor," J. Clin. Endocrinol. Metab. 82(11):3813-3817 (1997).
Baker et al., "Cell Proliferation Kinetics of Normal and Tumour Tissue in Vitro: Quiescent Reproductive Cells and the Cycling Reproductive Fraction," *Cell Prolif.* 28(1):1-15 (1995).
Binetruy-Tournaire et al., "Identification of a Peptide Blocking Vascular Endothelial Growth Factor (VEGF)—Mediated Angiogenesis," *EMBO J.* 19:1525-1533 (2000).
Brady and Dodson, "Reflections on a Peptide," *Nature* 368:692-693 (1994).
Carell et al., "A Novel Procedure for the Synthesis of Libraries Containing Small Organic Molecules," *Angew Chem Int Ed Engl* 33(20):2059-2061 (1994).
Cheviron et al., "The Antiproliferative Activity of the Tetrapeptide Acetyl-N-SerAspLysPro, an Inhibitor of Haematopoietic Stem Cell Proliferation, is Not Mediated by a Thymosin β4-like Effect on Actin Assembly," *Cell Prolif.* 29(8):437-446 (1996).
Cho et al., "An Unnatural Biopolymer, "*Science* 261:1303-1305 (1993).
Coller et al., "Substituting Isoserine for Serine in the Thrombin Receptor Activation Peptide SFLLRN Confers Resistance to Aminopeptidase M-induced Cleavage and Inactivation," *J. Biol. Chem.* 268:20741-20743 (1993).
Cull et al., "Screening for Receptor Ligands Using Large Libraries of Peptides Linked to the C Terminus of the *lac* Repressor," *Proc. Natl. Acad. Sci. USA* 89:1865-1869 (1992).

(Continued)

*Primary Examiner* — Thomas Heard
(74) *Attorney, Agent, or Firm* — Goudreau Gage Dubuc; Alain Dumont

(57) ABSTRACT

Peptides that are designed to inhibit the biological activity of the IL-1R type 1 receptor and inhibit IL-1R/IL-1RacP related cell signaling and biological activity are disclosed. Compositions comprising IL-1R antagonists of the present invention are useful in the treatment of IL-1 related diseases or conditions such as arthritis, rheumatoid arthritis, osteoarthritis, and inflammatory bowel disease as well as other chronic or acute inflammatory diseases. This invention also discloses an isolated compound having an IL-1R antagonist activity, said compound being selected from the group consisting of: a peptide comprising the amino acid sequence RYTPELX, wherein R, Y, T, P, E, L, refer to their corresponding amino acids, and X is selected from no amino acid and alanine (A); and a derivative of (a) wherein the derivative incorporates one, two or three amino acid modification selected from an amino acid addition, deletion or substitution in the RYTPEL portion of the peptide, and wherein said derivative maintains its antagonist IL-1R activity.

16 Claims, 30 Drawing Sheets

(56) References Cited

OTHER PUBLICATIONS

DeWitt et al. "'Diversomers': an Approach to Nonpeptide, Nonoligomeric Chemical Diversity," *Proc. Natl. Acad. Sci. USA* 90:6909-6913 (1993).
Elliott et al., "Bin1 Functionally Interacts with Myc and Inhibits Cell Proliferation Via Multiple Mechanisms," *Oncogene* 18(24):3564-3573 (1999).
Erb et al. "Recursive Deconvolution of Combinatorial Chemical Libraries," *Proc. Natl. Acad. Sci. USA* 91:11422-11426 (1994).
Fodor et al. "Multiplexed Biochemical Assays with Biological Chips," *Nature* 364:555-556 (1993).
Gallop et al., "Applications of Combinatorial Technologies to Drug Discovery. 1. Background and Peptide Combinatorial Libraries," *Journal of Medicinal Chemistry* 37(9):1233-1251 (1994).
Hallegua et al., "Potential Therapeutic Uses of Interleukin 1 Receptor Antagonists in Human Diseases," *Ann Rheum Dis* 61(11):960-967 (2002).
Houghten et al., "The Use of Synthetic Peptide Combinatorial Libraries for the Identification of Bioactive Peptides," *Bio Techniques* 13(3):412-421 (1992).
Hu et al., "$\alpha_1$-Adrenergic Receptor Stimulation of Mitogenesis in Human Vascular Smooth Muscle Cells: Role of Tyrosine Protein Kinases and Calcium in Activation of Mitogen-Activated Protein Kinase," *J. Pharmacol. Exp. Ther.* 290(1):28-37 (1999).
Jameson et al., "A Rationally Designed CD4 Analogue Inhibits Experimental Allergic Encephalomyelitis," *Nature* 368:744-746 (1994).
Kendall et al., "Inhibition of Vascular Endothelial Cell Growth Factor Activity by an Endogenously Encoded Soluble Receptor," *Proc. Natl. Acad. Sci. USA* 90:10705-10709 (1993).
Lam et al., "A New Type of Synthetic Peptide Library for Identifying Ligand-Binding Activity," *Nature* 354:744-746 (1991).
Lam, "Application of Combinatorial Library Methods in Cancer Research and Drug Discovery," *Anti-Cancer Drug Design* 12:145-167 (1997).
Marciniak et al., "Epidermal Growth Factor Receptor-Related Peptide Inhibits Growth of PC-3 Prostate Cancer Cells," *Mol. Cancer Ther.* 3(12):1615-1621 (2004).
Merrifield, "Solid Phase Peptide Synthesis. I. The Synthesis of a Tetrapeptide," *J. Am. Chem. Soc.* 85:2149-2154 (1964).
Mickle et al., "Genotype-Phenotype Relationships in Cystic Fibrosis," *Med. Clin. North Am.* 84:597-607 (2000).
Piossek et al., "Vascular Endothelial Grown Factor (VEGF) Receptor II-Derived Peptides Inhibit VEGF," *The Journal of Biological Chemistry* 274(9):5612-5619 (1999).
Powell et al. "Peptide Stability in Drug Development. II. Effect of Single Amino Acid Substitution and Glycosylation on Peptide Reactivity in Human Serum," *Pharmaceutical Res.* 10(9):1268-1273 (1993).
Scott and Smith, "Searching for Peptide Ligands with an Epitope Library," *Science* 249:386-390 (1990).
Tamaskovic et al., "Enzyme-Linked Immunosorbent Assay for the Measurement of JNK Activity in Cell Extracts," *Biol. Chem.* 380:569-578 (1999).
Tan et al., "A Small Peptide Derived From Flt-1 (VEGFR-1) Functions as an Angiogenic Inhibitor," *FEBS Letters* 494:150-156 (2001).
Vigers et al., "X-ray Crystal Structure of a Small Antagonist Peptide Bound to Interleukin-1 Receptor Type 1," *J. Biol. Chem.* 275(47):36927-36933 (2000).
Yoon et al., "Antibodies to Domains II and III of the IL-1 Receptor Accessory Protein Inhibit IL-1β Activity But Not Binding: Regulation of IL-1 Responses is Via Type 1 Receptor, Not the Accessory Protein," *J. Immunol.* 3170-3179 (1998).
Zuckerman et al., "Discovery of Nanomolar Ligands for 7-Transmembrane G-Protein-Coupled Receptors from a Diverse N-(Substituted)glycine Peptoid Library," *J. Med. Chem.* 37:2678-2685 (1994).
International Search Report from PCT/CA2005/000691, mailed Aug. 25, 2005.
International Search Report from PCT/IB2006/002298, mailed Jan. 18, 2007.
Written Opinion from PCT/IB2006/002298, mailed Jan. 18, 2007.
International Preliminary Report on Patentability from PCT/IB2006/002298, dated Nov. 6, 2007.
Supplemental European Search Report (sESR) from EP 05 741 261.1-1223 mailed Nov. 19, 2008.
Akeson, A., et al., "AF12198, a Novel Low Molecular Weight Antagonist, Selectively Binds the Human Type I Interleukin (IL)-1 Receptor and Blocks in Vivo Responses to IL-1*", *J. of Biological Chemistry*, 271:30517-30523 (1996).
Brault, S., A. K. Martinez-Bermudez, et al., (2003). "Selective neuromicrovascular endothelial cell death by 8-Iso-prostaglandin F2alpha: possible role in ischemic brain injury." Stroke 34(3): 776-82.
Casadio, R., E. Frigimelica, et al. (2001). "Model of interaction of the IL-1 receptor accessory protein IL-1RAcP with the IL-1 beta/IL-1 R(I) complex." FEBS Lett 499(1-2): 65-8.
Cluzeau, J and Lubell W D. (2004). "Conformationally constrained dipeptide Surrogates with Aromatic Side-Chains: Synthesis of 4-Aryl Indolizidin-9-one Intermediate". J. Org. Chem. 69:1504-1512.
Cullinan, E. B., L. Kwee, et al. (1998). "IL-1 receptor accessory protein is an essential component of the IL-1 receptor." J Immunol 161(10): 5614-20.
Lombart, H.G. and Lubell, W.D. (1996). "Rigid Dipeptide mimetics: efficient synthesis of enantiopure indolizidinone amino acids" *J. Org. Chem.* 61:9437-9446.
Dietrich, E and Lubell W D. (2003). "Efficient Synthesis of Enantiopure Pyrrolizidinone Amino Acid" J. Org. Chem. 68: 6988-6996.
Feng Z, Lubell W D. (2001) "Mimicry of peptide Back-bone geometry and heteroatomic side-chain functionality: Synthesis of 7-[3-Azidopropyl]indolizidin-2-one amino acid as a constrained Ala-Lys dipeptide Surrogate" J. Org. Chem 66: 1181-1185.
Gosselin F and Lubell W D. (1998). "An olefination entry for the synthesis of enantiopure a,w-diamino-dicarboxylates and azabicyclo[X.Y.O]alkane amino acids." J. Org. Chem. 63: 7463-71.
Gosselin F and Lubell W D. (2000). "Rigid Dipeptide Surrogates: Suntheses of Enantiopure Quinolozidinone and Pyrroloazepinone Amino Acids from a Common Diaminodicarboxylate Precursor". J. Org. Chem. 65: 2163-2171.
Hanessian S, McNaughton-Smith, et al. (1997) "Design and synthesis of conformationally constrained amino acids as versatile scaffolds and peptide mimetics". Tetrahedron. 53: 12789-12854.
Hou, X., F. Gobeil, Jr., et al. (2000). "Augmented vasoconstriction and thromboxane formation by 15-F(2t)-isoprostane (8-isoprostaglandin F(2alpha)) in immature pig periventricular brain microvessels." Stroke 31(2): 516-24; discussion 525.
Kumar, S., P. C. McDonnell, et al. (2000). "Identification and initial characterization of four novel members of the interleukin-1 family." J Biol Chem 275(14): 10308-14.
Laye, S., J. Lundkvist, et al., (1998). "Human/mouse interleukin-1 receptor/receptor accessory protein interactions in Il-1 beta-induced NFkappaB activation." FEBS Lett 429(3): 307-11.
Masic L P and Kikelj D. (2001). Tetrahedron 57: 7073.
Pascal, R. and Sola, R.; Terahedron. Lett., 1998, 39, 5031-5034.
Polyak, F, Lubell W D. "Mimicry of peptides back-bone geometry and heteroatomic side-chain functionality: Synthesis of Enantiopure lndolizidin-2-one Amino Acids possessing Alcohol, Acid and Amine Functional Groups" J. Org. Chem. 66:1171-1180.
Sims, J. E., R. B. Acres, et al. (1989). "Cloning the interleukin 1 receptor from human T cells." Proc Natl Acad Sci USA 86(22): 8946-50.
Takami, H., et al., "Complete genome sequence of the alkaliphilic bacterium Bacillus halodurans and genomic sequence comparison with Bacillus subtilis", *Nucleic Acids Res.* 28:4317-4331 (2000).
Vigers, G. P., L. J. Anderson, et al. (1997). "Crystal structure of the type-I interleukin-1 receptor complexed with interleukin-1beta." Nature 386(6621): 190-4.
Anthony D., Savage F. et al. (1995) "The characterization of a rabbit model of inflammatory bowel disease", *Int. J Exp Path* 76:215-224.

(56) References Cited

OTHER PUBLICATIONS

Asadullah K., Sabat R., Friedrich M., et al. (2004) "Interleukin-10: an important immunoregulatory cytokine with major impact on psoriasis" *Curr Drug Targets Inflamm Allergy* 3(2):185-92.
Barnstable C.J., Tombran-Tink J. (2004) "Neuroprotective and antiangiogenic actions of PEDF in the eye: molecular targets and therapeutic potential" *Prog Retin Eye Res* 23(5):561-77.
Beauchamp, M.H., A.K. Martinez-Bermudez, et al. (2001) "Role of thromboxane in retinal microvascular degeneration in oxygen-induced retinopathy" *J Appl Physiol* 90(6):2279-88.
Bouma, G. and W. Strober (2003) "The immunological and genetic basis of inflammatory bowel disease" *Nat Rev Immunol* 3(7):521-33.
Daun J.M., Fenton, M.J. (2000) "Interleukin-1/Toll receptor family members: receptor structure and signal transduction pathways" *J. Interferon Cytokine Res* 20(10):843-55.
Dettwiler JE, Lubell WD (2003) "Serine as Chiral Educt for the Practical Synthesis of Enantiopure N-Protected Beta-Hydroxyvaline" *J Org Chem* 68:177-179.
Dunne A., and L.A. O'Neill (2003) "The interleukin-1 recep or/Toll-like receptor superfamily". *Sci STKE* 171:re-EOA.
Gabay, C (2000) "IL-1 inhibitors: novel agents in the treatment of rheumatoid arthritis" *Expert Opin Investig Drugs* 9(1):113-27.
Halab, L., et al. (2000) "Design, synthesis and conformational analysis of Azacycloalkane amino acids as conformationally constrained probes for mimicry of peptide secondary structures" *Biopolymers, Peptide Science* 55:101-22.
Hardy, P., A.M. Nuyt et al (1999) "Developmentally increased cerebrovascular NO in newborn pigs curtails cerebral blood flow autoregulation" *Pediatr Res* 46(4):375-82.
Hou, S., F. Gobeil, Jr., et al. (2003) "Increased platelet-activating factor induced periventricular brain microvascular constriction associated with immaturity" *Am J Physiol Regul Integr Comp Physiol* 284(4):R928-35.
Hou, X., L.J. Roberts, $2^{nd}$, et al. (2001) "2,3 Dinor-5,6-dihydro-15-F(2t)-isoprostane: a bioactive prostanoid metabolite"*Am J. Physiol Regul Integr Comp Physiol* 281(2):R391-400.
Kashiwamura, S. Ueda, H. and Okamura H. (2002) "Roles of interleukin-18 in tissue destruction and compensatory reactions" *J Immunother* 25(Suppl.):S4-11.
Lapatsanis, L., Milias, G., et al. (1983) "Synthesis of N-2,2,2-(Trichloroethoxycarbonyl)-L-amino acids and N-(9-Fluorenylmethoxycarbonyl)-L-amino acids involving succimimidoxy anion as a leaving group in amino acid protection" *Synthesis* pp. 671-673.
Li, D.Y., P. Hardy et al. (1997) "Key role for cyclooxygenase-2 in PGE2 and PGF2alpha receptor regulation and cerebral blood flow of the newborn" *Am J. Physiol* 273(4Pt.2):R1283-90.
Li, MC, He, SH (2004) "IL-10 and its related cytokines for treatment of inflammatory bowel disease" *World j Gastroenterol* 10(5):620-5.
Meienhofer, J., Waki, M., et al. (1979) "Solid phase synthesis without repetitive acidolysis" *Int J Peptide Protein Res* 13:35-42.
Najarian, T., A.M. Marrache, et al. (2000) "Prolonged hypercapnia-evoked cerebral hyperemia via K(+) channel- and prostaglandin E(2)-dependent endothelial nitric oxide synthase induction" *Circ Ref* 87(12):1149-56.
Padol I., Huang, J.Q., et al. (2000) "Therapeutic effects of the endothelin receptor antagonist Ro 48/5695 in the TNBS/DNBS rat model of colitis" *Eur J of Gastroenterol Hepatol* 12:257-265.
Schuerwegh, A.J., et al. (2003) "Influence of pro-inflammatory (IL-1, IL-6, THF-alpha, IFN-gamma) and anti-inflammatory (114) cytokines on chondrocytes function" *Osteoarthritis Cartilage* 11(9):681-7.
Sims, J.E. (2002) "IL-1 and IL-18 receptors, and their extended family" *Curren Opin in Immunology* 14(1):117-122.
Torres M.I., Garcia-Martin M., et al. (1999) "Experimental colitis induced by trinitrobenzenesulfonic acid" *Digestive Diseases and Sciences* 44(12):2523-2529.
Malinowsky, D., et al. (1998) "Interleukin-1 receptor accessory protein interacts with the type II interleukin-1 receptor" *FEBS Letters* 429:299-302.

Aribia et al, "rIL-2-induced proliferation of human circulating NK cells and T lymphocytes: Synergistic effects of IL-1 and IL-2," *J. Immunol.* 139(2):443-451 (1987).
Supplementary European Search Report, EP 06795318.2, date of mailing Jan. 22, 2009.
Berezov et al, "Disabling receptor ensembles with rationally designed interface peptidomimetics," *J. Biol. Chem.* 277:28330-28339 (2002).
Percherancier et al, "Bioluminescence resonance energy transfer reveals ligand-induced conformational changes in CXCR4 homo- and heterodimers," *J. Biol. Chem.* 280:9895-9903 (2005).
Kumar et al, "Interleukin-1 alpha promotes tumor growth and cachexia in MCF-7 xenograft model of breast cancer," *Am. J. Pathol.* 163:2531-2541 (2003).
Cox et al, "Characterization of IL-2 receptor expression and function on murine macrophages," *J. Immunol.* 145:1719-1726 (1990).
Changeux et al, "Allosteric mechanisms of signal transduction," *Science* 308:1424-1428 (2005).
Christopoulos et al, "G-protein-coupled receptor allosterism: the promise and the problem(s)," *Biochem. Soc. Trans.* 32:873-877 (2004).
Loetscher et al, "Agonistic and antagonistic activities of chemokines," *J. Leukoc. Biol.* 69:881-884 (2001).
Ogilvie et al, "Unusual chemokine receptor antagonism involving a mitogen-activated protein kinase pathway," *J. Immunol.* 172:6715-6722 (2004).
Rost et al, "PHD: predicting one-dimensional protein structure by profile-based neural networks," *Methods Enzymol.* 266:525-539 (1996).
Schon et al, "Animal Models of Psoriasis—What Can We Learn from Them?" *J. Investig. Derm.* 112:405-410 (1999).
Kenakin et al, "Allosteric Modulators: The New Generation of Receptor Antagonist," *Mol. Intervention* 4:222-229 (2004).
Petersen et al, "In vivo pharmacological disease models for psoriasis and atopic dermatitis in drug discovery," *Basic & Clinical Pharm. Tox.* 99:104-115 (2006).
Freir et al, "Blockade of long-term potentiation by beta-amyloid peptides in the CA1 region of the rat hippocampus in vivo," *J. Neurophysiol.* 85(2):708-13 (2001).
Lie et al, "Synthesis and biological activity of four kinds of reversed peptides," *Biol. Pharm. Bull.* 19(12):1602-6 (1996). [Abstract only].
Lee et al, "Antibiotic activity of reversed peptides of alpha-helical antimicrobial peptide, P18," *Protein Pept. Left.* 9(5):395-402 (2002).
Jois et al, "Comparison of the solution conformations of a cell-adhesive peptide LBE and its reverse sequence EBL," *J. Biomol. Struct. Dyn.* 17(3):429-44 (1999). [abstract only].
Hautanen et al, "Effects of modifications of the RGD sequence and its context on recognition by the fibronectin receptor," *J. Biol. Chem.* 264(3)1437-42 (1989).
Chorev et al, "Recent developments in retro peptides and proteins—an ongoing topochemical exploration," *Trends Biotechnol.* 13(10):438-45 (1995).
Doi et al, "Conserved delta-activity in reverse enantiomeric opioid peptide." *Life Sci.* 56(19):1557-62 (1995).
Brenneman et al, "Protective peptides that are orally active and mechanistically nonchiral." *J. Pharmacol. Exp. Ther.* 309(3):1190-7 (2004).
Nomizu et al, "The all-D-configuration segment containing the IKVAV sequence of laminin A chain has similar activities to the all-L-peptide in vitro and in vivo." *J. Biol. Chem.* 267(20):14118-21 (1992).
Ido et al, "Prevention of vascular and neural dysfunction in diabetic rats by C-peptide." *Science* 277(5325):563-6 (1997).
Hebert et al, "A peptide derived from a $\beta_2$-adrenergic receptor transmembrane domain inhibits both receptor dimerization and activation," *J. Biol. Chem.* 271:16384-16392 (1996).
Souroujon et al, "Peptide modulators of protein-protein interactions in intracellular signaling," *Nat. Biotechnol.* 16:919-924 (1998).
Salamat-Miller et al, "Current strategies used to enhance the paracellular transport of therapeutic polypeptides across the intestinal epithelium," *Int. J. Pharm.* 294:201-216 (2005).

\* cited by examiner

Optimization of IL-1R candidates

| | |
|---|---|
| API-101.10 | RYTVELA |
| API-101.101 | XYTVELA (X=Citruline) |
| API-101.102 | XYTVQLA (X=Citruline) |
| API-101.103 | RYTVQLA |
| API-101.104 | RFTVELA |
| API-101.105 | RYSVELA |
| API-101.106 | RYVVELA |
| API-101.107 | RYTPELA |
| API-101.108 | RYTVEL |

Figure 13

Characterization of 101.10 peptide derivatives

*In vitro* peptide inhibition of PGE$_2$ synthesis by IL-1β

| Peptide | Sequence | Endothelial cells (porc.) | | WI-38 (hum.) | |
|---|---|---|---|---|---|
| | | IC$_{50}$ | Emax (%) | IC$_{50}$ | Emax (%) |
| 101.10 | RYTVELA | 1.2nM | 90 | 0.2nM | 81 |
| 101.101 | [Cit]YTVELA | 0.8μM | 0 | 0.9μM | 45 |
| 101.102 | [Cit]YTVQLA | 0.2μM | 0 | 0.2nM | 46 |
| 101.103 | RYTVQLA | 6.3pM | 59 | 0.05pM | 52 |
| 101.104 | RFTVELA | 623μM | 25 | 0.4μM | 28 |
| 101.105 | RYSVELA | 0.3μM | 21 | 0.5pM | 53 |
| 101.106 | RYVVELA | 0.4nM | 55 | 1.4nM | 65 |
| 101.107 | RYTPELA | 13.1pM | 50 | 0.1pM | 57 |
| 101.108 | RYTVEL | 21.6μM | 34 | 0.6μM | 35 |

Figure 15

Effect of API-101.10 (systemic) in a rat model of Inflammatory Bowel Disease*
(histology)

A) Saline    B) TNBS + Saline    C) TNBS + API-101.10
(1.1 mg/kg/d)

*Two treatments with TNBS (20mg/ml) were given to the animals at an interval of 5 days. The animals were sacrificed 7 days after the first treatment with TNBS. Half dose of API-101.10 was given compared to macroscopic data.

| Peptide # | Peptide sequence | Efficacy relative to IL-1β induced PGE$_2$ production in presence of peptides (%) | |
| --- | --- | --- | --- |
| | | EC (porcine) | Chondrocytes |
| API-101 | APRYTVELA | 51 | 33 |
| API-101.1 | A<u>A</u>RYTVELA | 54 | 56 |
| API-101.2 | AP<u>A</u>YTVELA | <25 | <25 |
| API-101.3 | APR<u>A</u>TVELA | 40 | 37 |
| API-101.4 | APRY<u>A</u>VELA | <25 | 55 |
| API-101.5 | APRYT<u>A</u>ELA | 0 | <25 |
| API-101.6 | APRYTV<u>A</u>LA | 0 | 0 |
| API-101.7 | APRYTVE<u>A</u>A | 0 | <25 |

Figure 17

Characterization of 101 peptide derivatives

| Peptide | Sequence | *In vitro* peptide inhibition of PGE$_2$ synthesis by IL-1β (IC$_{50}$) | | | | *Ex vivo* peptide inhibition of IL-1β vasodilatation of porcine pial vessels (IC$_{50}$; Emax=100%) |
|---|---|---|---|---|---|---|
| | | WI-38 (hum.) | | EC (porc.) | | |
| | | IC$_{50}$ | Emax (%) | IC$_{50}$ | Emax (%) | |
| 101 | APRYTVELA | 790 nM | 100 | 220 nM | 100 | 182 nM |
| 101.9 | PRYTVELA | 1 μM | 48 | 300 nM | 81 | <100 nM |
| 101.10 | RYTVELA | 0.2 nM | 81 | 1.2 nM | 90 | 10.8 nM |
| 101.11 | YTVELA | 6 μM | 61 | 1.4 μM | 75 | 23 nM |
| 101.12 | TVELA | ud | 19 | 4.1 μM | 85 | 47.3 nM |

Figure 18

Legend figure 19 : PGE$_2$ production in endothelial cells stimulated with IL-1β (10 ng/ml) in presence of peptidomimetics 101.109 and 101.110

101.107: EC$_{50}$ = 43 pM  Emax=60 %
101.109: EC$_{50}$ = 49 pM, Emax=84%
101.110: EC$_{50}$ = 0.2 pM, Emax=82%

"C50110"

API-101.110: ry(I2aa)ela.

†(adapted from Peterson et al., Dig Dis Sci, 2000)

* Median score on 4 separate slide preparations

A Saline
B TNBS + Saline
C TNBS + 101.10 (1.0 mg/kg/d), i.p., BID
D TNBS + 101.107 (0.2 mg/kg/d), i.p., BID

| Results of peptidomimics | | |
|---|---|---|
| Peptide | IC$_{50}$ | Efficacy |
| TTI-101.110 | 10 pM | 90% |
| TTI-101.112 | nd | < 10% |
| TTI-101.124 | 2.4 µM | --- |
| TTI-101.125 | 90 pM | 100 % |

Figure 26

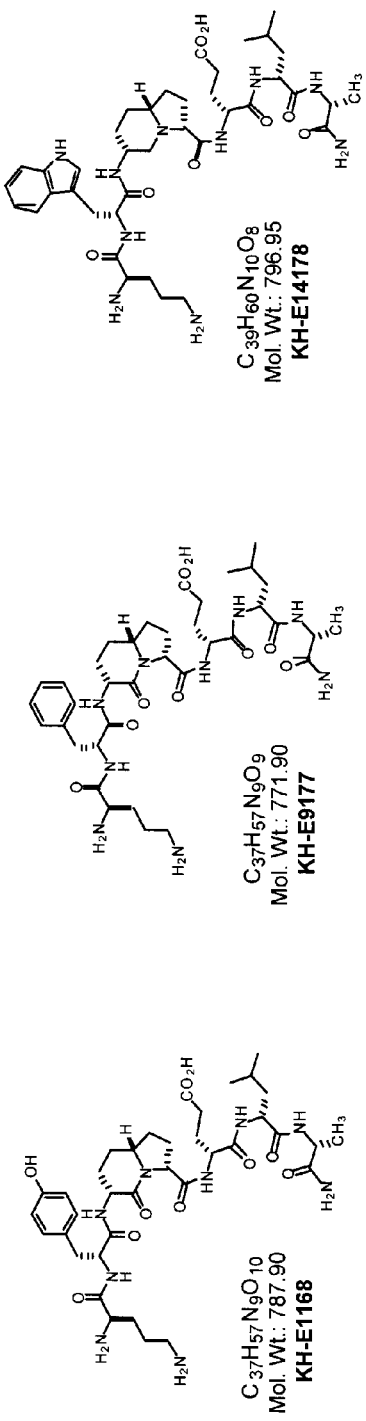
Peptidomimetic structures
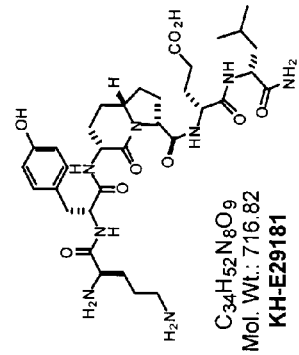
TTI-101.140
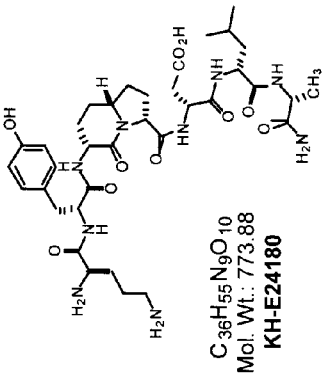
TTI-101.139
Figure 27
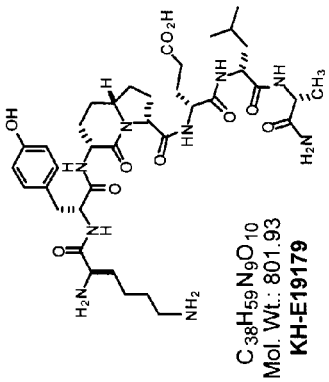
TTI-101.138

Peptidomimetic structures

TTI-101.142

TTI-101.144

TTI-101.141

TTI-101.143

Figure 29
Peptidomimetics

| | Structures | TF-1 proliferation | | Inhibition of NFκB activation | |
|---|---|---|---|---|---|
| | | IC$_{50}$ | E$_{max}$ (%) | IC$_{50}$ | E$_{max}$ (%) |
| TTI-101.1255 (KH-E1168) (reference mimetic) | | 90 pM | 100 | not done | not done |
| TTI-101.1356 (KH-E9177) | | 50 nM | 60 | 30 nM | 60 |
| TTI-101.1377 (KH-E14178) | | --- | < 5 | agonist | |
| TTI-101.1388 (KH-E19179) | | >0.5 μM | 20 | --- | --- |
| TTI-101.1359 (KH-EC24180) | | --- | 20 | --- | --- |
| TTI-101.1440 (KH-E29181) | | 3 pM | 70 | 1 pM | 50 |

| Peptidomimetic | Structure | TF-1 proliferation IC$_{50}$ / E$_{max}$ (%) | Inhibition of NFκB activation IC$_{50}$ / E$_{max}$ (%) |
|---|---|---|---|
| TTI-101.141 (DBG171-1) | 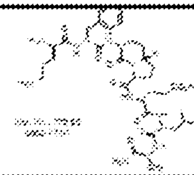 | 1 pM    75 | 3 pM    70% |
| TTI-101.142 (DBG171-3) | 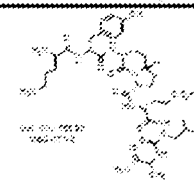 | 2 nM agonist activity | 4 nM agonist activity |
| TTI-101.143 (DBG171-4) | 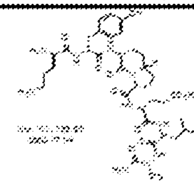 | 50 nM    75 | 1 nM    60% |
| TTI-101.144 (DBG176) | 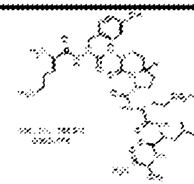 | Efficacy over 5 logs | ---    35% |
| TTI-101.125 (KE-E1149) (reference mimetic) |  | 90 pM    100 | |

INTERLEUKIN-1 RECEPTOR ANTAGONISTS, COMPOSITIONS, AND METHODS OF TREATMENT

This Application claims the benefit of U.S. Provisional Application No. 60/714,512 filed May 5, 2004.

FIELD OF THE INVENTION

The present invention relates to IL-1 receptor antagonists and methods of modulating IL-1 receptors activity with same. More specifically, the present invention is concerned with extracellular, non-competitive IL-1 receptor (IL1R/IL1RAcP) peptides and peptidomimetic antagonists, their identification and their therapeutic uses. More particularly, the present invention relates to peptide and peptidomimetic antagonists for use in the treatment of IL-1 associated diseases such as rheumatoid arthritis and inflammatory bowel disease. The present invention has application in the field of biochemistry and medicinal chemistry.

BACKROUND OF THE INVENTION

Cytokines are generic terms for designating biologically active hormone-like proteins (interleukins, interferons, tumor necrosis factor, growth factors) that mediate their effects through a superfamily of receptors. Cytokines and their receptors constitute a powerful control network by which cells signal and coordinate cell proliferation and differentiation, cell death and survival. Cytokines can be specifically low molecular weight peptides having very potent biological activity. Their mechanism of action is generally autocrine and paracrine and they act ultimately by regulating gene expression.

The Interleukin-1 (IL-1) family of polypeptide hormones represent an important class of cytokines which are expressed by a variety of cell types including monocytes (which is the predominant source of IL-1), fibroblasts, endothelial cells, smooth muscle cells, osteoclasts, astrocytes, epithelial cells, T-cells, B-cells and numerous cancer cells. This family of cytokines consists of more than 7 distinct but structurally related molecules including IL-1α, IL-1β and IL-18, which elicit a biologic response, and IL-1ra, a naturally produced receptor antagonist (Kumar, et al. 2000).

IL-1α and IL-1β genes are both located on chromosome 2. Each gene contains seven exons and are homologous in a region of the sixth exon. Both IL-1α and IL-1β are initially produced as 31 kDa precursors but are processed by proteases to produce the 17.5 kDa mature proteins. Receptors for IL-1 recognize both α and β forms and both forms have similar biological properties. IL-1α is the predominant form in mice whereas IL-1β is the predominant cytokine in human. The biological properties of IL-1 are numerous and include mediating many immunological and inflammatory responses to infection and injury.

Despite its normally beneficial effects on an organism response to infection and injury, circumstances have come to light in which the actions of IL-1 are harmful. For example, inappropriate production or response to IL-1 have been shown in many acute and chronic inflammatory diseases such as rheumatoid arthritis, inflammatory bowel disease (IBD), osteoarthritis, psoriasis, septic shock, encephalitis and respiratory distress syndrome. IL-1 has been shown to play a role in several other illnesses including Alzheimer's disease, periventricular leukomalacia, meningitis, stroke, and a number of autoimmune diseases.

Interleukin-1 (IL-1) plays a primary upstream role in the regulation of inflammation by stimulating generation of inflammatory mediators like IL-6, prostaglandin $E_2$ ($PGE_2$; via the induction the COX-2 and PGE synthase (mPGES) expression) and itself, therefore enhancing the process of inflammation. Another biological activity of IL-1 is to induce proliferation and activation of numerous cell types like T-cells (Cullinan, et al. 1998; Dunne and O'Neill 2003). IL-1 may also increase the level of collagenase in an arthritic joint and has been implicated in the acute and chronic stages of immunopathology in rheumatoid arthritis. IL-1 may be responsible for altering endothelial cell function, directing the chemotaxis of lymphocytes and leucocytes into synovial tissue and inducing the secretion of latent collagenase by chondrocytes and fibroblasts. IL-1 is considered, along with TNF, as the prototype of inflammatory cytokines. However, the effects of IL-1 are not limited to inflammation and this cytokine also plays a role in bone formation and remodeling, insulin secretion and fever induction.

As a major pro-inflammatory cytokine, IL-1 is a potentially powerful target for therapeutic intervention in diseases like articular cartilage injury such as in arthritis. Osteoarthritis and rheumatoid arthritis are only second to heart disease for causing work disabilities in North America and their prevalence increase dramatically with age (Hallegua and Weisman 2002).

Two distinct receptors of IL-1 have been cloned and characterized: IL-1RI (Sims, et al. 1989), which generates the biological effects of IL-1; and IL-1RII. In addition, a receptor accessory protein (IL-1RAcP), which is the putative signal-transducing subunit of the receptor complex, has been identified. IL-1R type I is found mainly on T cells, keratinocytes, fibroblasts, chondrocytes, synovicytes and epithelial cells. In order to generate a biological effect, IL-1R has to bind to IL-1 and subsequently to IL-1RAcP to trigger signal transduction. The extracellular portion of IL-1R contains three Ig-like domains that bind IL-1 (Vigers, et al. 1997; Vigers et al. 2000). As opposed to the IL-1R receptor subunit and according to studies involving antibodies against extracellular portions of IL-1R accessory protein, the latter does not interact with the cytokine (Cullinan et al. 1998; Laye et al. 1998; Malinowsky et al. 1998; Casadio et al. 2001).

The first event in signal transduction, following IL-1 binding, is the formation of an IL-1R/IL-1RacP complex which leads to IRAK (IL-1 receptor associated kinase) recruitment to the complex and to a cascade of phosphorylation by kinases, causing the activation of transcriptional factors including NFκB and AP-1. The IL-1R/IL-1RacP complex can also recruit and activate kinases like PI3K and Akt and can also lead to the activation of the PLC/PKC pathway of signalization (Daun and Fenton, 2000).

Two major clinical applications of IL-1R antagonists are the treatment of arthritis and inflammatory bowel disease (IBD). The treatments available for these pathologies are currently limited. They often result in toxicity and secondary effects. The demand in the medical world for safer and more targeted therapies is therefore considerable.

The current approaches in the field of IBD and rheumatoid arthritis therapies include the development of soluble receptors, monoclonal antibodies directed against IL-1R and TNFR, mimetic of cytokines, antisense techniques and kinase inhibitors (Vigers et al. 1997; Vigers et al. 2000; Hallegua and Weisman 2002; Bouma and Strober 2003). In the particular case of IL-1, a natural soluble receptor IL-1Ra mimetic, Anakinra, (generic name Kineret™) was developed by Amgen for treatment of severely active rheumatoid arthritis in replacement of methotretaxe (an inhibitor of dihydrofolate (folic acid) reductase enzyme). In the case of another major pro-inflammatory cytokine receptor, TNFR, two antagonists, etanercept (Enbrel™, Amgen) and infliximab (Remicade™, Schering-Plough), have also been developed.

Antagonists of the prior art are either competitive (e.g. soluble receptors, antibodies, cytokine mimetics), most often costly to produce or difficult to apply in vivo (e.g., antisense). Because the ligand exceeds by far the concentration of the receptor, the concentration of competitive inhibitor needed to inhibit the interaction of IL-1 with its native receptor is often substantial.

Therefore, there remains a need for novel therapies that can down-regulate the activity mediated by IL-1.

The present invention seeks to meet these needs and other needs.

The present description refers to a number of documents, the content of which is herein incorporated by reference in their entirety.

SUMMARY OF THE INVENTION

The present invention thus concerns non-competitive, efficient and selective extracellular IL-1 receptor antagonists, which overcome one or more of the drawbacks of the IL-1 receptor antagonists of the prior art.

The present invention also relates to the use of the non-competitive and selective antagonists of the present invention in the treatment of IL-1 associated diseases.

In one embodiment, the compounds of the present invention are peptides and peptidomimetics that inhibit the biological activity of IL-1R and inhibit cytokine activity by preventing signaling through the receptor. Thus, the inhibition of IL-1 mediated events leads for example, to anti-inflammatory responses, which are beneficial for the prophylaxis or treatment of a variety of chronic and acute inflammatory diseases such as rheumatoid arthritis and inflammatory bowel disease, among other inflammatory diseases and diseases and conditions associated with IL-1 function.

Designed to seek extracellular targets, unlike certain known drug candidates which target intracellular regions of the IL-1 receptors, the antagonists of the present invention do not necessitate a prior permeabilization or other disruption of cell membranes to gain access to the target cell in order to produce a pharmacological response.

Because they function as non-competitive antagonists, a smaller amount of the antagonists of the present invention is necessary to inhibit the receptor that they target, as compared to competitive inhibitors.

In a related embodiment, the antagonists of the present invention are advantageously simple to synthesize.

The peptides, derivatives and peptidomimetics thereof of the present invention interact with a specific extracellular domain of the IL-1R/IL-1RacP receptor complex so as to inhibit the activity of the receptor. Importantly, the peptides, peptide derivatives and peptidomimetics of the present invention do not interact with the IL-1 binding site on the IL-1 R subunit and thus are considered non-competitive peptide antagonists. The antagonists of the present invention are derived from the following API-101 sequence: APRYTVELA (SEQ ID NO: 1) all with D-amino acids except where indicated (the asterisk in SEQ ID NO: 39 indicates that the residue (R) is an L-amino acid, see Table 1).

TABLE 1

LIST OF SEQUENCE NUMBERS

| | | |
|---|---|---|
| SEQ ID NO : 1 | API-101 | APRYTVELA |
| SEQ ID NO : 2 | API-101.1 | AARYTVELA |
| SEQ ID NO : 3 | API-101.2 | APAYTVELA |
| SEQ ID NO : 4 | API-101.3 | APRATVELA |
| SEQ ID NO : 5 | API-101.4 | APRYAVELA |
| SEQ ID NO : 6 | API-101.5 | APRYTAELA |
| SEQ ID NO : 7 | API-101.6 | APRYTVALA |
| SEQ ID NO : 8 | API-101.7 | APRYTVEAA |
| SEQ ID NO : 9 | API-101.9 | PRYTVELA |
| SEQ ID NO : 10 | API-101.10 | RYTVELA |
| SEQ ID NO : 11 | API-101.11 | YTVELA |
| SEQ ID NO : 12 | API-101.12 | TVELA |
| SEQ ID NO : 13 | API-101.101 | XYTVELA (X = Citrulline) |
| SEQ ID NO : 14 | API-101.102 | XYTVQLA (X = Citrulline) |
| SEQ ID NO : 15 | API-101.103 | RYTVQLA |
| SEQ ID NO : 16 | API-101.104 | RFTVELA |
| SEQ ID NO : 17 | API-101.105 | RYSVELA |
| SEQ ID NO : 18 | API-101.106 | RYVVELA |
| SEQ ID NO : 19 | API-101.107 | RYTPELA |
| SEQ ID NO : 20 | API-101.108 | RYTVEL |
| SEQ ID NO : 21 | API-101.113 | RYTPEL |
| SEQ ID NO : 22 | API-101.114 | KYTPELA |
| SEQ ID NO : 23 | API-101.115 | XYTPELA (X = Ornithine) |
| SEQ ID NO : 24 | API-101.116 | RWTPELA |
| SEQ ID NO : 25 | API-101.117 | RYTPDLA |
| SEQ ID NO : 26 | API-101.118 | RYTPQLA |
| SEQ ID NO : 27 | API-101.119 | RYTPEFA |
| SEQ ID NO : 28 | API-101.120 | RYTPEMA |
| SEQ ID NO : 29 | API-101.121 | XRYTPELA (X = Acetyl) |
| SEQ ID NO : 30 | API-101.122 | RYTPEPA |
| SEQ ID NO : 31 | API-101.123 | RYTPALA |
| SEQ ID NO : 32 | API-101.126 | XYTPEL (X = Ornithine) |
| SEQ ID NO : 33 | API-101.127 | RFVPELA |
| SEQ ID NO : 34 | API-101.128 | RWTPEL |
| SEQ ID NO : 35 | API-101.129 | RYTPEV |
| SEQ ID NO : 36 | API-101.132 | RFTPEL |
| SEQ ID NO : 37 | API-101.133 | KYTPEL |

TABLE 1-continued

LIST OF SEQUENCE NUMBERS

| SEQ ID NO : 38 | API-101.134 | XYTPEL (X = Citrulline) |
|---|---|---|
| SEQ ID NO : 39 | API-101.135 | *RYTPEL |

Without being limited to a particular theory, IL-1 receptor antagonists may promote or stabilize a particular conformation of the IL-1 receptor, which results in inhibition, of the receptor activity. The peptides, peptide derivatives and peptidomimetics of the present invention inhibit IL-1 dependent intracellular signaling in a non-competitive way. These peptides effectively prevent activation of the intracellular receptor domains responsible for IL-1 receptor signaling. Subsequent cell transduction events leading to expression of molecules (e.g., inflammatory molecules like cytokines, cytokines receptors, prostaglandins, collagenase secretion . . . etc) responsible in part for disease expression are thereby prevented.

These compounds include lead compounds and derivative compounds constructed so as to have the same or similar molecular structure or shape, as the lead compounds, but may differ from the lead compounds either with respect to susceptibility to hydrolysis or proteolysis, or with respect to their biological properties (e.g., increased affinity for the receptor). The present invention also relates to compounds and compositions that are useful for the treatment or prevention of conditions, diseases or disorders associated with inappropriate IL-1 production or IL-1 response.

In another embodiment, the present invention also relates to pharmaceutical compositions comprising one or more of the compounds described herein and a physiologically acceptable carrier. These pharmaceutical compositions can be in a variety of forms including oral dosage forms, topic creams, suppository, nasal spray and inhaler, as well as injectable and infusible solutions. Methods for preparing pharmaceutical composition are well known in the art as reference can be made to Remington's Pharmaceutical Sciences, Mack Publishing Company, Eaton, Pa., USA.

The method of treatment of the present invention may be preventive and reduce the risk of developing an IL-1 associated disease or condition, and may be used to alleviate or obviate the condition. The administration of the therapeutic agent can be in any pharmaceutically acceptable form in a suitable carrier, and in therapeutically acceptable dose.

In view of the importance of IL-1 and or IL-1R/IL1RacP receptor function in numerous pathways and conditions in animals, the present invention has a broad impact on the identification, validation and treatment of conditions or diseases associated with IL-1 response (e.g., IL-1 overexpression or abnormal signaling through IL-1R/IL1-RacP).

The present invention also concerns non-competitive, efficient and selective extracellular receptor agonists. In addition, the invention relates to the use of the non-competitive and selective agonists of the present invention in the treatment of interleukin-associated diseases in which the interleukin-1 (IL) already displays an inflammatory activity or other activity, one or more of an agonist of the present invention increasing the activity of the IL having the above-mentioned anti-inflammatory activity, or other activity. In a related embodiment, the agonists of the present invention are advantageously simple to synthesize. Non-limiting examples of agonists in accordance with the present invention include peptides TTI-101.101 (SEQ ID NO:13) and TTI-101.102 (SEQ ID NO:14) as well as peptidomimetic TTI-101-137 and TTI-101-142 (FIGS. 29 and 30, respectively).

Non limiting examples of cytokines receptors for which agonists of the present invention can find a therapeutic use include:

(1) Pigment epithelium-derived factor. PEDF is synthetized by retinal pigment epithelial cells and is an anti-angiogenic factor in the retina. It also protects neurons from oxidative stress and glutamate exotoxicity. An agonist of the present invention would thus have a therapeutic potential in case of abnormal neovascularization in the retina and in tumor growth (e.g. diabetic retinopathy, retinopathy of prematurity, and cancer; Barnstable et al. 2004).

(2) IL-4 receptor: IL-4 is an anti-inflammatory cytokine that may inhibit the production of inflammatory molecules like IL-1, IL-6, TNF alpha by monocytes and TNF-alpha by T-cells at the inflammatory site. IL-4 also inhibits the growth of colon and mammary carcinomas. It also acts as an anti-inflammatory cytokine in rheumatoid arthritis by a protective action on chondrocytes and the inhibition of the production of inflammatory mediators (Schuerwegh, et al).

(3) The IL-10 cytokines family: All of this family as a beneficial effect on the inflammation site and its anti-inflammatory effect has been described in the case of wound healing, inflammatory bowel disease and psoriasis. IL-10 decreases the production of pro-inflammatory factors like IL-2, TNF-alpha and IFN-gamma in Th1 cells. It decreases tumor growth by inhibiting the infiltration of macrophages on tumor site (Li et al. 2004; Asadullah et al. 2004).

In one embodiment the present invention relates to an isolated compound selected from the group consisting of: a) a peptide, or isolated peptide which binds to IL-1R, or has an IL-1R antagonist activity (e.g. IL-1R/IL-1RacP antagonist activity), wherein the peptide or isolated peptide comprises the amino acid sequence RYTPELA (SEQ ID NO: 19), wherein R, Y, T, P, E, L, and A refer to their corresponding amino acids, and wherein said peptide can bind to IL-1R or has an IL-1R antagonist activity (e.g. IL-1R/IL-1RacP antagonist activity); and b) a derivative of (a) wherein the derivative incorporates from one to four amino acid addition, deletion or substitution, and wherein the derivative competes with said peptide of (a) for binding to IL-1R or maintains its IL-1R antagonist activity (e.g. IL-1R/IL-1RacP antagonist activity). In one particular embodiment, such derivative incorporates three, two or one amino acid addition, deletion or substitution.

In one further embodiment, the present invention relates to a peptide, or isolated peptide which antagonizes the biological activity of IL-1R wherein the peptide or isolated peptide comprises the sequence characterized by the general formula: RYTPELX (SEO ID NO: 40), wherein R, Y, T, P, E, and L, refer to their corresponding amino acids, and wherein X is selected from no amino acid and alanine (A). The invention also relates to derivatives of this general formula, wherein the derivative incorporates one, two or three amino acid modification selected from an amino acid addition, deletion, or substitution in the RYTPEL (SEQ ID NO: 21) portion of the peptide RYTPELX (SEQ ID NO: 40), and wherein the derivative maintains its antagonist IL-1R activity, (e.g. IL-1R/IL-1RacP antagonist activity). Generally the substitution of an amino acid is made with a similar or conserved amino acid, see below.

In one further embodiment, the derivative comprises two or less amino acid modification selected from an amino acid addition, deletion or substitution in the RYTPEL (SEQ ID NO: 21) portion of the peptide. In one particular embodiment such the peptide, isolated peptide or derivative thereof is selected from the group consisting of: 101-113, 101-103, 101-114, 101-117, 101.10, 101.106, 101.116, 101.108, 101.135, 101.128, 101.9, 101.105, 101.129, 101.11, 101.12, and 101.132. In yet another particular embodiment, the antagonist compounds are selected from the group consisting of: 101-113, 101-103, 101-114, 101-117, and 101.10.

In yet another embodiment, the present invention relates to an isolated compound having an IL-1R/IL1RacP antagonist activity, said compound being selected from the group consisting of: a) a peptide comprising the amino acid sequence RYTPELX (SEQ ID NO: 40), wherein R, Y, T, P, E, L, refer to their corresponding amino acids, and X is selected from no amino acid and alanine (A); and a derivative of (a) wherein the derivative incorporates one, two or three amino acid modification selected from an amino acid addition, deletion or substitution in the RYTPEL portion of the peptide, and wherein the derivative maintains its antagonist IL-1R/IL1RacP activity. The invention of course also relates to such derivatives having only one, or only two such modification. Examples of such antagonists comprise peptides 101-113, 101-103, 101-114, 101-117, 101.10, 101.106, 101.116, 101.108, 101.135, 101.128, 101.9, 101.105, 101.129, 101.11, 101.12, and 101.132, and more peptides 101-113, 101-103, 101-114, 101-117, and 101.10.

In one specific embodiment, the present invention relates to a peptide which antagonizes the biological activity of IL-1R, wherein the peptide comprises the sequence characterized by the general formula:

X-$aa_1$-$aa_2$-$aa_3$-$aa_4$-$aa_5$ (SEQ ID NO: 41) Formula I wherein X, $aa_1$, $aa_2$, $aa_3$-$aa_4$ and $aa_5$ are independently selected and wherein:

X is selected from $A_1P_2R_3Y_4$, $A_1A_2R_3Y_4$, $A_1P_2A_3Y_4$, $A_1P_2R_3A_4$, $P_2R_3Y_4$, $R_3Y_4$, $Z_3Y_4$, $R_3F_4$ and $Y_4$, wherein A, P, R, Y and F refer to their corresponding amino acids, the numbers refer to the positions of the amino acid in the $A_1P_2R_3Y_4$ sequence, and wherein Z is citrulline;

$A_1$ is selected from the group consisting of: alanine, leucine, valine, methionine, and φ, wherein φ defines an alpha-amino acid possessing a hydrophobic side-chain such as but not limited to: nor-leucine, iso-leucine, tert-leucine, cyclohexylalanine, allylglycine.

$P_2$ is selected from the group consisting of: proline, alanine, aminoisobutyric acid (Aib), N-Methyl-L-alanine (MeAla), trans-4-Hydroxyproline, diethylthiazolidine carboxylic acid (Dtc), and Ω, wherein Ω defines a conformational constraint-producing amino acid (Hanessian, S et al. 1997; Halab et al., 2000; Cluzeau and Lubell, 2004; Feng and Lubell 2001); non-limiting examples thereof include: azetidine-2-carboxylic acid, pipecolic acid, isonipecotic acid, 4-(aminomethyl)benzoic acid, 2-aminobenzoic acid, nipecotic acid.

$R_3$ is selected from the group consisting of: histidine, lysine, alanine, ornithine, citrulline, 2-pyridylalanine, 3-pyridylalanine, 4-pyridylalanine and arginine surrogates such as but not limited to 4-amidinophenylacetyl, 4-amidinophenylpropionyl, 4-amidinophenylglycyl, 4-amidinophenylmethylglycyl, 4-guanidinophenylacetyl, 4-uanidinophenylpropionyl, 4-guanidinophenylglycyl, 4-guanidinophenylmethylglycyl. (Masic and Kikelj, 2001; Feng and Lubell, 2001)

$Y_4$ is selected from the group consisting of: no residue, phenylalanine, tryptophan, alanine, and Σ, wherein Σ defines an alpha-amino acid possessing a hydrophobic side-chain Σ or aromatic side chain, examples include but are not limited to: nor-leucine, iso-leucine, tert-leucine, cyclohexylalanine, allylglycine, naphthylalanine, pyridylalanine, histidine, tyrosine.

$aa_1$ is selected from the group consisting of: threonine, serine, valine and η, wherein η defines a neutral hydrophilic amino acid, examples include but are not limited to, hydroxyvaline, beta,beta-dialkylserines, as described in Dettwiler and Lubell, 2004, homo-serine, allothreonine, hydroxyproline.

$aa_2$ is selected from the group consisting of: isoleucine, leucine, valine, proline, methionine, pipecolic acid, azetidine-2-carboxylic acid, hydroxyproline thiazolidine-a-carboxylic acid and φ, wherein φ defines an alpha-amino acid possessing a hydrophobic side-chain (see above).

$aa_3$ is selected from the group consisting of: aspartic acid, asparagine, glutamic acid, glutamine, serine, histidine, homoserine, beta-leucine, beta-phenylalanine, alpha amino adipic acid and Ψ, wherein Ψ defines a 3-amino-5-phenylpentanoic acid-alpha-amino acid possessing a hydrophobic side-chain, an aromatic amine, an aliphatic amine and a primary arylalkyl amine. Examples include but are not limited to benzylamine, phenylethylamine, 2,2-diphenylethylamine, 4-phenyl-benzylamine.

$aa_4$ is selected from: alanine, valine, isoleucine, leucine, methionine, phenylalanine, tryptophan and Λ, wherein Λ defines a neutral aliphatic amino acid. Examples include, but are not limited to, nor-leucine, iso-leucine, tert-leucine, cyclohexyalanine, allylglycine; an aliphatic amine of one to 10 carbons such as but not limited to methyl amine, iso-butylamine, iso-valerylamine, cyclohexilamine; an aromatic or arylalkylamine such as but not limited to aniline, naphtylamine, benzylamine, cinnamylamine, and phenylethylamine.

In another specific embodiment, the present invention relates to a peptide antagonist or derivative thereof, according to the present invention, wherein the antagonist is purified.

In yet another specific embodiment, the present invention relates to a peptide or derivative thereof, which antagonizes the biological activity of IL-1R, wherein the peptide or derivative thereof comprises the sequence characterized by one of the general formulas: $G_1$-X-$aa_1$-$aa_2$-$aa_3$-$aa_4$-$aa_5$- (SEQ ID NO: 42) Formula II -X-$aa_1$-$aa_2$-$aa_3$-$aa_4$-$aa_5$-$G_2$ (SEQ ID NO: 43) Formula III $G_1$-X-$aa_1$-$aa_2$-$aa_3$-$aa_4$-$aa_5$-$G_2$ (SEQ ID NO: 44) Formula IV wherein:

$G_1$ is attached to the amino-terminus of the peptide and is selected from the group consisting of: no residue, hydrogen, a straight chained or branched alkyl group of one to eight carbons, an acyl group (RCO) (such as acetyl, methyl, ethyl . . . ), propianoyl, butanoyl, iso-propianoyl, iso-butanoyl, or a tertiary amine (a dialkaylamino or monoalkylamino group).

$G_2$ is attached to the carboxy-terminus of the peptide and is selected from the group consisting of: no residue hydrogen, $NH_2$, an aliphatic amine of one to ten carbons (such as but not limited to methyl amine), iso-butylamine, iso-valerylamine, cyclohexylamine, an aromatic amine or arylalkyl amine (such as but not limited to aniline, naphthylamine, benzylamine, cinnamylamine, phenylethylamine), and or a tertiary amine (a dialkaylamino or monoalkylamino group).

In yet another embodiment of the present invention, the peptide or derivative thereof, which antagonizes the biological activity of IL-1R, has the sequence characterized by one of the general formulas defined by Formula I, Formula II, Formula III or Formula IV.

In yet a further embodiment of the present invention the IL-1R/RacP peptides or derivatives thereof, are relatively small molecules. In one embodiment, the peptides have a size between 5 and 25 amino acids, more particularly between 5 and 16 amino acids, more particularly between 5 and 10 amino acids, and even more particularly between 5 and 9 amino acids.

In another specific embodiment, the present invention relates to a peptidomimetic derived from formulas I and IV which antagonize the biological activity of IL-1R. In a more specific embodiment, the peptidomimetics of the present invention are defined by the structures represented in FIGS. 20 and 21.

In accordance with the present invention, there is provided a peptidomimetic antagonist of general sequence $R_1$-$aa_1$-$aa_2$-$aa_3$-$aa_4$-$aa_5$-$aa_6$-$aa_7$-$R_2$ (SEQ ID NO: 45) wherein $R_1$, $aa_1$, $aa_2$, $aa_3$, $aa_4$, $aa_5$, $aa_6$, $aa_7$, and $R_2$ are independently selected.

$R_1$ is selected from the group consisting of no residue, hydrogen, a straight chained or branched alkyl group of one to eight carbons, an acyl group (RCO—) wherein R is a straight chained or branched alkyl group of one to eight carbons. Non-limiting examples of R include, methyl, ethyl, propyl, butyl, pentyl, iso-propyl, and iso-butyl.

$aa_1$ is selected from the group consisting of no residue, arginine, lysine, ornithine, citrulline, an omega-amino acyl group of two to eight carbons, an omega guanidinyl acyl group of two to six carbons, an arginine surrogate, such as but not limited to 4-amidinophenylacetyl, 4-amidinophenylpropionyl, 4-amidinophenylglycyl, 4-amidinophenylmethylglycyl, 4-guanidinophenylacetyl, 4-uanidinophenylpropionyl, 4-guanidinophenylglycyl, 4-guanidinophenylmethylglycyl.

$aa_2$ is selected from the group consisting of no residue, tyrosine, phenylalanine, naphthylalanine, histidine, 4-hydroxyphenylglycine, tryptophan, phenylglycine, pyridylalanine, homoserine, 3,4-dihydroxyphenylalanine, and 4-chlorophenylalanine.

$aa_3$ is selected from the group consisting of no residue, threonine, serine, beta-hydroxyvaline, allo-threonine, valine, tert-butylleucine, leucine, proline, pipecolic acid, azetidine-2-carboxylic acid, hydroxyproline, and alanine.

$aa_4$ is selected from the group consisting of no residue, valine, proline, pipecolic acid, azetidine-2-carboxylic acid, hydroxyproline, thiazolidine-4-carboxylic acid, and 2,2-dimethylthiazolidine-4-carboxylic acid.

In another embodiment $aa_3$-$aa_4$ together may consist of 3-amino indolizidin-2-one 9-carboxylic acid, 3-amino pyrrolizidin-2-one 8-carboxylic acid, 3-amino quinolizidin-2-one 10-carboxylic acid, 8-amino indolizidin-9-one 2-carboxylic *acid*, a dipeptide surrogate or *beta-turn* mimic such as but not limited *to* examples reviewed in H*anessian* et *al.*

$aa_5$ is selected from the group consisting of no residue, alanine, glutamic acid, glutamine, aspartic acid, asparagine, histidine, homoserine, beta-leucine, beta-phenylalanine, and alpha-amino adipic acid.

$aa_6$ is selected from the group consisting of no residue, alanine, valine, leucine, phenylalanine, tryptophan, an aliphatic amine of one to ten carbons, such as but not limited to methyl amine, iso-butylamine, iso-valerylamine, cyclohexylamine, an aromatic or arylalkyl amine such as but not limited to aniline, naphthylamine, benzylamine, cinnamylamine, or phenylethylamine.

$aa_7$ is selected from the group consisting of no residue, alanine, valine, leucine, phenylalanine, tryptophan, an aliphatic amine of one to ten carbons, such as but not limited to methyl amine, iso-butylamine, iso-valerylamine, cyclohexylamine, an aromatic amine or arylalkyl amine such as but not limited to aniline, naphthylamine, benzylamine, cinnamylamine, or phenylethylamine.

$R_2$ is selected from the group consisting of no residue hydrogen, $NH_2$, an aliphatic amine of one to ten carbons such as but not limited to methyl amine, iso-butylamine, iso-valerylamine, cyclohexylamine, an aromatic amine and an arylalkyl amine such as but not limited to aniline, naphthylamine, benzylamine, cinnamylamine, phenylethylamine.

It should be noted that the stereochemical configurations of the chiral centers of the residues in the general sequence $R_1aa_1$-$aa_2$-$aa_3$-$aa_4$-$aa_5$-$aa_6$-$aa_7$-$R_2$ (SEQ ID NO: 45) can be of R- and S-, D- and L-configurations. In a preferred embodiment, the peptides consist of all D-isomers. Olefins can be of cis- and trans-geometry. Amino acid residues in the general sequence $R_1$-$aa_1aa_2$-$aa_3$-$aa_4$-$aa_5$-$aa_6$-$aa_7$-$R_2$ (SEQ ID NO: 45) can also be their aza-amino acid counterpart in which the chiral alpha-carbon is replaced by nitrogen such as but not limited to aza-alanine, aza-tyrosine, aza-phenylalanine.

Although the present invention is exemplified by the specific peptidomimetics of FIGS. 20 and 21, as well as those exemplified in FIGS. 26 to 30, the present invention is not so limited. Based on the disclosure herein, one skilled in the art can readily derive peptidomimetics having antagonistic activity toward the IL-1 receptor, identify further IL-1R/IL-1RacP receptor inhibiting compounds or improve those examplified herein. The peptidomimetics of the present invention are less susceptible to degradation by endogenous proteases and therefore have a longer half-life in vivo.

In one particular embodiment of the present invention, the peptidomimetic having antagonistic activity toward the IL-1 receptor are selected from the group consisting of TTI-101.140, TTI-101.141, TTI-101.125, TTI-101.110, TTI-101.111, TTI-101.136 and TTI-101.143. In a preferred embodiment the peptidomimetics are selected from the group consisting of TTI-101.140, TTI-101.141, TTI-101.125, and TTI-101.110.

The compounds of the present invention are useful in vitro as unique tools for understanding the biological role of IL-1 as well as the many factors thought to influence and be influenced by the production of IL-1 and its binding to the IL-1R/IL-1RacP receptor. The antagonists of the present invention are also useful in the development of other compounds that bind the IL-1 receptor because the peptide antagonists of the present invention provide important information on the relationship between structure and activity that will facilitate such development.

The antagonists of the present invention can also be used in assays as probes for determining the expression of IL-1R receptor on the surface of cells. Such assays may be useful, for example, for determining the degree of cellular inflammatory response to tissue infection or injury. Typically, the cells under study are exposed to the peptides or peptidomimetics of the present invention, so as to enable them to bind to the receptors present on the cell surface, and reacted cells are visualized (e.g., after wash, cell sorting, affinity chromatography, immunohistochemistry, autoradiography etc).

The compounds can be used as competitive inhibitors in assays to screen for, or to characterize similar new peptide receptors antagonists. In such assays, as well as assays for determining IL-1R expression, the peptides or peptidomimetics of the present invention can be used without modification or they can be labeled (i.e., covalently or non-covalently linked to a moiety which directly or indirectly provide a detectable signal). Examples of labels include radiolabels such as $^{125}I$, $^{14}C$, and $^3H$, enzymes such as alkaline phosphatase and horse radish peroxidase (U.S. Pat. No. 3,645, 090), ligands such as biotin, avidin, luminescent compounds including bioluminescent, phosphorescent, chemiluminescent or fluorescent labels (U.S. Pat. No. 3,940,475).

The compounds of the present invention can be administered to a subject to completely or partially inhibit the effects of IL-1α or IL-1β on the IL-1R response in vivo. Thus the methods of the present invention are useful in the therapeutic treatment of IL-1 related disorders. For example, the compositions of the present invention can be administered in a therapeutically effective amount to treat symptoms related to inappropriate production of IL-1 or inappropriate response to IL-1 (e.g., rheumatoid arthritis and inflammatory bowel disease).

In order to provide a clear and consistent understanding of terms used in the specification and claims, including the scope to be given such terms, a number of definitions are provided herein below.

Definitions

Unless defined otherwise, the scientific and technological terms and nomenclature used herein have the same meaning as commonly understood by a person of ordinary skill to which this invention pertains. Commonly understood definitions of molecular biology terms can be found for example in Dictionary of Microbiology and Molecular Biology, 2nd ed. (Singleton et al., 1994, John Wiley & Sons, New York, N.Y.), The Harper Collins Dictionary of Biology (Hale & Marham, 1991, Harper Perennial, New York, N.Y.), Rieger et al., Glossary of genetics: Classical and molecular, 5$^{th}$ edition, Springer-Verlag, New-York, 1991; Alberts et al., Molecular Biology of the Cell, 4$^{th}$ edition, Garland science, New-York, 2002; and, Lewin, Genes VII, Oxford University Press, New-York, 2000. Generally, the procedures of cell cultures, infection, molecular biology methods and the like are common methods used in the art. Such standard techniques can be found in reference manuals such as for example Sambrook et al. (2000, Molecular Cloning—A Laboratory Manual, Third Edition, Cold Spring Harbor Laboratories); and Ausubel et al. (1994, Current Protocols in Molecular Biology, John Wiley & Sons, New-York).

As used herein, the twenty natural amino acids and their abbreviations follow conventional usage. Stereoisomers (e.g., D-amino acids) such as □,□-disubstituted amino acids, N-alkyl amino acids, lactic acid and other unconventional amino acids may also be suitable components for the polypeptides of the present invention. Examples of unconventional amino acids include but are not limited to citrulline, ornithine, norvaline, 4-(E)-butenyl-4(R)-methyl-N-methylthreonine (MeBmt), N-methyl-leucine (MeLeu), aminoisobutyric acid, statine, N-methyl-alanine (MeAla).

The term aromatic amines as used herein is understood as being a molecule having a ring of 6 to 10 carbon atoms and examples include but are not limited to phenylmethylamine, phenylethylamine, phenylpropylamine and an amine comprising saturated or unsaturated hydrocarbon chain.

The term arylalkylamine as used herein is understood as being an amine comprising a saturated or unsaturated hydrocarbon chain. A primary arylalkylamine is composed of a ring of 6 to 10 carbon atoms and examples include but are not limited to phenyl, tolyl, alkoxyphenyl, alkoxycarbonylphenyl and halophenyl.

The term "aryl" as used herein, is understood as being phenyl, 1-naphthyl, and 2-naphthyl. The term "substituted aryl" as used herein, is understood as being phenyl, 1-naphthyl and 2-naphthyl having a substituent selected from the group consisting of phenyl, heteroaryl, lower alkyl, lower alkoxy, lower alkylthio, halo, hydroxy, trifluoromethyl, amino, —NH(lower alkyl), and —N(lower alkyl)$_2$, as well as being mono-, di- and tri-substituted phenyl, 1-naphthyl, and 2-naphthyl comprising substituents selected from the group consisting of methyl, methoxy, methylthio, halo, hydroxy, and amino.

The term "alkyl" as used herein, is understood as being straight or branched chain radicals having up to eight carbon atoms. The term "lower alkyl" as used herein, is understood as being straight or branched radicals having up to four carbon atoms and is a preferred sub-grouping for the term "alkyl".

The term "substituted alkyl" as used herein, is understood as being such straight or branched chain radicals having up to 8 carbon atoms wherein one or more, preferably one, two, or three hydrogen atoms have been replaced by a substituent selected from the group consisting of hydroxy, amino, cyano, halogen, trifluoromethyl, —NH(lower alkyl), —N(lower alkyl)$_2$, lower alkoxy, lower alkylthio, and carboxy, aryl and heteroaryl.

Unless otherwise noted "IL-1" refers to either or both IL-1α and IL-1β. The term "IL" refers to the broad family of interleukins.

As mentioned above, as used herein, the twenty naturally occurring L-amino acids and their abbreviations follows conventional usage. In the polypeptide notation used herein, the left-hand direction is the amino-terminal direction and the right-hand direction is the carboxy-terminal direction, in accordance with standard usage and convention. As used herein, the terms "peptides" and "polypeptides" refer to macromolecules which comprise a multiplicity of amino or imino acids (or their equivalents) in peptide linkage, wherein the polypeptides may comprise or lack posttranslational modifications. Therefore, the term peptides includes IL-1 receptor D-amino acid antagonists peptides and other modified forms of the peptides, so long as the modification does not alter its ability to modulate IL-1 receptor activity. All antagonist peptides of the present invention share the ability to modulate the activity of the IL-1 receptor. Non-limiting examples of modifications include N-terminal acetylation, glycosylation, and biotinylation. Particularly modified versions of the peptides according to the present invention are further described below.

The term "reverse-D peptide" refers herein to peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides may often retain the same tertiary conformation and therefore the same activity, as the L-amino acid peptides, but are more stable to enzymatic degradation in vitro and in vivo, and thus have greater therapeutic efficacy than the original peptide (Brady and Dodson 1994; Jameson et al. 1994).

As used herein, the designation "functional derivative" denotes, in the context of a functional derivative of an amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, provided that the biological activity of the protein is conserved (e.g. it acts as a non-competitive antagonist of IL-1 receptor). The substituting amino acid generally has chemico-physical properties, which are similar to that of the substituted amino acid. The similar chemico-physical properties include, similarities in charge, bulkiness, hydrophobicity, hydrophylicity and the like. The term "functional derivatives" is intended to include "segments", "variants", "analogs" or "chemical derivatives" of the subject matter of the present invention.

The terms "biological activity" or "IL-1R/IL-1RacP activity" or "receptor activity" refers to any detectable biological activity of IL-1 or IL-1R/IL-1RacP gene or protein. It can include specific biological activity of IL-1R/IL-1RacP proteins in cell signaling. This includes measurement of $PGE_2$ production, proliferation assays and changes in gene and protein expression (e.g., IL-6, IL-1, COX enzymes). However, IL-1R/IL-1RacP activities are not limited to these important biological activities. Biological activity also include for example, simple binding to the IL-1R receptor with compounds, substrates, interacting proteins and the like. For example, measuring the effect of a test compound on its ability to inhibit or increase (e.g., modulate) IL-1 response or IL-1R binding or interaction, is considered herein as measuring a biological activity of IL-1R according to the present invention. Broadly intra- or inter-molecular binding of the receptor subunits (e.g., IL-1R and IL-1RacP) in the absence vs the presence of the peptide, peptide derivative or peptidomimetic of the invention is yet another example of a biological activity according to the invention. IL-1R/IL-1RacP biological activity also includes any biochemical measurement of this receptor, conformational changes, phosphorylation status, any downstream effect of the receptor's signaling such as protein phosphorylation (or any other posttranslational modification e.g. ubiquitination, sumolylation, palmytoylation, prenylation etc), kinase effect or any other feature of the protein that can be measured with techniques known in the art. Finally, IL-1R/IL-1RacP biological activity include a detectable change in cell architecture, cell proliferation or other cell phenotype that is modulated by the action of a ligand (i.e., IL-1) on the predetermined receptor.

The term "variant" refers herein to a protein, which is substantially similar in structure and biological activity to the protein, to maintain at least one of its biological activities. Thus, provided that two molecules possess a common activity and can substitute for each other, they are considered variants as that term is used herein, even if the composition, or secondary, tertiary or quaternary structure of one molecule is not identical to that found in the other, or if the amino acid sequence or nucleotide sequence is not identical. While the present invention relates to peptide sequences and their derivatives and variants, it should be understood that nucleic acid sequences could be designed to express peptide antagonists of the present invention that consist of genetically encoded amino acids. Expression vectors, regulatory sequences (e.g. promoters), leader sequences and method to generate same and introduce them in cells are well known in the art. Thus, in one embodiment, such antagonist peptides of the present invention are expressed in cells by recombinant technology. In one embodiment the cells are prokaryotic cells and serve to produce and purify such peptides. In another embodiment the eukaryotic cells are specific eukaryotic cells in which IL-1 activity needs to be modulated.

The functional derivatives of the present invention can be synthesized chemically or produced through recombinant DNA technology. All of these methods are well known in the art.

The term "subject" or "patient" as used herein refers to an animal, preferably a mammal, most preferably a human who is the object of treatment, observation or experiment.

The terms "inhibiting," "reducing" or "prevention," or any variation of these terms, when used in the claims and/or the specification includes any measurable decrease or complete inhibition of the receptor activity to achieve a desired result. For example, a peptide is said to be inhibiting IL-1 activity when a decrease in $PGE_2$ production is measured following a treatment with the peptides, peptide derivatives or peptidomimetics of the present invention as compared to in the absence of these peptides.

As used herein, the term "purified" refers to a molecule (e.g. IL-1 receptor, peptides, peptide derivatives, peptidomimetics, nucleic acids, proteins etc.) having been separated from a component of the composition in which it was originally present. Thus, for example, a "purified IL-1 receptor" has been purified to a level not found in nature. A "substantially pure" molecule is a molecule that is lacking in most other components (e.g., 30, 40, 50, 60, 70, 75, 80, 85, 90, 95, 96, 97, 98, 99, 100% free of contaminants). By opposition, the term "crude" means molecules that have not been separated from the components of the original composition in which it was present. Therefore, the terms "separating" or "purifying" refers to methods by which one or more components of the biological sample are removed from one or more other components of the sample. Sample components include nucleic acids in a generally aqueous solution that may include other components, such as proteins, carbohydrates, or lipids. A separating or purifying step preferably removes at least about 70% (e.g., 70, 75, 80, 85, 90, 95, 96, 97, 98, 99, 100%), more preferably at least about 90% (e.g., 90, 91, 92, 93, 94, 95, 96, 97, 98, 99, 100%) and, even more preferably, at least about 95% (e.g., 95, 96, 97, 98, 99, 100%) of the other components present in the sample from the desired component. For the sake of brevity, the units (e.g. 66, 67 . . . 81, 82, . . . 91, 92% . . . ) have not systematically been recited but are considered, nevertheless, within the scope of the present invention.

The term "pharmaceutically acceptable carrier" refers to a carrier medium which does not interfere with the effectiveness of the biological activity of the active ingredients of the compound and which is not toxic for the host (e.g., patient) to whom it is administered.

"Therapeutically or pharmaceutically effective amount" refers herein to the amount of composition of the present invention sufficient to induce a desired effect. Such result can be alleviation or reduction of the signs, symptoms or causes of the disease or any other desired alteration of the target physiological system. For example, in the case of inflammatory diseases (e.g., arthritis and inflammatory bowel disease) a typical result will involve decrease in inflammatory and immunological responses.

As used herein, the terms "molecule", "compound", "agent" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non-limiting examples of molecules include peptides, antibodies, carbohydrates and pharmaceutical agents. The agents can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention or on the configuration of antagonist peptides and/or peptidomimetics of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modeling as mentioned above. Similarly, in a preferred embodiment, the polypeptides of the present invention are modified to enhance their stability. It should be understood that in most cases this modification should not alter the biological activity of the interaction domain. The molecules identified in accordance with the teachings of the present invention have a therapeutic value in diseases or conditions in which the physiology or homeostasis of the cell and/or tissue is compromised by a defect in IL-1 production or response. Non-limiting examples of such diseases or conditions include acute and chronic inflammatory diseases such as rheumatoid arthritis, inflammatory bowel disease (IBD), osteoarthritis, psoriasis, septic shock, encephalitis and respiratory distress syndrome. Alzheimer's disease, periventricular leukomalacia, meningitis, stroke, and a number of autoimmune diseases. It will be understood that the compounds are herein described interchangeably as "API-X" "TTI-X" or simply by the number of the compound (for example: "101.10", "API-101.10" or "TTI-101.10").

As used herein "antagonists", "peptide antagonists" or "IL-1R/IL-1RacP antagonists" refers to any molecule capable of inhibiting (completely or partially) a biological activity of IL-1 or IL-1R/IL-1RacP. The terms "antagonists", "peptide antagonists" or "IL-1R/IL-1RacP antagonists" also include potentiators of known compounds with antagonist properties.

Herein the terminologies "mimic", "mimetic", peptidomimetic" and the like are used herein interchangeably.

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "short peptide" is intended to mean a sequence of about 6-25 amino acids.

As used herein, the term "purified" refers to a compound or compounds having been separated from a component of the composition in which it was originally contained. Thus, for example, a "purified peptide" or a "purified composition of peptides" has been purified to a level not found in nature. A "substantially pure" compound is a compound that is lacking in most other components (e.g., 30, 40, 50, 60, 70, 75, 80, 85, 90, 95, 96, 97, 98, 99, 100% free of contaminants). By opposition, the term "crude" means compounds that have not been separated from the components of the original composition in which it was present. For the sake of brevity, the units (e.g. 66, 67 . . . 81, 82, . . . 91, 92% . . . ) have not been specifically recited but are considered nevertheless within the scope of the present invention.

An "isolated peptide" or "isolated compound" is purified from its natural in vivo state, or state in which it is present with other components at an earlier stage (from the synthesis for example).

It is contemplated that any embodiment discussed in this specification can be implemented with respect to any method or composition of the invention, and vice versa. Furthermore, compositions and kits of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

Having thus, generally described the invention, reference will be made to the accompanying drawings, showing by way of illustration only an illustrative embodiment thereof and in which.

Mean Blood Pressure (MBP) decrease in the presence of IL-1β and/or peptide 101.10. B) Modulation increase of serum $PGE_2$ synthesis in presence of IL-1β and peptide 101.10.

FIG. 13 shows the sequences of API-101.10 peptide derivatives designed for further optimization (SEQ ID NOS: 10 and 13-20).

Figure 14:
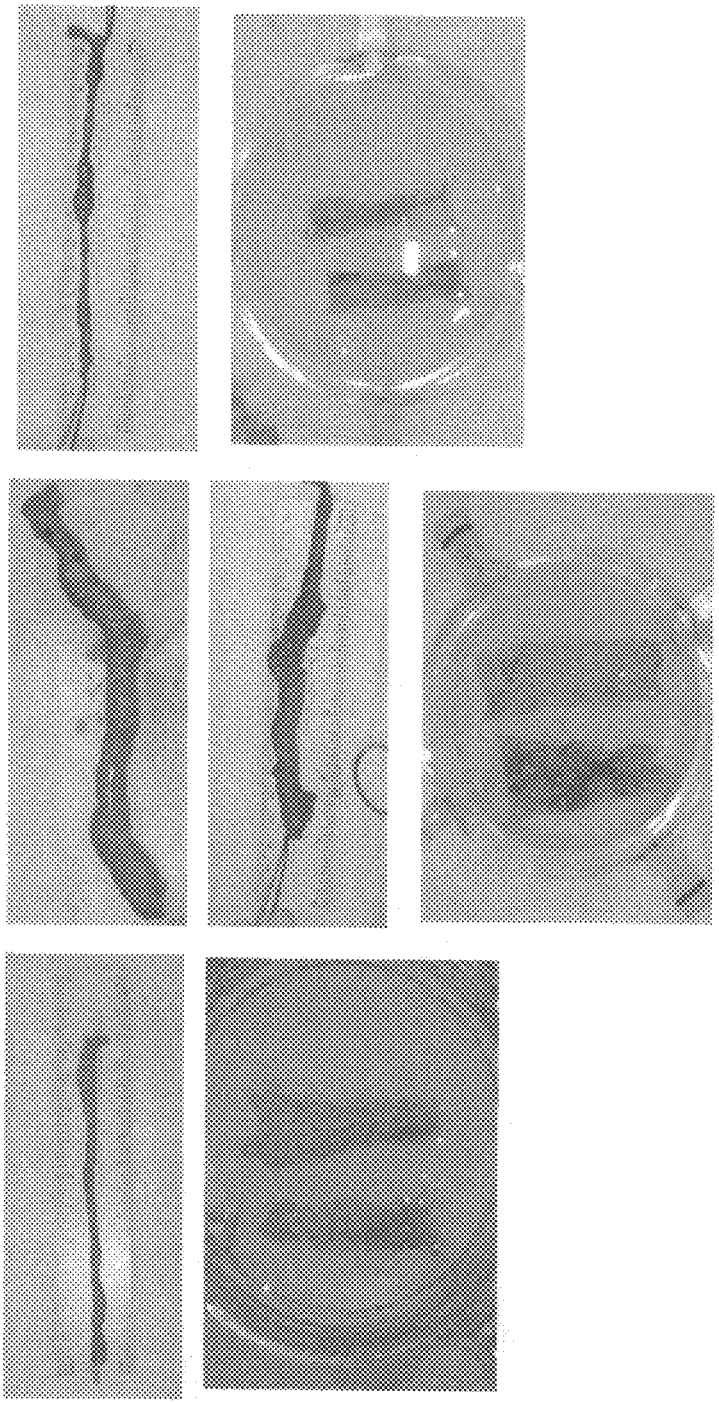

FIG. 14 shows the effect of API-101.10 peptide (systemic) in a rat model of Inflammatory Bowel Disease (macroscopy). (A) Saline, (B) TNBS+Saline, and (C), TNBS+API-101.10 (2.2 mg/kg/day).

FIG. 15 shows the characterization of 101.10 peptide derivatives (SEQ ID NOS: 10 and 13-20) by In vitro peptide inhibition ($IC_{50}$ and maximum efficiency (Emax) are shown) of IL-β induced PGE2 synthesis in microvessels endothelial cells and WI-38 human fibroblasts.

Figure 16:
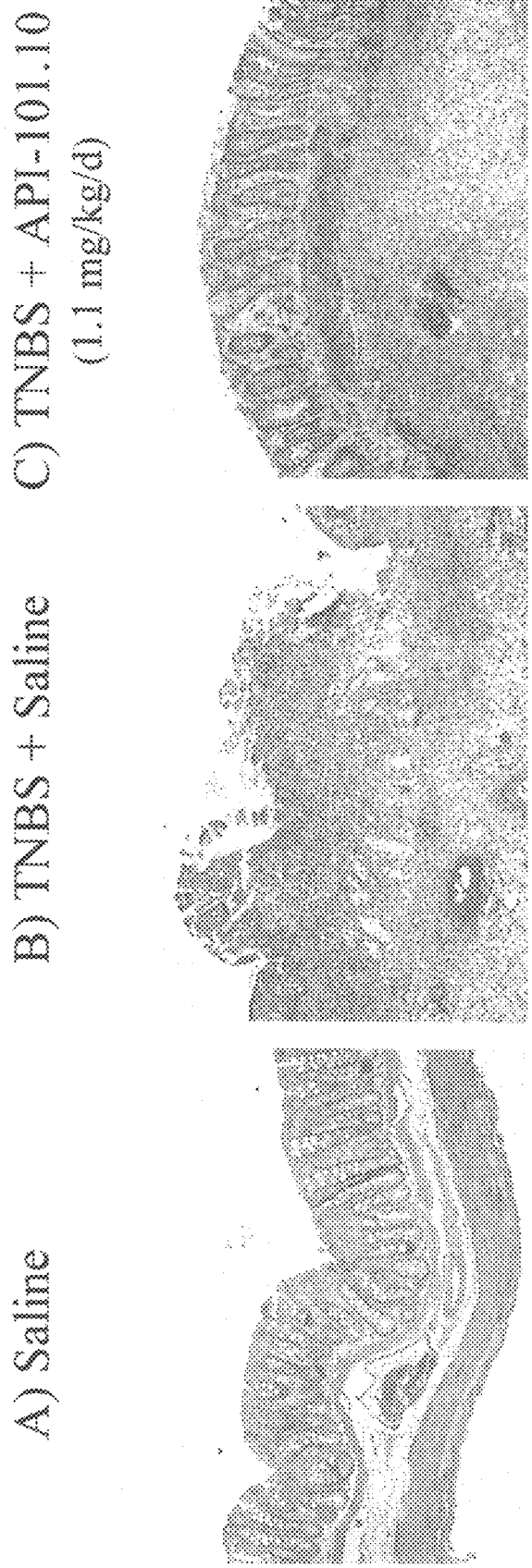

FIG. 16 shows the therapeutic effect of API-101.10 in a rat model of TNBS-induced inflammatory bowel disease (histology). (A) Saline, (B) TNBS (120 mg/ml)+Saline. (C) TNBS+API-101.10 (1.1 mg/kg/day).

FIG. 17 shows the characterization (inhibitory activity on IL-1β—induced $PGE_2$ production) of API 101 derivatives (SEQ ID NOS: 1-8) in porcine endothelial cells and chondrocytes.

FIG. 18 shows the characterization ($IC_{50}$ and maximum efficiency) of API-101 derivatives (SEQ ID NOS: 1 and 9-12).

Figure 19:
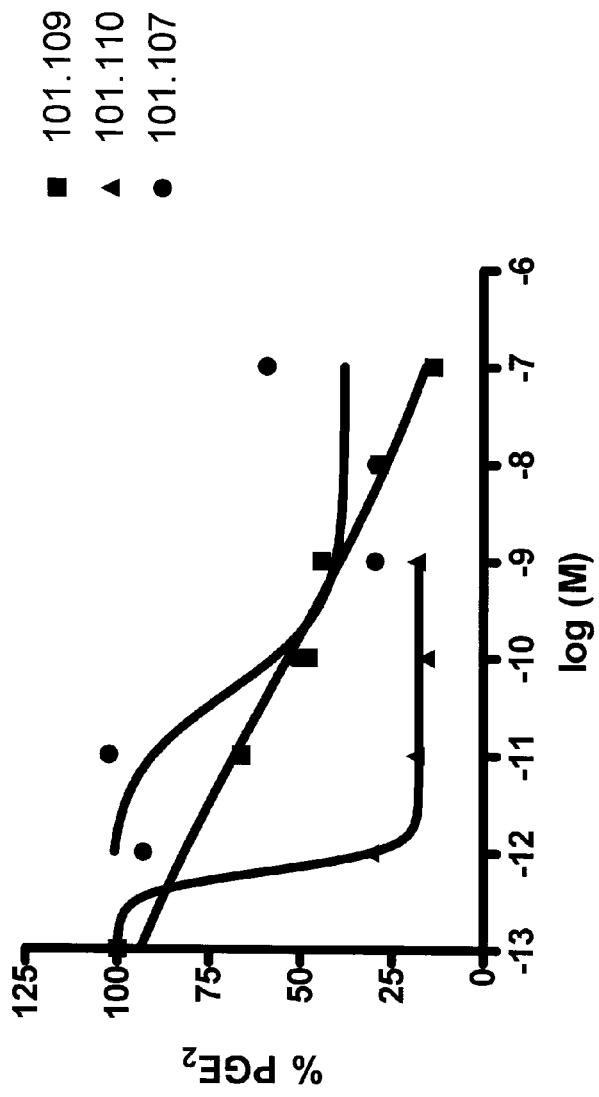

FIG. 19 shows dose response assays for IL-1-induced $PGE_2$ synthesis in porcine microvascular endothelial cells in the presence of various peptidomimetics.

Figure 20:
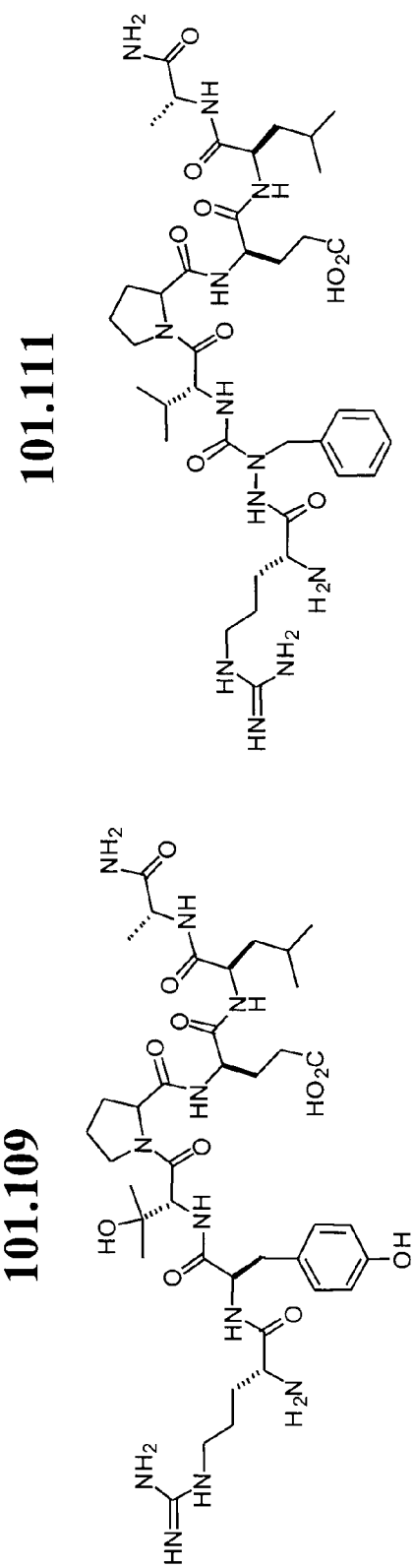

FIG. 20 shows the structure of the API-101.109 ("C2099", ry(HyVal)pela and API-1001-111 peptidomimetic.

Figure 21:
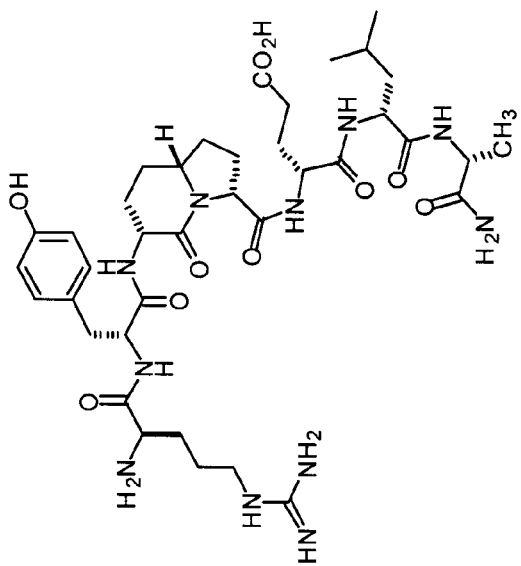

FIG. 21 shows the structure of the API-101.110 peptidomimetic.

Figure 22:
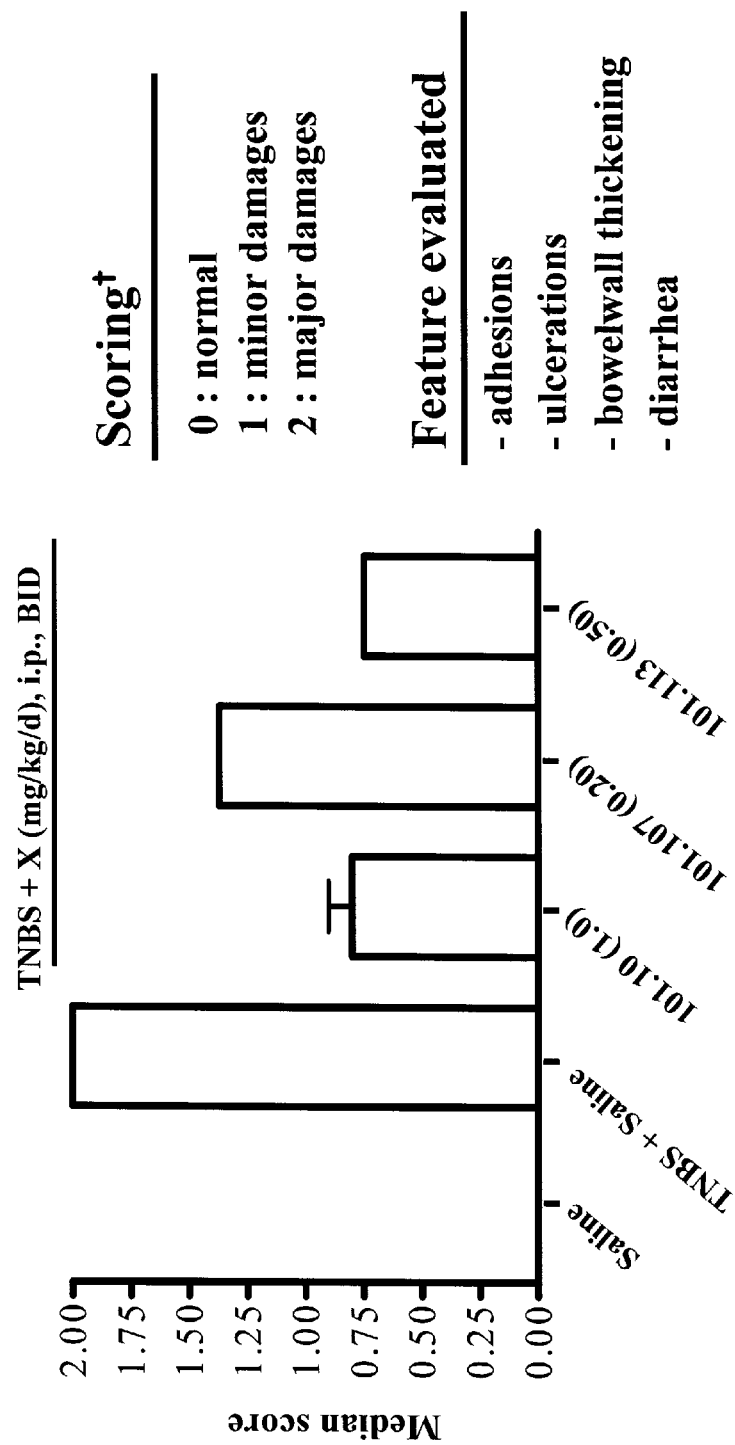

FIG. 22 shows the macroscopic evaluation of colonic injury in response to intraperitoneal injections of peptides 101.10, 101.107 and 101.113 in a rat model of Inflammatory Bowel Disease.

Figure 23:
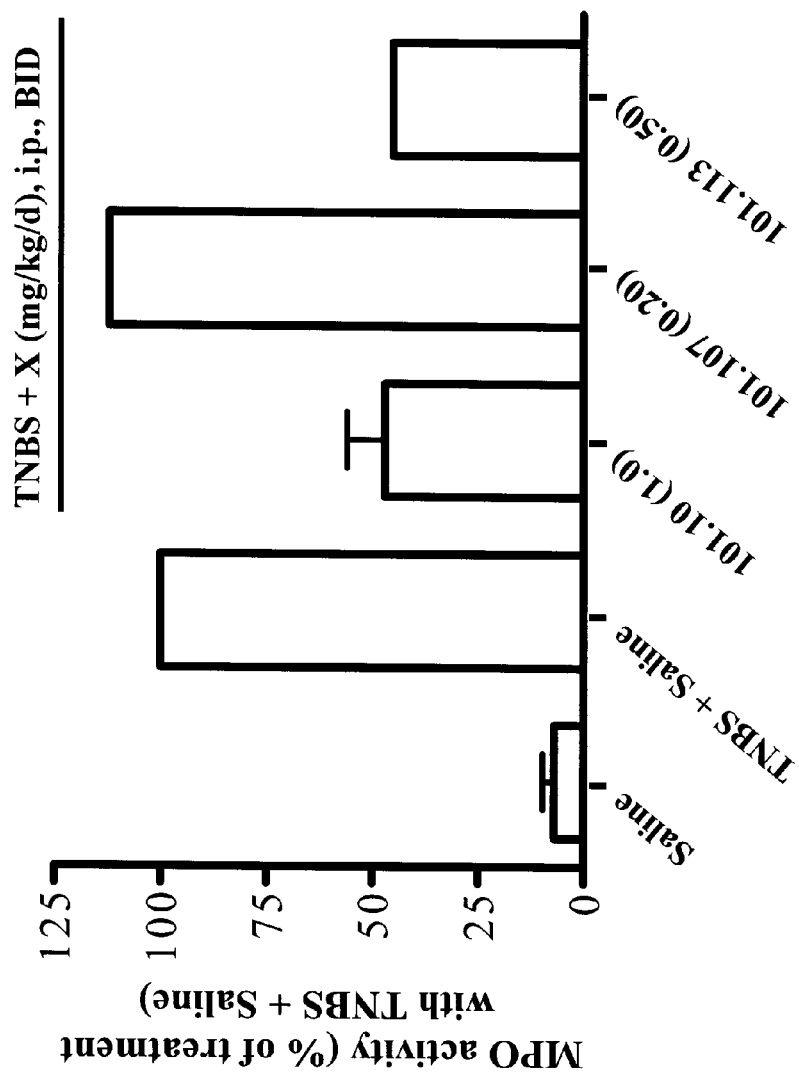

FIG. 23 shows the effect of intraperitonal injected peptides 101.10, 101.107 and 101.113 on tissue neutrophil infiltration (MPO assay) in a rat model of Inflammatory Bowel Disease (48:00).

Figure 24:
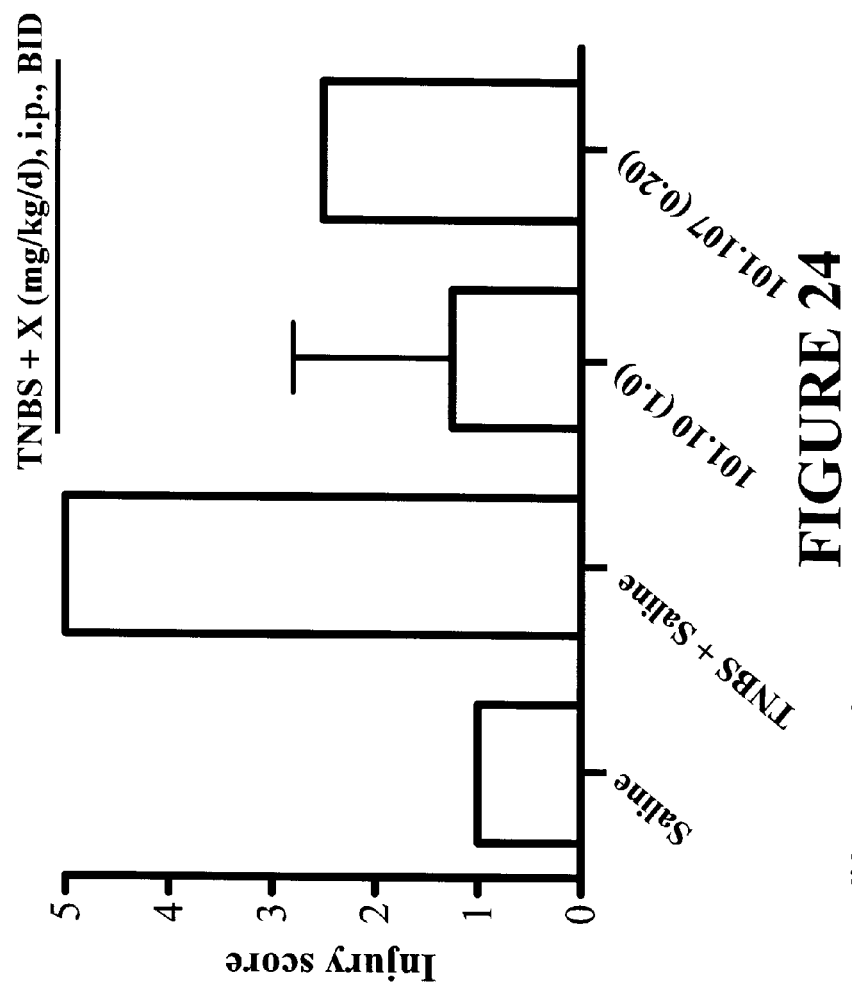

FIG. 24 shows the histological evaluation and scoring of tissue injury in response to intraperitoneal injections of peptides 101.10, 101.107 and 101.113 in a rat model of TNBS-induced Inflammatory Bowel Disease.

Figure 25:
Figure 25:
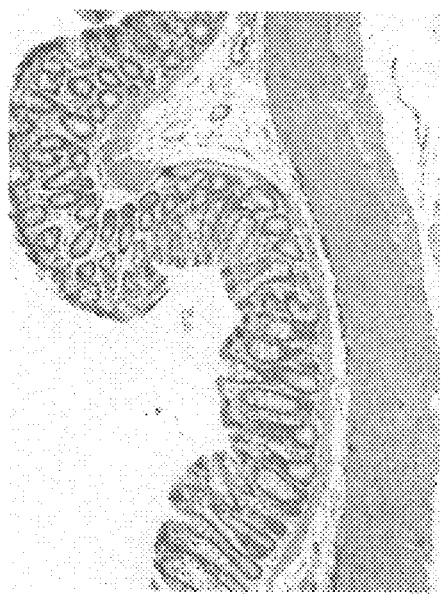
Figure 25:
Figure 25:
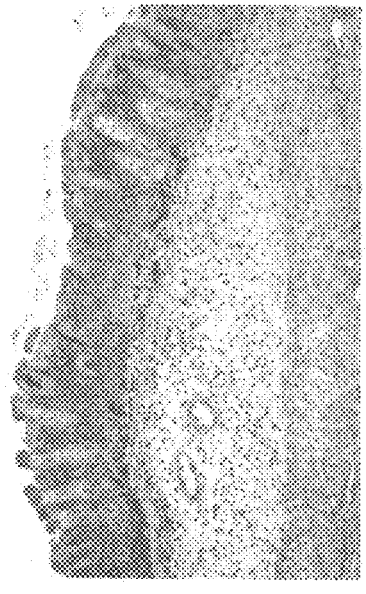

FIG. 25 shows the photographs of histological sections of colonic tissues treated with TNBS and TTI-101.10 and 101.107. Panel A) Control (not treated); B) Animals treated with TNBS; C) Animals treated with TNBS and intraperitonal injections of 101.10 (1.0 mg/kg/d) peptide; D) Animals treated with intraperitonal injections of 101.107 (0,2 mg/kg/d).

FIG. 26 shows the structures and results of the characterization of mimic derivatives of TTI-101.110

FIG. 27 shows the structures of mimic derivatives of TTI-101.125.

Figure 28:
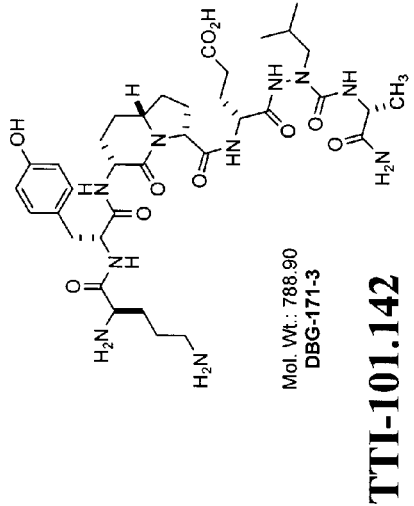
Figure 28:
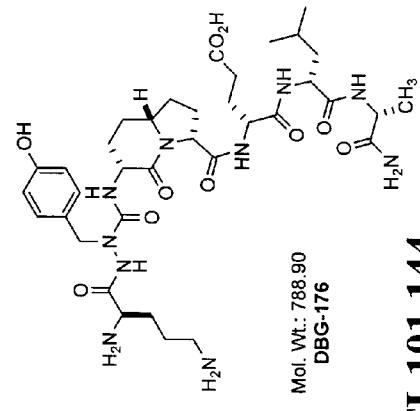
Figure 28:
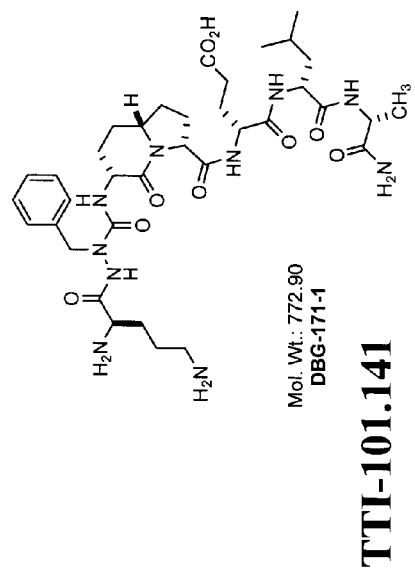
Figure 28:
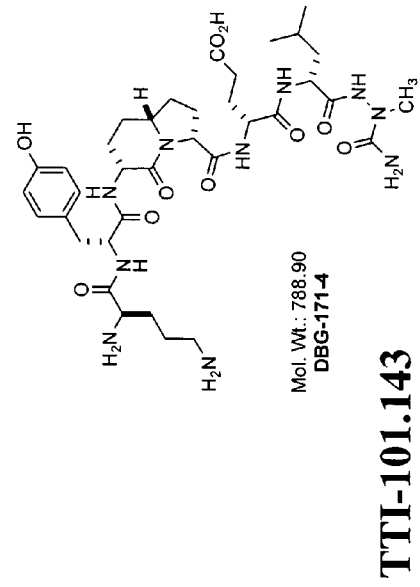

FIG. 28 shows the structures of other mimic derivatives of TTI-101.125.

FIG. 29 shows the structures and results of the characterization of mimic derivatives of TTI-101.125.

Figure 30:
Figure 30:
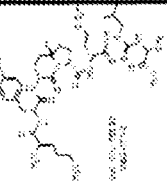
Figure 30:
Figure 30:
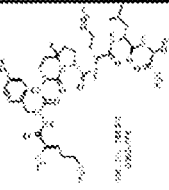
Figure 30:
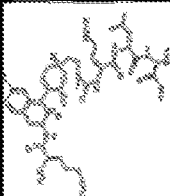

FIG. 30 shows the structures and results of the characterization of other mimic derivatives of TTI-101.125.

DESCRIPTION OF ILLUSTRATIVE EMBODIMENTS

One aim of the present invention is to describe a family of peptides and peptidomimetic compounds capable of inhibiting the biological function of IL-1 receptor accessory protein and therefore could be useful in numerous pathological conditions.

For purposes of clarity of disclosure, and not by way of limitation, the detailed description of the invention is divided into the following subsections:

I. Assays to identify peptides of the present invention
II. Peptide preparation
III. Peptide derivatives and peptidomimetics
IV. Assays to identify peptidomimetics
V. Pharmaceutical compositions
L Assays to Identify Peptides of the Present Invention Methods for testing the ability of candidate compounds to inhibit IL-1 receptor activity are presented herein. It will be understood that the invention is not so limited. Indeed, other assays well known in the art can be used in order to identify non-competitive, extracellular agonists or antagonists of the present invention.

Generally, screens of a IL-1R/IL-1RacP antagonist (i.e., candidate or test compounds or agents like peptides, peptidomimetics, small molecule or other drugs) may be based on assays which measure a biological activity of IL-1R/IL-1RacP. The assays of the present invention employ either a natural or recombinant IL-1 receptor. A cell fraction or cell free screening assays for antagonists of IL-1 activity can use in situ purified, or purified recombinant IL-1 receptor. Cell-based assays can employ cells which express IL-1 receptor naturally, or which contain recombinant IL-1 receptor. In all cases, the biological activity of IL-1 receptor can be directly or indirectly measured; thus inhibitors or activators of IL-1 receptor activity can be identified. The inhibitors or activators themselves may be further modified by standard combinatorial chemistry techniques to provide improved analogs of the originally identified compounds.

In one embodiment, an assay is a cell-based assay in which a cell which expresses a IL-1R/IL-1RacP receptor complex or biologically active portion thereof, either natural or recombinant in origin, is contacted with a test compound, and the ability of the test compound to modulate IL-1R/IL-1RacP receptor biological activity, e.g., modulation of $PGE_2$ production, proliferation assays, binding of IL-1R to a binding partner (IL-1RacP) or any other measurable biological activity of the IL-1 receptor is determined.

In an alternative embodiment, determining the ability of the test compound to modulate the activity of IL-1R/IL-1RacP receptor complex can be accomplished by determining the ability of the test compound to modulate the activity of a downstream effector of a IL-1R/IL-1RacP receptor target molecule. For example, the activity of the test compound on the effector molecule can be determined. Non-limiting examples of such downstream effector, include interleukin receptor activated kinase (IRAK); TRAF, activation of NI-KB (e.g. p65), mutagenic activated protein kinases (MAPK). Other examples of effector molecules which could be assayed to define the modulatory (agonist or antagonist) activity of the compounds of the present invention are described in Sims et al. 2002; and Kashiwamura et al. 2002.

In more than one embodiment of the above assay methods of the present invention, it may be desirable to immobilize either IL-1, IL-1R, IL-1RacP or an interacting peptide or peptidomimetic of the present invention to facilitate separation of complexed from uncomplexed forms of one or both of the interacting proteins, as well as to accommodate automation of the assay. Binding of a test compound to IL-1R protein or interaction of IL-1R protein with a target molecule (e.g., IL-1RacP) in the presence and absence of a candidate compound, can be accomplished in any vessel suitable for containing the reactants. Examples of such vessels include microtiter plates, test tubes and micro-centrifuge tubes. In one embodiment a fusion protein can be provided which adds a domain that allows one or both of the proteins to be bound to a matrix. For example. glutathione-S-transferase/IL-1R fusion proteins or glutathione-S-transferase/IL-1RacP fusion proteins can be adsorbed onto glutathione sepharose beads (Sigma Chemical, St. Louis, Mo.), or glutathione derivatized microtiter plates, which are then combined with the test compound or the test compound and either the non-adsorbed target protein or IL-1R protein and the mixture incubated under conditions conducive to complex formation (e.g. at physiological conditions for salt and pH). Following incubation the beads or microtiter plate wells are washed to remove any unbound components, and complex formation determined either directly or indirectly, for example, as described above. Alternatively, the complexes can be dissociated from the matrix, and the level of IL-1R binding or activity determined using standard techniques.

Other techniques for immobilizing proteins on matrices (which are well-known in the art) can also be used in the screening assays of the invention. For example, either a IL-1R protein or a IL-1R interacting molecule (e.g., IL-1, IL-1RacP) can be immobilized utilizing conjugation of biotin and streptavidin. Biotinylated IL-1R protein or IL-1R interacting molecule can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with IL-1R protein or IL-1R interacting molecule, but which do not interfere with binding of the IL-1R protein to its IL-1R interacting molecule, can be derivatized to the wells of the plate, and unbound target or IL-1R protein trapped in the wells by antibody conjugation. Methods for detecting such complexes, in addition to those described above for the GST-immobilized complexes, include immunodetection of complexes using antibodies reactive with the IL-1R protein or target molecule, as well as enzyme-linked assays which rely on detecting an enzymatic activity associated with IL-1R receptor or IL-1R interacting molecule.

It shall be understood that the in vivo experimental models such as described and exemplified herein can also be used to carry out an in vitro assay.

In Vitro Assays

In one embodiment, candidate peptides are tested for their ability to activate or inhibit IL-1 receptor's ability to modulate cellular proliferation with the incorporated tritiated thymidine method. In yet other embodiments, candidate peptides are tested for their ability to inhibit IL-1 receptor's ability to modulate cellular proliferation, using for example, the assays described in (Baker et al. 1995; Cheviron, Grillon et al. 1996); (Elliott et al. 1999; Hu et al. 1999).

In another embodiment, candidate peptides are tested for their ability to modulate the phosphorylation state of IL-1R or portion thereof, or an upstream or downstream target protein in the IL-1R/IL-1RacP pathway, using for example an in vitro kinase assay.

In other embodiments, candidate peptides targeting IL-1R are tested for $PGE_2$ levels, IL-6 or collagenase expression or any other molecule having a level which is modified following IL-1 stimulation in IL-1R/IL1RacP expressing cells, such as chondrocytes and fibroblasts.

In Vivo Assays

The assays described above may be used as initial or primary screens to detect promising lead compounds for further development. Lead peptides will be further assessed in additional, different screens. Therefore, this invention also includes secondary IL-1R screens that may involve various assays utilizing mammalian cell lines expressing these receptors or other assays.

Tertiary screens may involve the study of the identified inhibitors in animal models for clinical symptoms. Accordingly, it is within the scope of this invention to further use an agent (peptide or peptidomimetic) identified as described herein in an appropriate animal model such as a rat or a mouse. For example, a peptide can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment (e.g. treatments of different types of disorders associated with a deregulation or malfunction of IL-1 receptor), as described herein. Non-limiting animal models which can be used in such assays include: collagen-induced arthritis in rat, animal model of acute IBD, tumor growth in immunosuppressed mouse, sensitization of the airways in newborn mice and any other known animal model including transgenic animals.

II. Peptide Preparation

The peptide or peptide derivatives of the present invention are obtained by any method of peptide synthesis known to those skilled in the art, including synthetic (e.g., exclusive solid phase synthesis, partial solid phase synthesis, fragment condensation, classical solution synthesis) and recombinant techniques. For example, the peptides or peptide derivatives can be obtained by solid phase peptide synthesis, which in brief, consists of coupling the carboxyl group of the C-terminal amino acid to a resin (e.g., benzhydrylamine resin, chloromethylated resin, hydroxymethyl resin) and successively adding N-alpha protected amino acids. The protecting groups maybe any such groups known in the art. Before each new amino acid is added to the growing chain, the protecting group of the previous amino acid added to the chain is removed. Such solid phase synthesis has been described, for example, by Merrifield, 1964, J. Am. Chem. Soc. 85: 2149; Vale et al., 1981, Science, 213: 1394-1397, in U.S. Pat. Nos. 4,305,872 and 4,316,891, Bodonsky et al., 1966, Chem. Ind. (London), 38:1597; Pietta and Marshall, 1970, Chem. Comm. 650. The coupling of amino acids to appropriate resins is also well known in the art and has been described in U.S. Pat. No. 4,244,946. (Reviewed in Houver-Weyl, Methods of Organic Chemistry. Vol E22a. Synthesis of Peptides and peptidomimetics, Murray Goodman, Editor-in-Chief, Thieme. Stuttgart. New York 2002).

During any process of the preparation of the compound of the present invention, it may be necessary and/or desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (For Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

In one embodiment, the peptides of this invention, including the analogs and other modified variants, may generally be synthesized according to the FMOC protocol in an organic phase with protective groups. They can be purified with a yield of 70% with HPLC on a C18 column and eluted with an acetonitrile gradient of 10-60%. Their molecular weight can then be verified by mass spectrometry (Reviewed in Fields, G. B. "Solid-Phase Peptide Synthesis". Methods in Enzymology. Vol. 289, Academic Press, 1997).

Alternatively, peptides of this invention that consist of genetically encoded amino acids may be prepared in recombinant systems using polynucleotide sequences encoding the peptides. It is understood that a peptide of this invention may contain more than one of the above-described modifications within the same peptide. Also included in this invention are pharmaceutically acceptable salt complexes of the peptides of this invention or their derivatives.

Purification of the synthesized peptide or peptide derivatives is carried out by standard methods, including chromatography (e.g., ion exchange, size exclusion, affinity), centrifugation, precipitation or any standard technique for the purification of peptides and peptide derivatives. In one embodiment, thin-layered chromatography is employed. In another embodiment, reverse phase HPLC is employed. Other purification techniques well known in the art and suitable for peptide isolation and purification may be used in the present invention.

Where the processes for the preparation of the compounds according to the present invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques such as the formation of diastereoisomeric pairs by salt formation with an optically active acid followed by fractional crystallization and regeneration of the free base. The compounds may also be resolved by formation of diastereomeric esters or amides, followed by removal of the chiral auxiliary. Alternatively, the compounds may be resolved using chiral HPLC column.

III. Peptide Derivatives and Peptidomimetics

In addition to peptides consisting only of naturally occurring amino acids, peptidomimetics or peptide analogs are also encompassed by the present invention. Peptide analogs are commonly used in the pharmaceutical industry as non-peptide drugs with properties analogous to those of the template peptide. The types of non-peptide compounds are termed "peptide mimetics" or peptidomimetics (Fauchere, J. 1986, Adv. Drug Res. 15: 29; Evans et al., 1987, J. Med. Chem. 30: 1229). Peptide mimetics that are structurally related to therapeutically useful peptides may be used to produce an equivalent or enhanced therapeutic or prophylactic effect. Generally, peptidomimetics are structurally similar to paradigm polypeptide (i.e., a polypeptide that has a biological or pharmacological activity) such as naturally occurring receptor-binding polypeptides but have one or more peptide linkages optionally replaced by linkages like —$CH_2NH$—, —$CH_2S$—, —$CH_2$—, —$CH_2$, —CH=CH— (cis and trans), —$CH_2SO$—, —CH(OH)$CH_2$—, —$COCH_2$— etc., by methods well known in the art (Spatola A. F., Peptide Backbone Modifications, Vega Data, March 1983, 1(3): 267; Spatola et al., Life Sci., 1986, 38:1243-1249; Hudson D. et al., Int. J. Pept. Res. 1979, 14: 177-185; Weinstein. B., 1983, Chemistry and Biochemistry, of Amino Acids, Peptides and Proteins, Weinstein Eds, Marcel Dekker, New-York). Such peptide mimetics may have significant advantages over natural polypeptides including more economical production, greater chemical stability, enhanced pharmacological properties (e.g., half-life, absorption, potency, efficiency etc), reduced antigenicity and others.

While peptides are effective in inhibiting wild-type IL-1 in vitro, their effectiveness in vivo might be compromised by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al. 1993), In light of this, it is often advantageous to utilize modified versions of peptides also termed peptide analogs or derivatives. The modified peptides retain the structural characteristics of the original L-amino acid peptides that confer biological activity with regard to IL-1, but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide. In a preferred embodiment, the peptides consist of all D-amino acids. The presence of an N-terminal or C-terminal D-amino acid increases the in vivo stability of a peptide since peptidases cannot utilize a D-amino acid as a substrate (Powell et al. 1993). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same tertiary conformation and therefore the same activity, as the L-amino acid peptides, but are more stable to enzymatic degradation in vitro and in vivo, and thus have greater therapeutic efficacy than the original peptide (Brady and Dodson 1994; Jameson et al. 1994). In addition to reverse-D-peptide, constrained peptides comprising a consensus sequence or a substantially identical consensus sequence variation may be generated by methods well known in the art (Rizo et Gierasch, Ann. Rev. Biochem., 1992, 61: 387), for example, by adding cysteine residues capable of forming disulfide bridges which cyclize the peptide. Cyclic peptides have no free N- or C-termini. Thus, they are not susceptible to proteolysis by exopeptidases, although they are of course susceptible to endopeptidases, which do not cleave at peptide termini. Thus, the amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

A cyclic derivative containing intramolecular disulfide bond may be prepared by conventional solid phase synthesis while incorporating suitable S-protected cysteine or homocysteine residues at the positions selected for cyclization such as the amino and carboxy termini (SahM et al., 1996, J. Pharm. Pharmacol. 48: 197). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure; or (2) by removal of the peptide from the support along with complete side chain deprotection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S— alkyl bonds can be prepared by conventional solid phases while incorporating an amino acid residue with a suitable amino-protected side chain, and a suitable S-protected cysteine or homocysteine residue at the position selected for cyclization.

Substitution of unnatural amino acids for natural amino acids in a subsequence of the peptides can also confer resistance to proteolysis. Such a substitution can, for instance, confer resistance to proteolysis by exopeptidases acting on the N-terminus. Such substitutions have been described and these substitutions do not affect biological activity. Examples of non-naturally occurring amino acids include α,α-disubstituted amino acids, N-alkyl amino acids, lactic acids, C-α-methyl amino acids, and β-methyl amino acids. Amino acids analogs useful in the present invention may include but are not limited to β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with unnatural amino acids is routine and known in the art.

One other effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., 1993). Other chemical modifications which enhance serum stability include, but are not limited to, the addition of an N-terminal alkyl group, consisting of a lower alkyl of from 1 to 20 carbons, such as an acetyl group, and/or the addition of a C-terminal amide or substituted amide group. In particular the present invention includes modified peptides consisting of peptides bearing an N-terminal acetyl group and/or a C-terminal amide group.

Also included by the present invention are other types of peptide derivatives containing additional chemical moieties not normally part of the peptide, provided that the derivative retains the desired functional activity of the peptide. Examples of such derivatives include (i) N-acyl derivatives of the amino terminal or of another free amino group, wherein the acyl group may be an alkanoyl group (e.g., acetyl, hexanoyl, octanoyl), an aroyl group (e.g., benzoyl) or a blocking group such as F-moc (fluorenylmethyl-O—CO—); (ii) esters of the carboxy terminal or of another free carboxy or hydroxyl group; (iii) amide of the carboxyterminal or of another free carboxyl group produced by reaction with ammonia or with a suitable amine; (iv) phosphorylated derivatives; (v) derivatives conjugated to an antibody or other biological ligand and other types of derivatives.

Longer peptide sequences which result from the addition of extra amino acid residues to the peptides of the invention are encompassed by the present invention since they should have the same biological activity (inhibit activation of IL-1 receptor) as the peptides described above. While peptides having a substantial number of additional amino acids are not excluded, it will be recognized that some large polypeptides may assume a configuration that masks the effective sequence, thereby preventing binding to IL-1R. These derivatives could act as competitive antagonists and are thereby excluded from the invention. Thus, while the present invention encompasses peptides or derivatives having an extension, such longer peptides should be selected as not destroying the modulating activity of the peptide or derivative.

Other derivatives included in the present invention are dual peptides consisting of two of the same, or two different peptides of the present invention covalently linked to one another either directly or through a spacer, such as by a short stretch of alanine residues or by a putative site for proteolysis (e.g., by cathepsin, see U.S. Pat. No. 5,126,249 and European Patent No. 495,049). Multimers of the peptides of the present invention consist of polymer of molecules formed from the same or different peptides or derivatives thereof.

In another embodiment, the peptide derivatives of the present invention are chimeric or fusion proteins comprising a peptide of the present invention or fragment thereof linked at its amino or carboxy terminal end, or both, to an amino acid sequence of a different protein. Such a chimeric or fusion protein may be produced by recombinant expression of a nucleic acid encoding the protein. In one embodiment such a chimeric or fusion protein contains at least 6 amino acids of a peptide of the present invention and has a functional activity equivalent or greater to that of a peptide of the invention.

Peptide derivatives of the present invention can be made by altering the amino acid sequences by substitutions, additions or deletions that provide for functionally equivalent molecules, or functionally enhanced or diminished molecules, as desired. The derivative of the present invention include, but are not limited to those containing, as primary amino acid sequence, all or part of the amino acid sequence of the peptides of the present invention including altered sequences in which functionally equivalent amino acid residues are substituted for an equivalent in the sequence. For example, one or more amino acid residues within the sequence can be substituted by another amino acid of a similar polarity, which act as a functional equivalent, resulting in a silent alteration. Substitution for an amino acid within the sequence may be selected from other members of the class to which the amino acid belongs. For example, the positively charged (basic) amino acids include, arginine, lysine and histidine. The nonpolar (hydrophobic) amino acids include, leucine, isoleucine, alanine, phenylalanine, valine, proline, tryptophan and methionine. The uncharged polar amino acids include serine, threonine, cysteine, tyrosine, asparagine and glutamine. The negatively charged (acid) amino acids include glutamic acid and aspartic acid. The amino acid glycine is sometimes included in the nonpolar amino acids family and sometimes in the uncharged (neutral) polar amino acids family. Substitutions that are done within a family of amino acids are generally understood to be conservative substitutions.

In one particular embodiment of the present invention the antagonist peptide comprises the sequence TTI-101.140, TTI-101.141, TTI-101.125, TTI-101.110, TTI-101.111, TTI-101.136 and TTI-101.143.

IV. Assays to Identify Peptidomimetics

As mentioned above, non-peptidyl compounds generated to replicate the backbone geometry and pharmacophore display (peptidomimetics) of the peptides identified by the methods of the present invention often possess attributes of greater metabolic stability, higher potency, longer duration of action and better bioavailability.

The peptidomimetic compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, Anticancer Drug Des. 12: 145, 1997). Examples of methods for the synthesis of molecular libraries can be found in the art, for example in: DeWitt et al. (1993) Proc. Natl. Acad. Sci. USA. 90:6909; Erb et al. (1994) Proc. Natl. Acad. Sci. USA 91:11422; Zuckermann et al. (1994), J. Med. Chem. 37:2678; Cho et al. (1993) Science 261: 1303; Carell et al. (1994) Angew. Chem, Int. Ed Engl. 33:2059; and ibid 2061; and in Gallop et al. (1994) Med. Chem. 37:1233. Libraries of compounds may be presented in solution (e.g. Houghten (1992) Biotechniques 13:412-421) or on beads (Lam (1991) Nature 354; 82-84), chips (Fodor (1993) Nature 364; 555-556), bacteria or spores (Ladner U.S. Pat. No. 5,223,409), plasmids (Cull et al., (1992) Proc. Natl. Acad. Sci. USA 89:1865-1869) or on phage (Scott and Smith (1990); Science 249:386-390). Examples of methods for the synthesis of molecular libraries can be found in the art, for example in: DeWitt et al. (1993) supra; Erb et al. (1994) supra; Zuckerman et al. (1994) supra; Cho et al. (1993) supra; Carrell et al. (1994) Supra, or luciferase, and the enzymatic label detected by determination of conversion of an appropriate substrate to product.

Once a peptide of the present invention is identified, it may be isolated and purified by any number of standard methods including but not limited to differential solubility (i.e., precipitation), centrifugation, chromatography (affinity, ion exchange, size exclusion and the like) or by any other standard techniques used for the purification of peptides, peptidomimetics or proteins. The functional properties of an identified peptide of interest may be evaluated using any functional assay known in the art. In one embodiment assays for evaluating downstream receptor function in intracellular signaling are used (e.g., $PGE_2$ synthesis).

In one embodiment, the peptidomimetic compounds of the present invention are obtained with the following three-phase process: 1) scanning the peptides of the present invention to identify regions of secondary structure necessary for recognition and activity toward the IL-1 receptor; 2) using conformationally constrained dipeptide surrogates to refine the backbone geometry and provide organic platforms corresponding to these surrogates; and 3) using the best organic platforms to display organic pharmocophores in libraries of candidates designed to mimic the desired activity of the native peptide. In more details the three phases are as follows. In phase 1, the peptide leads are scanned and their structure abridged to identify the requirements for their activity. A series of peptide analogs of the original are synthesized. In phase 2, the best peptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best peptide candidates. These and related plateforms (Reviewed in Halab, Li; Gosselin, F; Lubell, W D; Biopolymers (Peptide Science) Vol 55, 101-122. 2000; Hanessian, S. J. McNaughton-Smith G; Lombart, H-G.; Lubell, W. D. Tetrahedron Vol. 53, 12789-12854, 1997) may be introduced at specific regions of the peptide in order to orient the pharmacophores in different directions. Biological evaluation of these analogs identifies improved leads that mimic the geometric requirements for activity. In phase 3, the platforms from the most active leads are used to display organic surrogates of the pharmacophores responsible for activity of the native peptide. The pharmacophores and scaffolds are combined in a parallel synthesis format. Of course derivation of peptides and the different phases therefore, can be done by other means and methods known in the art.

Structure function relationships determined from the peptides, peptide derivatives, peptidomimetics or other small molecules of the present invention may be used to refine and prepare analogous molecular structures having similar or better properties. Thus, also within the scope of the present invention are molecules, in addition to those specifically disclosed, that share the structure, polarity, charge characteristics and side chain properties of the specific embodiments exemplified herein.

In conclusion, the peptides, peptide derivatives, peptidomimetics or other small molecules of the present invention are functionally active (i.e., capable of exhibiting one or more of the identified functional activities associated with a peptide of the present invention). For example, such peptides, peptide derivatives, peptidomimetics or analogs that inhibit a desired property (e.g., binding of the IL-1RacP to a protein partner or ligand) can be used as inhibitors of such property and its physiological correlates. Peptides, derivatives, peptidomimetics or analogs of the peptides of the present invention can be tested for the inhibition of cell signaling through the IL-1R/IL-1RacP receptor by any functional assay known in the art (e.g., $PGE_2$ synthesis).

V. Pharmaceutical Compositions

The present invention relates to a method for inhibiting IL-1 receptor activity through its interaction with the peptides, peptide derivatives and peptidomimetics of the present invention. In view of the importance of IL-1 and or IL-1R/IL1RacP receptor function in numerous pathways and conditions in animals, the peptides, peptide derivatives and peptidomimetics of the present invention are useful in the treatment of conditions or diseases associated with IL-1 response (e.g., IL-1 overexpression or abnormal signaling through IL-1R/IL1-RacP).

Therefore, methods of the present invention comprise administering to a subject in need thereof or at risk of being in need thereof an effective amount of a peptide, peptide derivative or peptidomimetic, or a composition comprising a peptide, peptide derivative or peptidomimetic to a subject, to inhibit IL-1R/RacP biological activity. In one embodiment, an effective amount of a therapeutic composition comprising a peptide or peptide derivative thereof and a suitable pharmaceutical carrier is administered to a subject to inhibit IL-1R/IL-1RacP biological activity to prevent, ameliorate symptoms or treat a disorder, disease or condition related to abnormal signaling through IL-1R/IL-1RacP (e.g., overestimulation of the IL-1/IL-1RacP receptor via an overproduction of IL-1/IL-1RacP ligand or via a constitutively active receptor or any other defect). In one embodiment, the subject is an animal. In another embodiment, the subject is a mammal, and preferably a human.

The peptides, peptide derivatives and peptidomimetics of the present invention are used in the treatment, prophylaxis or amelioration of symptoms in any disease condition or disorder where the inhibition of IL-1R/IL-1RacP biological activity might be beneficial. Diseases, conditions or disorders to which the peptides, peptide derivatives or peptidomimetics of the present invention may be beneficial include, but are not limited to the following examples: chronic and acute inflammation diseases like rheumatoid arthritis, inflammatory bowel disease, septic shock, osteoarthritis, psoriasis, encephalitis, glomerulonephritis, respiratory distress syndrome and Reiter's syndrome. Other conditions include, systemic lupus erythematosus, scleroderma, Crohn's disease, ulcerative colitis, inflammatory joint disease, cachexia in certain leukemias, Alzheimer's disease, numerous types of cancers, juvenile diabetes mellitus, pulmonary hypertension, stroke, periventricular leucopenia and meningitis.

Composition within the scope of the present invention should contain the active agent (e.g. peptide, peptide derivative or peptidomimetic) in an amount effective to achieve the desired therapeutic effect while avoiding adverse side effects. Pharmaceutically acceptable preparations and salts of the active agent are within the scope of the present invention and are well known in the art. For the administration of polypeptide antagonists and the like, the amount administered should be chosen so as to avoid adverse side effects. The amount of the therapeutic or pharmaceutical composition which is effective in the treatment of a particular disease, disorder or condition will depend on the nature and severity of the disease, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 100 mg/kg/day will be administered to the subject. Effective doses may be extrapolated from dose response curves derived from in vitro or animal model test systems. For example, in order to obtain an effective mg/kg dose for humans based on data generated from rat studies, the effective mg/kg dosage in rat is divided by six.

Various delivery systems are known and can be used to administer peptides, peptide derivatives or peptidomimetics or a pharmaceutical composition of the present invention. The pharmaceutical composition of the present invention can be administered by any suitable route including, intravenous or intramuscular injection, intraventricular or intrathecal injection (for central nervous system administration), orally, topically, subcutaneously, subconjunctivally, or via intranasal, intradermal, sublingual, vaginal, rectal or epidural routes.

Other delivery system well known in the art can be used for delivery of the pharmaceutical compositions of the present invention, for example via aqueous solutions, encapsulation in microparticles, or microcapsules.

In yet another embodiment, the pharmaceutical compositions of the present invention can be delivered in a controlled release system. In one embodiment polymeric materials can be used (see Smolen and Ball, Controlled Drug Bioavailability, Drug product design and performance, 1984, John Wiley & Sons; Ranade and Hollinger, Drug Delivery Systems, pharmacology and toxicology series, 2003, $2^{nd}$ edition, CRRC Press), in another embodiment, a pump may be used (Saudek et al., 1989, N. Engl. J. Med. 321: 574).

Compounds of the present invention may also be delivered by the use of monoclonal antibodies as individual carriers to which the compound molecules are coupled. The compounds of the present invention may also be coupled to a class of biodegradable polymers useful in achieving controlled release of the drug, non-limiting examples, include: polylactic acid, polyorthoesters, cross-linked amphipathic block copolymers and hydrogels, polyhydroxy butyric acid and polydihydropyrans.

As mentioned above, pharmaceutical compositions of the present invention comprise a peptide, peptide derivative or peptidomimetic combined with a pharmaceutically acceptable carrier. The term carrier refers to diluents, adjuvants, excipients such as a filler or a binder, a disintegrating agent, a lubricant a silica flow conditioner a stabilizing agent or vehicles with which the peptide, peptide derivative or peptidomimetic is administered. Such pharmaceutical carriers include sterile liquids such as water and oils including mineral oil, vegetable oil (e.g., peanut oil, soybean oil, sesame oil, canola oil), animal oil or oil of synthetic origin. Aqueous glycerol and dextrose solutions as well as saline solutions may also be employed as liquid carriers of the pharmaceutical compositions of the present invention. Of course, the choice of the carrier depends on the nature of the peptide, peptide derivative or peptidomimetic, its solubility and other physiological properties as well as the target site of delivery and application. For example, carriers that can penetrate the blood brain barrier are used for treatment, prophylaxis or amelioration of symptoms of diseases or conditions (e.g. inflammation) in the central nervous system. Examples of suitable pharmaceutical carriers are described in Remington: The Science and Practice of Pharmacy by Alfonso R. Gennaro, 2003, $21^{th}$ edition, Mack Publishing Company.

Further pharmaceutically suitable materials that may be incorporated in pharmaceutical preparations of the present invention include absorption enhancers, pH regulators and buffers, osmolarity adjusters, preservatives, stabilizers, antioxidants, surfactants, thickeners, emollient, dispersing agents, flavoring agents, coloring agents and wetting agents.

Examples of suitable pharmaceutical excipients include, water glucose, sucrose, lactose, glycol, ethanol, glycerol monostearate, gelatin, rice, starch flour, chalk, sodium stearate, malt, sodium chloride and the like. The pharmaceutical compositions of the present invention can take the form of solutions, capsules, tablets, creams, gels, powders sustained release formulations and the like. The composition can be formulated as a suppository, with traditional binders and carriers such as triglycerides (see Remington: The Science and Practice of Pharmacy by Alfonso R. Gennaro, 2003, $21^{th}$ edition, Mack Publishing Company). Such compositions contain a therapeutically effective amount of the therapeutic composition, together with a suitable amount of carrier so as to provide the form for proper administration to the subject. The formulations are designed so as to suit the mode of administration and the target site of action (e.g., a particular organ or cell type).

The pharmaceutical compositions of the present invention can be formulated as neutral or salt forms. Pharmaceutically acceptable salts include those that form with free amino groups and those that react with free carboxyl groups. Non-toxic alkali metal, alkaline earth metal and ammonium salts commonly used in the pharmaceutical industry include sodium, potassium, lithium, calcium, magnesium, barium, ammonium, and protamine zinc salts, which are prepared by methods well known in the art. The term also includes non-toxic acid addition salts, which are generally prepared by reacting the compounds of the present invention with suitable organic or inorganic acid. Representative salts include the hydrobromide, hydrochloride, valerate, oxalate, oleate, laureate, borate, benzoate, sulfate, bisulfate, acetate, phosphate, tysolate, citrate, maleate, fumarate, tartrate, succinate, napsylate salts and the like.

Examples of fillers or binders that may be used in accordance with the present invention include acacia, alginic acid, calcium phosphate (dibasic), carboxymethylcellulose, carboxymethylcellulose sodium, hydroxyethylcellulose, hydroxypropylcellulose, hydroxypropylmethylcellulose, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Another most preferred filler or binder consists of microcrystalline cellulose.

Examples of disintegrating agents that may be used include alginic acid, carboxymethylcellulose, carboxymethylcellulose sodium, hydroxypropylcellulose (low substituted), microcrystalline cellulose, powdered cellulose, colloidal silicon dioxide, sodium croscarmellose, crospovidone, methylcellulose, polacrilin potassium, povidone, sodium alginate, sodium starch glycolate, starch, disodium disulfite, disodium edathamil, disodium edetate, disodiumethylenediaminetetraacetate (EDTA) crosslinked polyvinylpyrollidines, pregelatinized starch, carboxymethyl starch, sodium carboxymethyl starch, microcrystalline cellulose.

Examples of lubricants include calcium stearate, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL leucine.

Examples of silica flow conditioners include colloidal silicon dioxide, magnesium aluminum silicate and guar gum. Another most preferred silica flow conditioner consists of silicon dioxide.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

The present invention also provides for modifications of peptides or peptide derivatives such that they are more stable once administered to a subject (i.e., once administered it has a longer half-life or longer period of effectiveness as compared to the unmodified form). Such modifications are well known to those skilled in the art to which this invention pertain (e.g., polyethylene glycol derivatization a.k.a. PEGylation, microencapsulation, etc).

The IL-1R/IL-1RacP antagonists of the present invention may be administered alone or in combination with other active agents useful for the treatment, prophylaxis or amelioration of symptoms of a IL-1, IL-1R/IL-1RacP associated disease or condition. Thus, the compositions and methods of the present invention can be used in combination with other agents exhibiting the ability to modulate IL-1 activity (e.g., synthesis, release and/or binding to IL-1R/IL-1RacP) or to reduce the symptoms of an IL-1 associated disease (e.g., rheumatoid arthritis and inflammatory bowel disease). Example of such agents include but are not limited to antirheumatic drugs such as chloroquine, auranofin (Ridaura™), dexamethasone, sodium aurothiomalate, methotrexate (see Lee et al., 1988, Proc. Int. Acad. Sci, 85:1204), probucol (see Ku et al., 1988, Am. J. Cardiol. 62:778), pentoxyfylline (e.g., Sullivan et al., 1988, Infect. Immun. 56:1722), disulfiram (see Marx 1988, Science, 239:257), antioxidants such as nordihydroguaiaretic acid (lee et al., 1988, Int J. Immunopharm., 10:385), IL-1 Trap (see e.g., 2003, Curr. Opin. Inv. Drugs, 4(5): 593-597), Anakinra (Kineret™, PCT Application WO00236152), leflunomide, corticosteroids (Medrol™, Deltasone™, Orasone™) as well as other agents such as those described in Bender and Lee (1989) Annual Reports in Medicinal Chemistry, chapter 20: Pharmacological Modulation of IL-1: 185-193). Other drugs may also be used in combination with the compounds of the present invention like anti-inflammatory drugs such as Non Steroidal Antiinflammatory Drugs (NSAIDS, e.g., Rofecoxib (VIOXX™), Celecoxib (Celebrex™), Valdecoxib (Bextra™), Aspirin™, advil™), anti TNF-α drugs (Infliximab, etanercept, adalimumab), collagenase inhibitors and others. Of course a combination of two or more peptides, derivatives and peptide mimetics and their combination with one or more drug can also be used, in all combinations (e.g. one or more peptide with one or more mimetic, one or more mimetic with one or more derivative, one ore more peptide with one or more drug etc.).

The present invention is illustrated in further details by the following non-limiting examples. The examples are provided for illustration only and should not be construed as limiting the scope of the invention.

EXAMPLE 1

Effect of API-101 Peptide

One example of the efficacy of the compounds and methods of the present invention is represented by the results obtained with the identified peptide API-101 (SEQ ID NO 1: APRYTVELA).

All peptides described in the following examples have been synthesized according to the FMOC protocol of solid phase synthesis in an organic phase with protective groups. They have been purified with a yield of 70% with HPLC on a C18 column and eluted with an acetonitrile gradient of 10-60%. Their molecular weight have been verified by mass spectrometry. Of course as alluded above, when natural amino acids are used, they can be obtained by genetic engineering techniques as known in the art.

Figure 1:
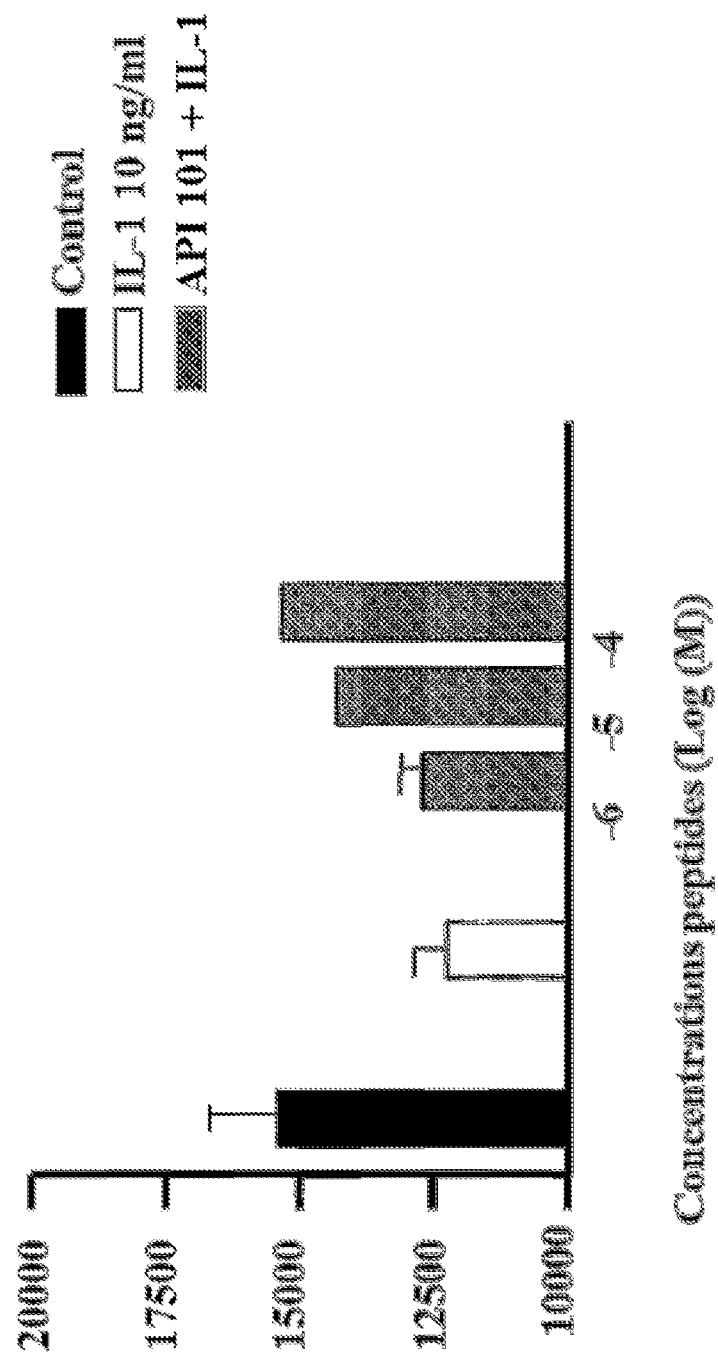
FIG. 1 shows a proliferation assay on carcinoma cells (A549) in the presence of IL-1β (10 ng/ml). Cells were pre-incubated with anti-IL-1R API-101 (SEQ ID NO: 1) peptide at different concentrations and then treated with IL-1β at 10 ng/ml for 24 hours. $^3$H-thymidine was then added. After 24 hours cells were collected, lysed and $^3$H-thymidine was counted.

The proliferation effect of IL-1 was measured in A549 carcinoma cells in the presence of peptide API-101 (SEQ ID NO: 1) and of IL-1 (10 ng/ml) using the incorporation of tritiated thymidine method. A549 cells were pre-incubated (45 min.) with different concentrations of peptides prior to stimulation with IL-1β (10 ng/ml) (37° C.) for 24 h; fetal calf serum was omitted 24 h prior to stimulation with IL-1β to avoid proliferative effects by other mitotic agents. $^3$H-thymidine (1 μCi/ml) was then added for 24 h, after which cells were washed three times with 10% cold TCA and lysed with O$_1$N NaOH/0.1% Triton X-100. Radioactivity was measured with a scintillation counter. Experiments were repeated 3 times in duplicates. As seen in FIG. 1, the peptide completely abrogated IL-1 inhibition of proliferation with an IC$_{50}$ of $10^{-6}$M.

It is well known in the art that IL-1 induces the synthesis of prostaglandin E$_2$ (PGE$_2$) in endothelial cells and/or chondrocytes in vitro. Therefore, human chondrocytes and piglet brain microvascular endothelial cells were pre-incubated 45-60 minutes at 37° C. with peptide API-101 ($10^{-6}$M) and human IL-1 (10 ng/ml) was added in the growing medium. After 24 hours of incubation, growth medium was collected and evaporated. PGE$_2$ measurement was determined by RIA assay with a commercial kit (Cederlane).

Figure 2:
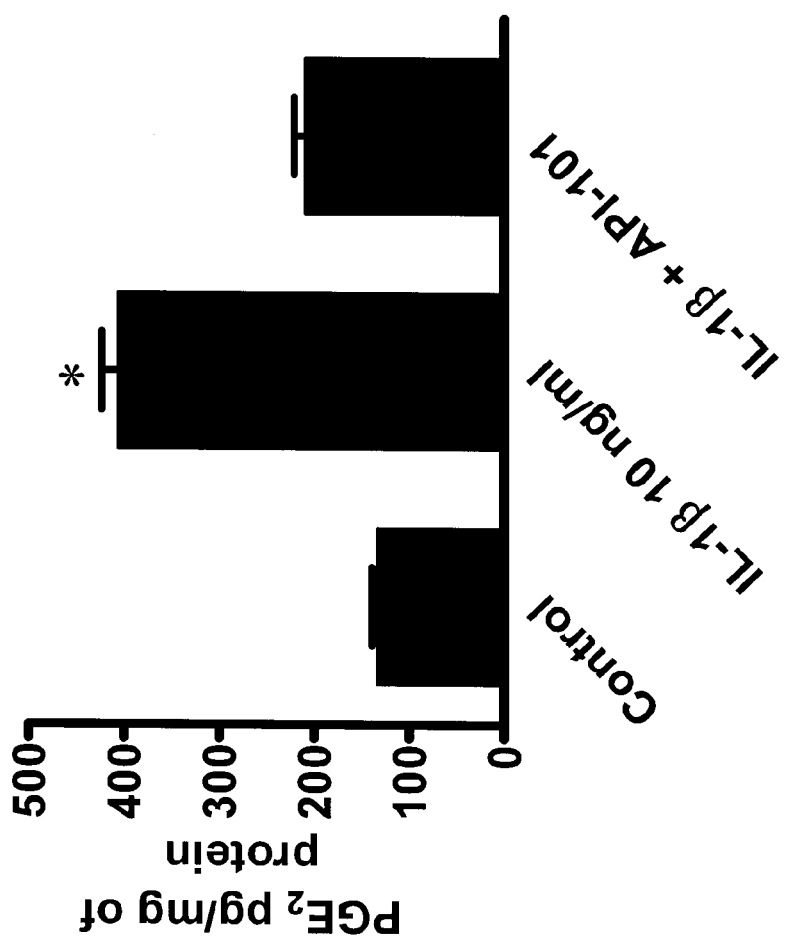
FIG. 2 shows the inhibitory activity of anti-IL-1R peptides on IL-1 induced PGE$_2$ synthesis by microvascular endothelial cells. Cells were pre-incubated 45 minutes with peptides and incubated with human recombinant IL-1β at a concentration of 10 ng/ml. PGE$_2$ synthesis was determined in the growth medium.
Figure 3:
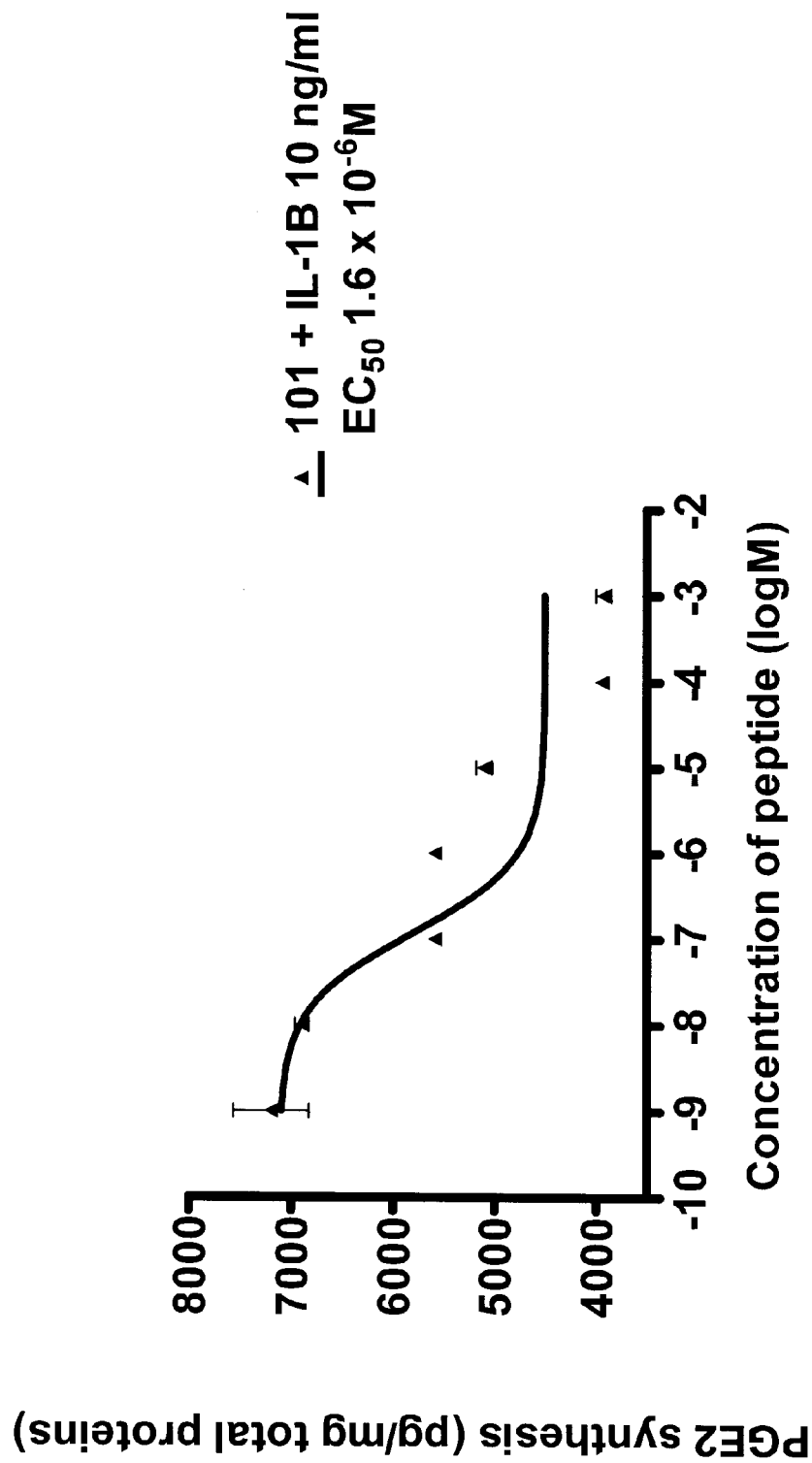
FIG. 3 shows a dose response curve of PGE$_2$ synthesis with API-101 (SEQ ID NO: 1) peptide on microvascular endothelial cells in the presence of 10 ng/ml of IL-1β.

FIG. 2 shows that PGE$_2$ synthesis induced by IL-1 (10 ng/ml) was remarkably decreased by more than 50% with API-101 (SEQ ID NO: 1) at a concentration of $10^{-6}$ M with an IC$_{50}$ of $10^{-6}$ M (FIG. 3).

Ex Vivo Characterization

In another experiment, vasomotricity studies were performed on piglet pial vessels to further evaluate the particular effect of API-101 (SEQ ID NO: 1) on the vasodilator effect of IL-1β.

Ex vivo vasomotor response on brain vessels was performed as described (Li et al., 1996; Hou et al., 2000; Hou et al., 2001; Hou et al., 2003). Brains were removed from Yorkshire piglets. Slices of cortex exposing the pial vessels were pinned to a wax base of a 20 ml bath containing Krebs buffer (pH 7.4) equilibrated with 95% O$_2$, 5% CO$_2$ and maintained at 37° C. Microvessels were visualized and recorded using a video camera mounted on a dissecting microscope. Vascular diameter was measured using a digital image analyzer. Vascular diameter was recorded before and after topical application of pre-constricting agent, U46619 ($10^{-7}$ M). After stabilization of preparation, the ligand (IL-1β, 75 ng/ml) was added until stable vasodilation was detected. Peptides were subsequently added at different concentrations from $10^{-10}$ to $10^{-5}$ M. Reversal of vasodilatation was visualized and measured as previously described (Hou, et al. 2000; Hou et al. 2001; Hou et al. 2003); triplicate measurements were conducted on 2 animals.

Figure 4:
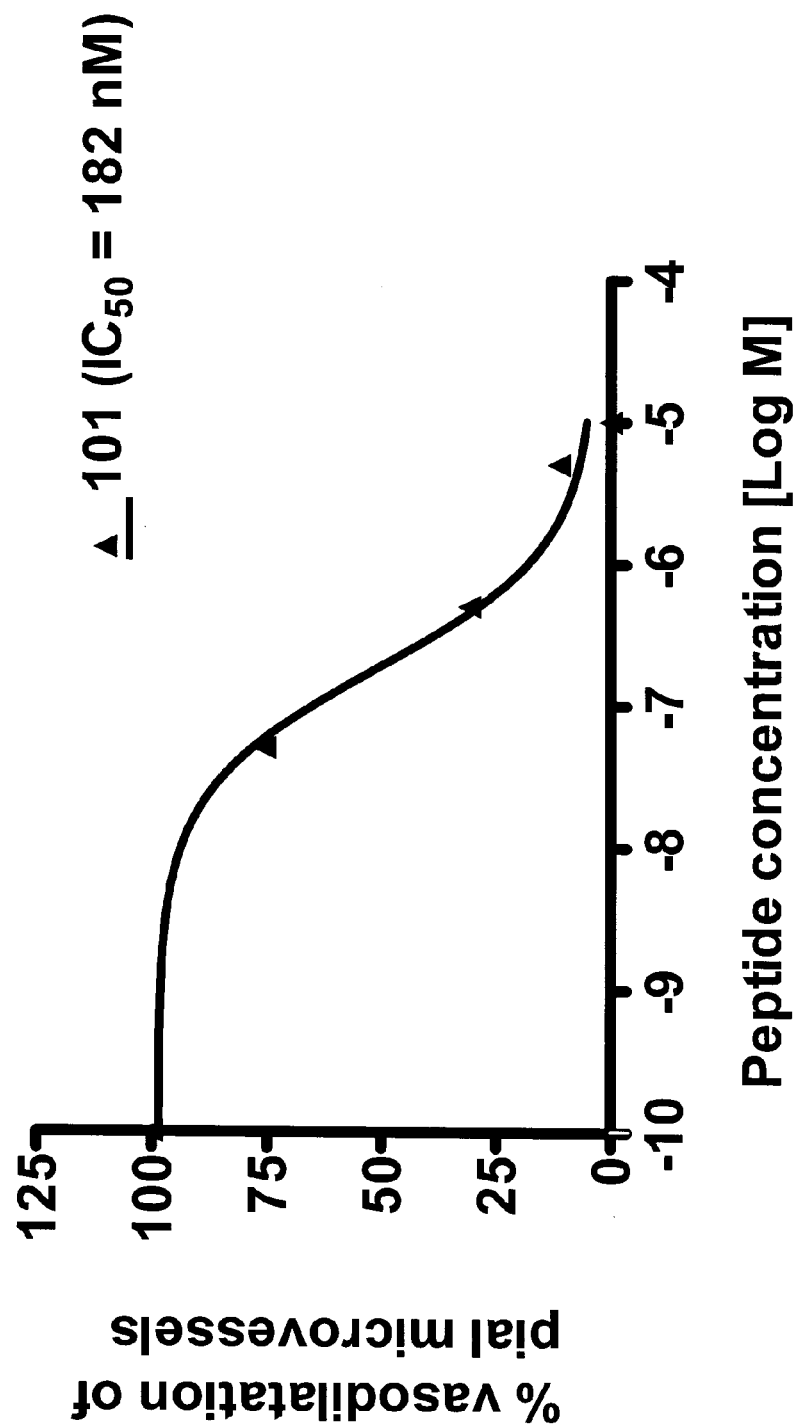
FIG. 4 shows a dose response curve of vasodilatation of pial microvessels in the presence of 100 ng/ml of IL-1β and anti-IL-1R API-101 (SEQ ID NO: 1) and API-108 peptides.

As seen on FIG. 4, API-101 (SEQ ID NO: 1) could prevent the vasodilation induced by IL-1β (75 ng/ml) with an IC$_{50}$ of 182 nM.

In summary, these results show that by targeting the IL-1R/IL-1Racp receptor, API-101 (SEQ ID NO: 1) was efficient in inhibiting the biological response of IL-1.

EXAMPLE 2

Effect of Derivatives of API-101 Obtained by Alanine Scan

Having demonstrated a significant effect of the API-101 (SEQ ID NO: 1) antagonist, experiments were carried out to provide structure function relationship data for API-101 and derivatives, to identify the most important regions for activity. Alanine scan mutations were therefore performed on API-101 (SEQ ID NO: 1) (see FIG. 17 for the sequence of the peptides). Of course, other amino acids could have been used in the place of alanine to perform the scanning experiment.

In Vitro Characterization

A table summary of the results depending on the mutations performed is shown in FIG. 17.

Figure 5:
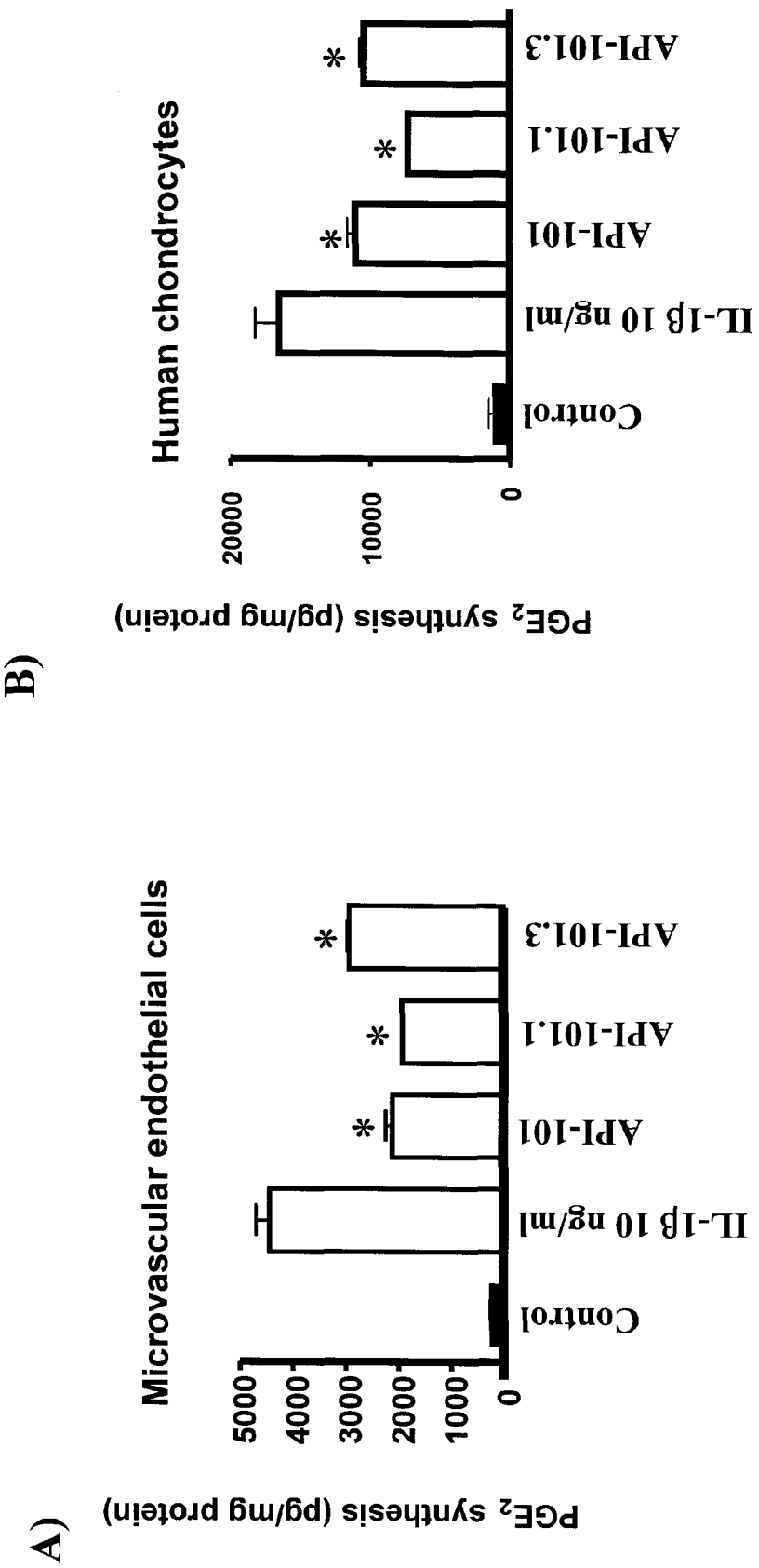
FIG. 5 shows the in vitro PGE$_2$ synthesis in the presence of IL-1β (10 ng/ml) and alanine scanned peptides (10–6M) on microvascular pig endothelial cells (A) and on human chondrocytes (B).

Efficiencies and inhibitory activities of the mutated peptides were determined by measuring the inhibition of IL-1-induced PGE$_2$ synthesis (see experimental protocol above in Example 1). API-101.1 (SEQ ID NO: 2) only had a slightly improved efficacy in endothelial cells and in chondrocytes as compared to the parent peptide API-101 (SEQ ID NO: 1). On the other hand, API-101.5 (SEQ ID NO: 6), −101.6 (SEQ ID NO:7), and −101.7 (SEQ ID NO:8) lost almost all activity in both cell types suggesting that the targeted VELA region is important for the activity of the peptide. FIG. 5 shows a graphical representation of the most efficient peptides of the series. All peptides were tested at concentration $10^{-6}$ M.

Ex Vivo Characterization

Figure 6:
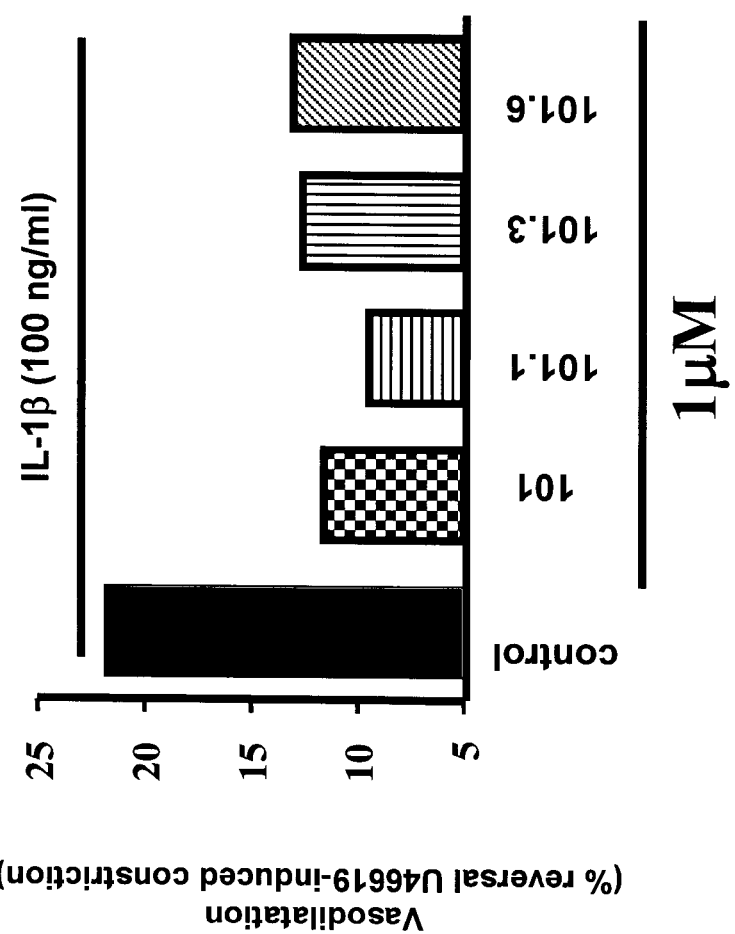
FIG. 6 shows the ex vivo reversal of IL-1β-induced (100 ng/ml) vasodilatation of pial microvessels with the most active API-101 (SEQ ID NO: 1) alanine scanned peptides.

Vasomotricity studies were also performed on API-101 alanine scan peptides (see example 1 for experimental protocol). FIG. 6 shows that API-101 (SEQ ID NO: 1), −101.1, −101.3 and −101.6 (SEQ ID NOs: 2, 4 and 7, respectively) all reversed the vasodilation induced by IL-1β (75 ng/ml) and that API-101.1 (SEQ ID NO: 2) showed a slightly increased inhibitory activity over API-101, and abolished 70% of the vasodilation.

Overall, the mutations or substitutions did not significantly increase the activities of the peptide derivatives over that of API-101 (SEQ ID NO: 1), but information about an important region for the activity of the peptide was obtained.

EXAMPLE 3

Effect of Further Optimization of API-101 on the Improvement of its Activity

Figure 7:
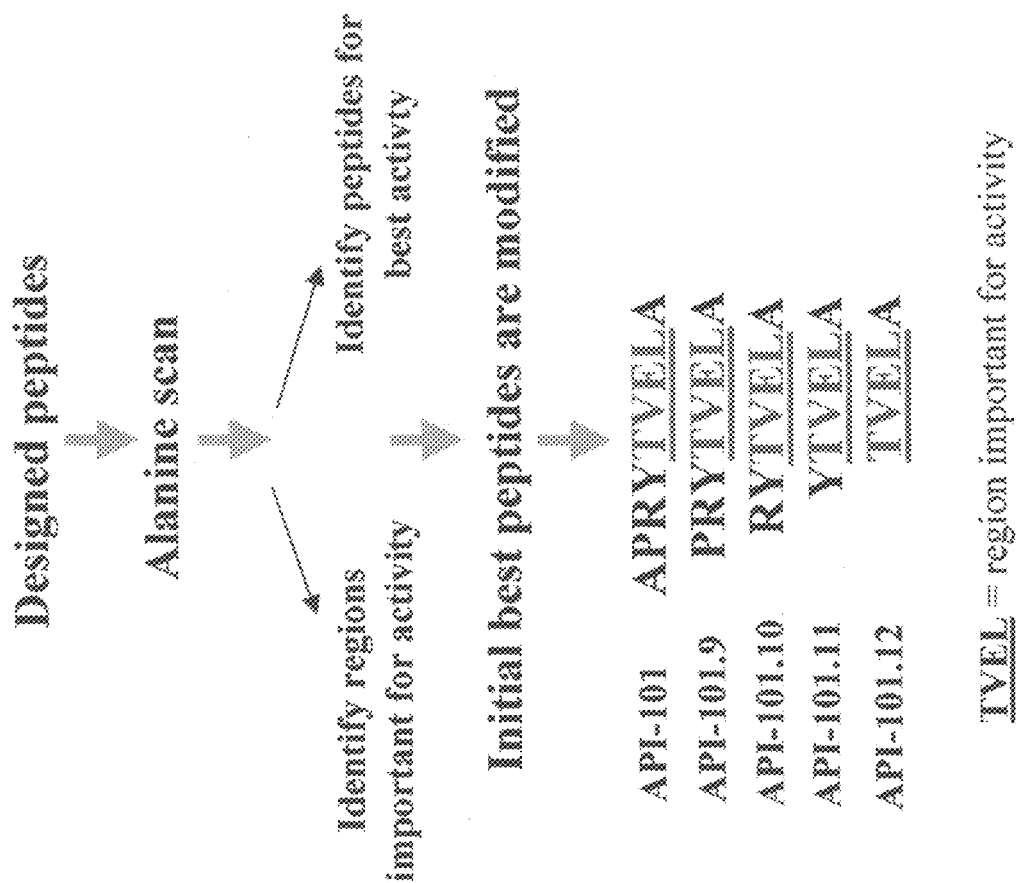
FIG. 7 shows a representation of the optimization scheme followed for API peptides (SEQ ID NOS: 1, 9, 10, 11, and 12).

To further improve the activity and to validate the alanine scan conclusions obtained on the region in API-101 important for its activity, the amino acids from the N-terminal end of the peptide were gradually truncated. FIG. 7 shows the sequence of the new peptides as well as the general pattern of optimization employed for API-101.

In Vitro Characterization:

IL-1β induces proliferation of human fibroblasts cells. Truncated peptides were assayed for IL-1β induced WI-38 (human lung fibroblasts) proliferation with the tritiated thymidine uptake protocol (see protocol example 1).

Figure 8:
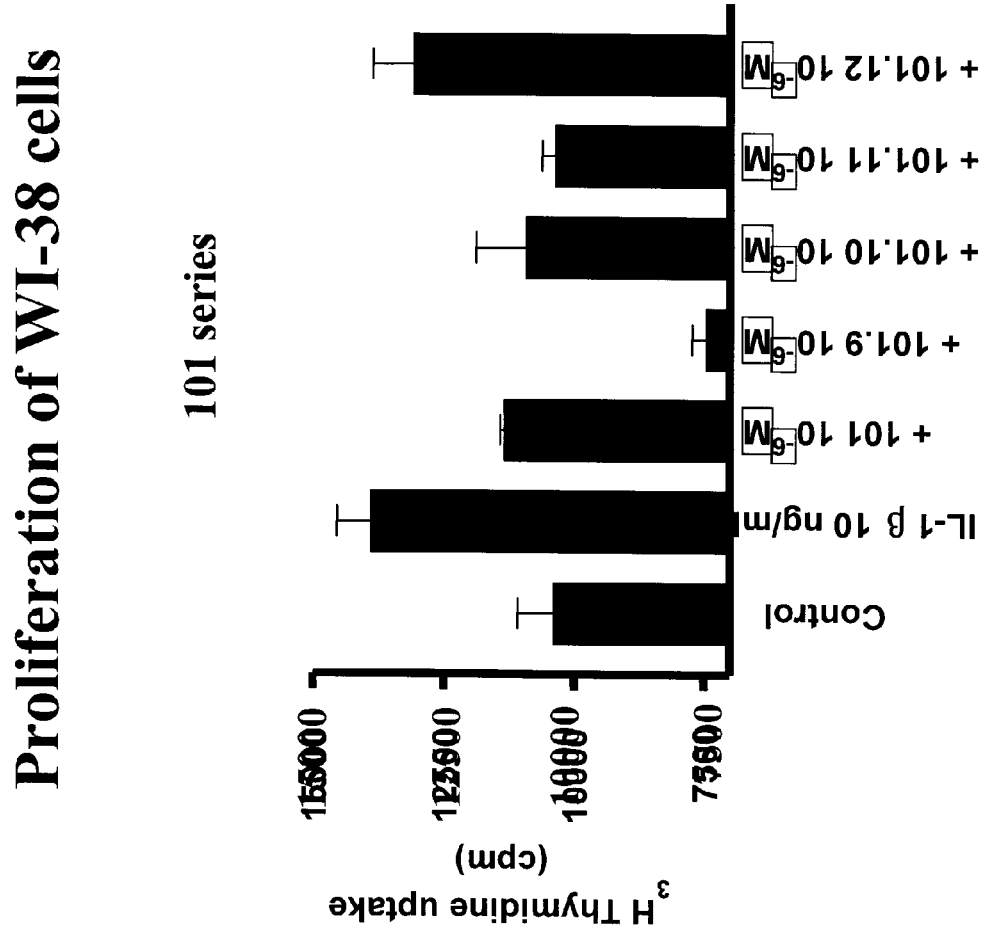
FIG. 8 shows a proliferation assay performed on human lung fibroblasts (WI-38) in the presence of IL-1β (10 ng/ml) and truncated API-101 (SEQ ID NO: 1) derivatives.

Relative to API-101 (SEQ ID NO: 1) which abolished 65% of IL-1R induced proliferation; API-101.10 (SEQ ID NO: 10) and API-101.11 (SEQ ID NO: 11) abolished 100% of IL-1β-induced proliferation (FIG. 8).

Determination of IL-1-induced PGE$_2$ synthesis was also performed on API-101 truncated derivatives. FIG. 18 shows a summary of the potency as well as the efficacy of the different peptides. API-101.10 (SEQ ID NO: 10) was the most efficient and potent truncated peptide with 0.2 nM and 1.2 nM IC$_{50}$ on WI-38 and endothelial cells compared to API-101 (790 nM and 220 nM). API-101.11 (SEQ ID NO: 11) and 12 (SEQ ID NO: 12) showed a decrease in potency and efficacy, which indicated that the peptide truncation after the arginine influenced the potency and efficacy thereof.

Cytotoxicity

Cytotoxicity of the latest derivatives of API-101 was also determined in two cell types: WI-38 and brain microvascular endothelial cells. Cell viability was assayed as previously described (Beauchamp et al. 2001; Brault et al. 2003). Endothelial and fibroblast cells were incubated with peptides at various concentrations at 37° C. for 24 h. MTT (3-[4,5-Dimethylthiazol-2-yl]-2,5-diphenyl-tetrazolium bromide) in PBS was added to the growth medium at a final concentration of 500 μg/ml. Cells with MTT were incubated for 2 h at 37° C. Growth medium was then aspirated and 200 μl of a solution of 24:1 isopropanol:HCl 1N was added in each well to lyse the cells. Viable cells transform the MTT product (via the mitochondria) into a measurable colorimetric (blue) product named formazan. Formazan production (and cell viability) was determined by measuring the optical density of 100 μl of lysate at 600 nm.

Figure 9:
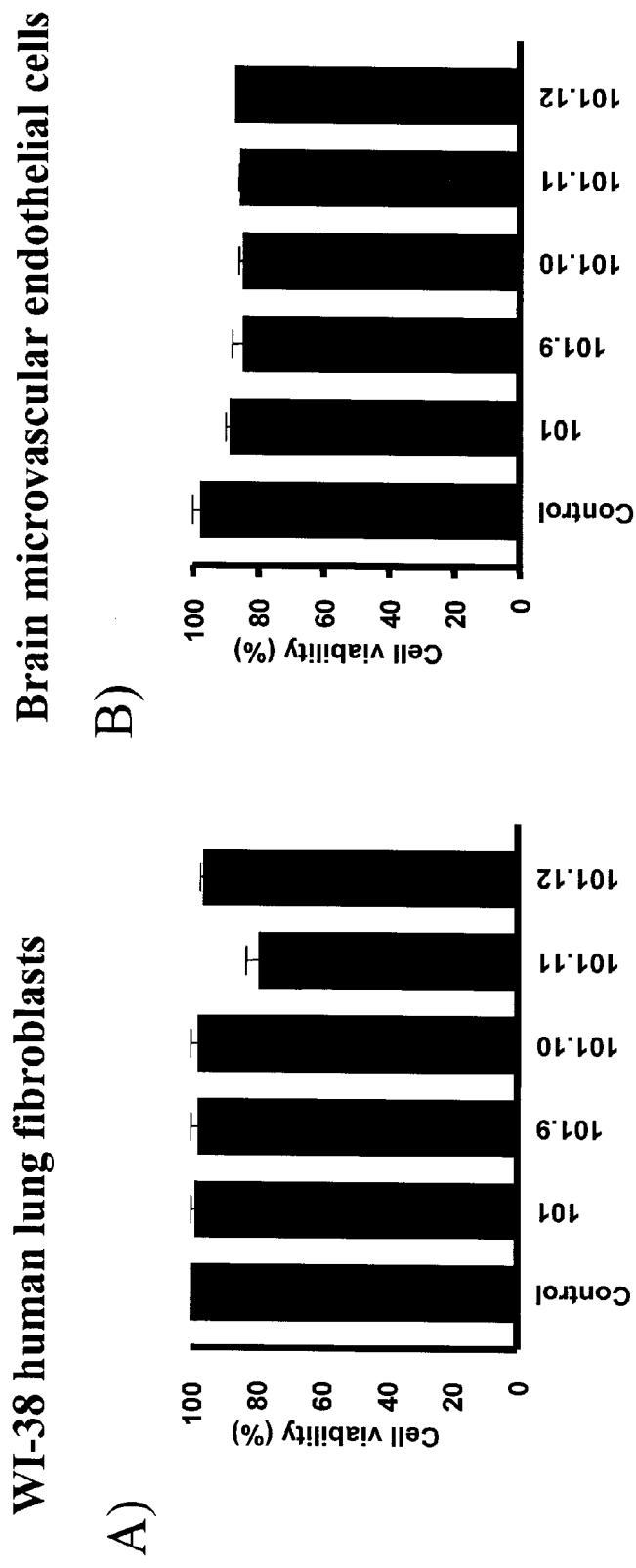
FIG. 9 shows the cytotoxicity of derivatives of API-101 peptides ($10^{-5}$M, MTT assay) on WI-38 cells (A); and brain microvascular endothelial cells (B).

Cells did not show any toxicity when exposed to $10^{-5}$ M of peptides for 24 hours as shown in FIG. 9.

Ex Vivo Characterization

Figure 10:
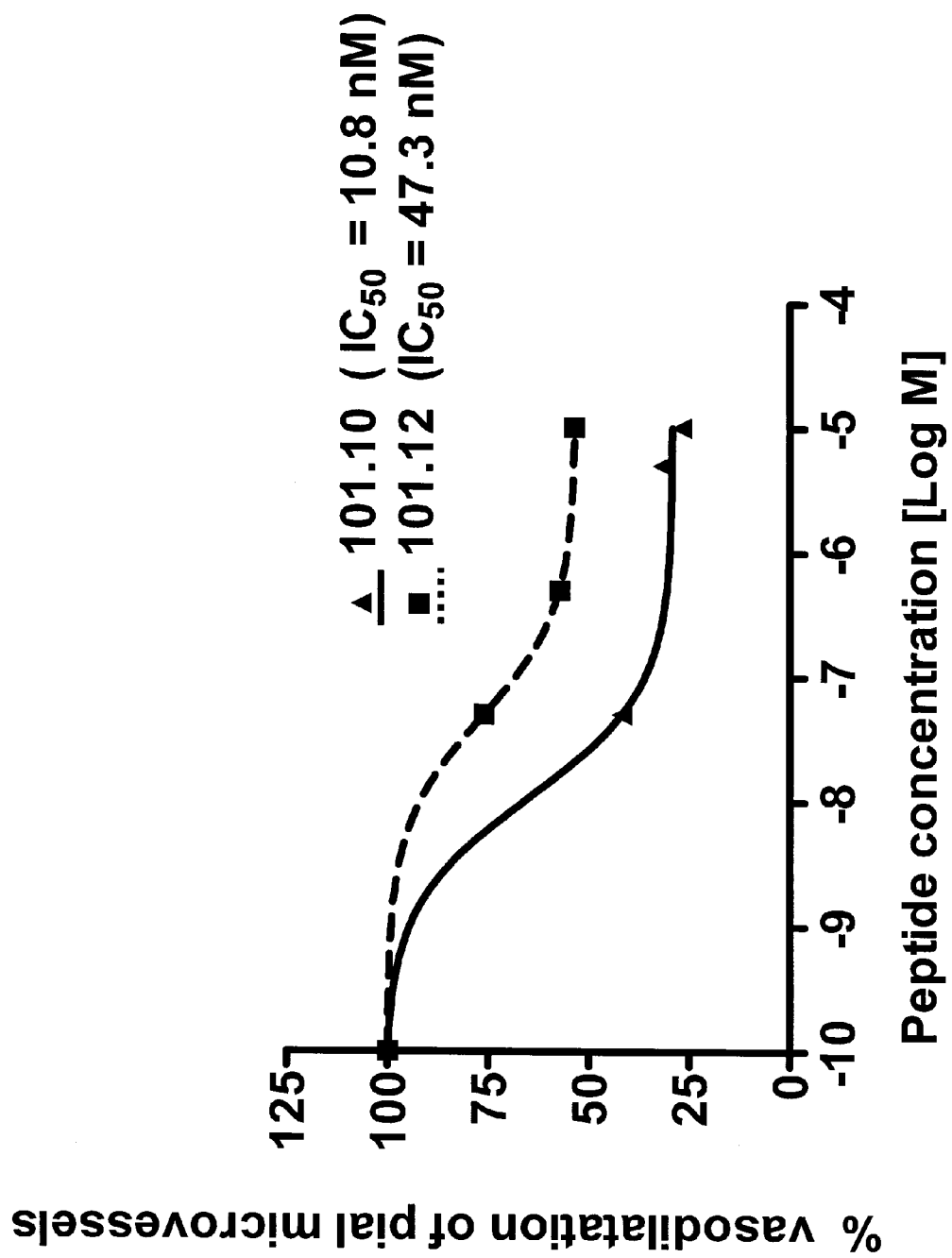
FIG. 10 shows dose response curves of IL-1β (75 ng/ml) induced rat aorta vasodilatation in presence of API-101 derivatives: API-101.10 (SEQ ID NO: 10) and API-101.12 (SEQ ID NO: 12) using a concentration range of $10^{-5}$M to $10^{-10}$M for both peptides.

Vasomotricity experiments were also carried out to evaluate the effect of API-101.10 (SEQ ID NO: 10) (the peptide having shown the best activity in vitro) on vasodilation induced by IL-1 (for protocol, see Example 1). API-101.10 (SEQ ID NO: 10) showed the best IC$_{50}$ at 10.8 nM and was 100 fold more potent than API-101 (182 nM) (FIG. 18). The peptides 101.9 (SEQ ID NO: 9), 101.11 (SEQ ID NO: 11), and 101.12 (SEQ ID NO: 12) showed better IC$_{50}$ than API- 101 (SEQ ID NO:1) (FIG. 18 and FIG. 10). The concentration range for peptides in FIG. 10 was from $10^{-10}$ M to $10^{-5}$ M. Thus, in the ex vivo experiments, API-101.11 (SEQ ID NO: 11) and API-101.12 (SEQ ID NO: 12) showed significantly improved inhibitory activities as compared to the parental peptide.

In Vivo Characterization

Systemic Effects of IL-1R/IL-1RAcP Peptides Antagonists

The API-101 derivatives, API-101.10 (SEQ ID NO: 10) (and others) were tested to assess whether they could reverse the physiological actions of the natural ligand in vivo by injecting the derivative through the jugular or directly into the stomach (to verify the stability of the peptide through the digestive tract). Sprague-Dawley rats (300 g) were anesthetized with isoflurane (2.5-4%). The natural ligand (IL-1β) or vehicle (saline) was injected through the jugular vein (5 μg/kg). Blood was taken from the carotid artery for subsequent $PGE_2$ measurements before and 10 min after each injection. Peptides were administered (dosage based on $IC_{50}$ values and a volume of distribution equivalent to the extracellular space) either in the jugular vein or directly in the stomach (5 times dose used intravenously, (iv)). Arterial blood pressure and heart rate were continuously monitored (Gould) while temperature and blood gases (Radiometer) were measured for routine analysis as previously described (Li et al. 1997; Hardy et al. 1999; Najarian et al. 2000). Experiments were repeated 3 times.

Figure 11:
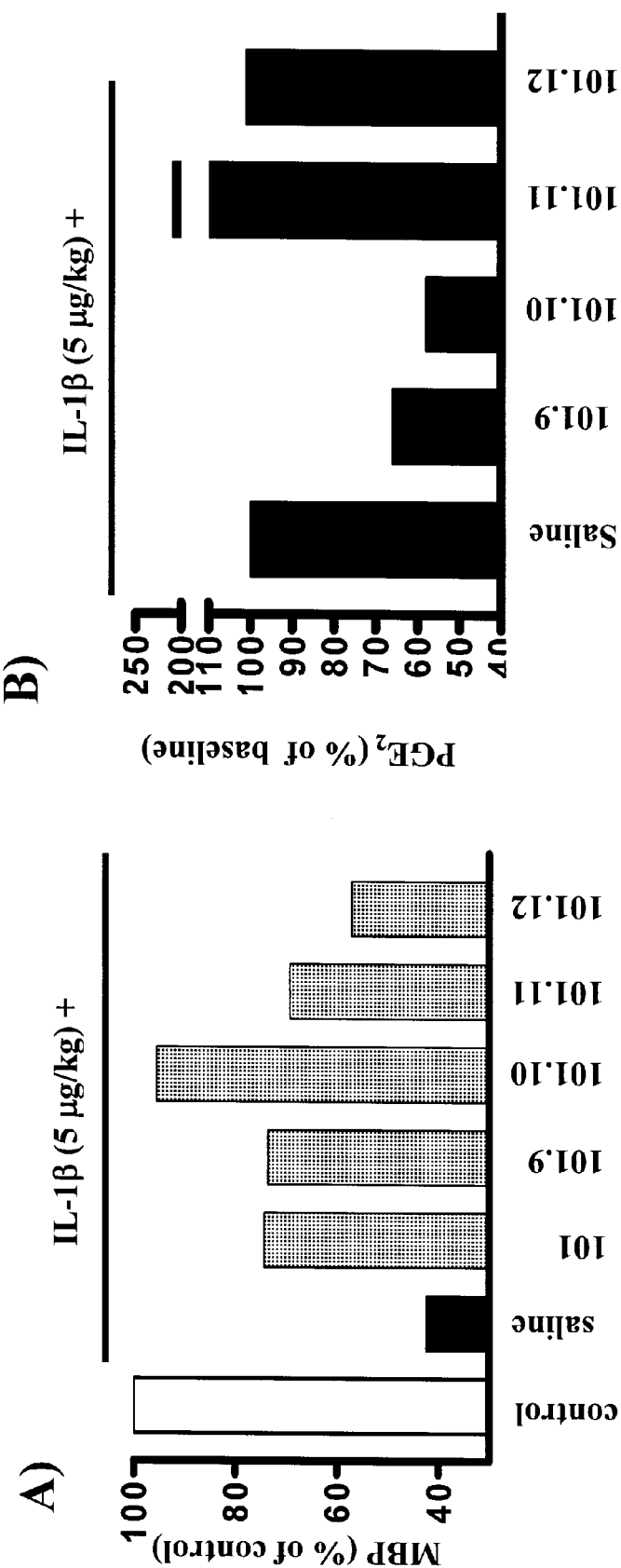
FIG. 11 shows the in vivo effects of IL-1β-induced systemic hypotension and serum PGE$_2$ synthesis by systemic administration of API-101 peptides in rats. (A) Mean Blood Pressure (MBP) decrease in the presence of IL-1β and/or peptide 101.10 ($10^{-5}$M). (B) Modulation increase of serum PGE$_2$ synthesis in presence of IL-1β and peptide 101.10 ($10^{-5}$M).
Figure 12:
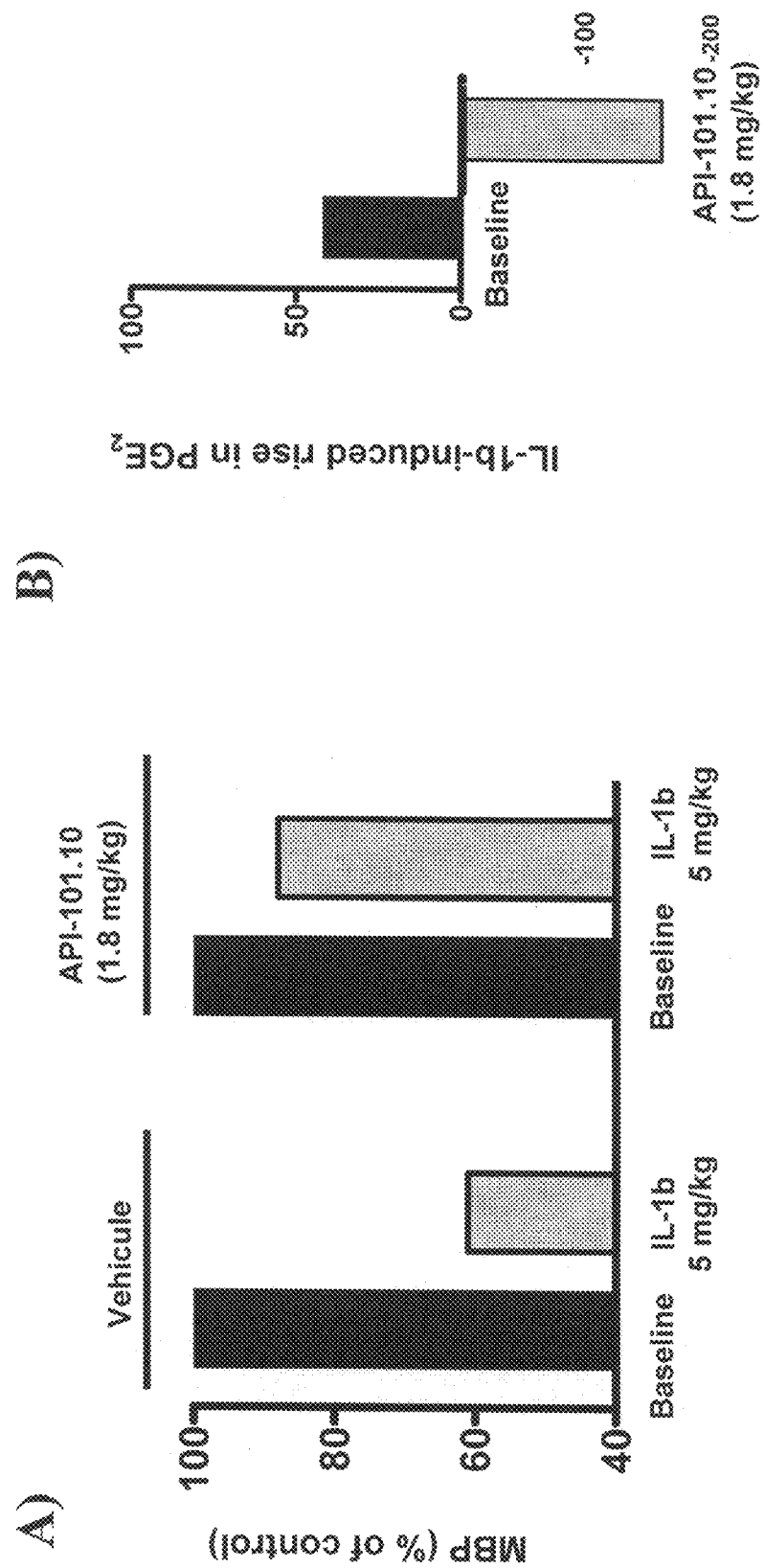
FIG. 12 shows the effect of enteral injection of API-101.10 on IL-1β-induced hypotension and PGE$_2$ synthesis in rats. A)

Severe hypotension induced by IL-1β was observed when administered to the rats by either ways mentioned above. The following peptides constitute example antagonists that were able to prevent hypotension in vivo:

1. API-101.10 (SEQ ID NO: 10): When administrated by jugular injection after IL-1β injection (5 μg/kg) prevented hypotension by 95% at a concentration of $10^{-8}$ M (i.e. it relieved the IL-1 induced-hypotension). Other derivatives like API-101.9 (SEQ ID NO: 9) were also able to prevent this biological effect of IL-1β but were less effective than peptides API-101.10 (SEQ ID NO: 10), 101.101 (SEQ ID NO:13) or peptidomimetics, 101.109, 101.111 and 11.112 (FIG. 20) but significantly better than the saline control (FIG. 11 A). This clearly demonstrates that the peptides have an hypertensive effect in vivo in animals, by reversing the effect of IL-1β.
2. When administrated directly into the stomach, at a concentration of $10^{-5}$ M, the peptide reduced IL-1β hypotension by 60%. This result demonstrated that enteral administration of the 101.10 (SEQ ID NO: 10) peptide still maintained a major effect on IL-1β induced hypotension (FIG. 12A) and thus can maintain efficacy and stability along the digestive tract.

Another way of assessing the effect of IL-1 receptor antagonists of the present invention on IL-1R activity in vivo is by measuring $PGE_2$ levels in rat serum.

If the IL-1R receptor antagonist of the present invention can prevent hypotension in vivo they should be able to prevent also the synthesis of $PGE_2$. $PGE_2$ was therefore measured in serum of rats used for the experiments mentioned above (e.g. Arterial Blood Pressure variation measurement). Examples of results obtained with truncated API-101 derivatives peptides is described below.

Once again, API-101.10 (SEQ ID NO: 10) was shown to be the most effective of the API-101 derivatives tested in preventing $PGE_2$ synthesis (60%) when the peptide was injected in the jugular. Higher inhibition was obtained when the peptide was injected directly in the stomach (FIGS. 11 B and 12B).

Further Optimization of API-101.10

API-101.10 (SEQ ID NO: 10) was identified as the best peptide derivative from the last round of optimization. Thus, truncation of API-101 from 9 to 7 amino acids from the N-terminal could improve the potency without compromising the efficacy in vitro, ex vivo and in vivo.

FIG. 15 shows the next mutations that were performed on API-101.10 (SEQ ID NO: 10). The arginine of API-101.10 (SEQ ID NO: 10) was replaced by citrulline—to change from a guanidine to a urea group near the N-terminal. Other mutations (e.g. E to Q in API-101.102, SEQ ID NO: 14, and 101.103, SEQ ID NO: 15) and a truncated peptide at the C-terminal (API-101.108, SEQ ID NO: 20) were also performed to improve the potency and the efficacy of the peptides.

FIG. 15 shows an in vitro characterization of these peptides. Measurement of $PGE_2$ was performed with piglet brain microvessel endothelial cells and WI-38 human fibroblasts. Some of the mutations were advantageous and gave major increases in potency. For example: API-101.103 (SEQ ID NO: 15), and 101.107 (SEQ ID NO: 19) showed more than 1000 fold better potency with $IC_{50}$ of 0.05 pM and 0.1 pM in human WI-38 cells.

For these newly derived peptides, ex vivo experiments were then conducted. Brain tissues were incubated with the peptides and IL-1β and cGMP was measured with a commercial kit (Amersham bioscience, cGMP assay biotrack™ system). API-101.10 (SEQ ID NO: 10) already inhibited 85% of IL-1β-induced cGMP production ($10^{-6}$ M) and API-101.103 (SEQ ID NO: 15) and 101.106 (SEQ ID NO: 18) inhibited more than 90% of cGMP production (results not shown). It thus seems, that removal of the negative charge of the glutamate and removal of the threonine can improve the potency of the antagonist. Of note, the activity of API-101.10 (SEQ ID NO: 10) was shown to be superior to that of the Amgen drug Kineret™ (data not shown).

Taken together, the present invention clearly demonstrates that AP1-101 is a potent and efficacious IL-1 receptor antagonist. Furthermore, it clearly demonstrates that starting from API-101 (SEQ ID NO: 1), the inventors could derive, in a systematical fashion, even more potent and efficacious antagonists (as shown by a comparison of the $IC_{50}$ of API-101 and that of derivatives of the 101.100 series). The present invention therefore provides the means to identify new IL-1R/IL-RacP receptor antagonists and methods of treating or preventing diseases or disorders associated with a defect in the pathway involving IL-1R/IL-RacP. The person of ordinary skill in the art can also derive peptidomimetics and other derivatives based on the teaching of the present invention and the state of general knowledge in the art, and as described below.

EXAMPLE 4

Efficacy of API-101 in a Rat Model of Inflammatory Bowel Disease (IBD)

IBD is a chronic inflammation of the gastrointestinal tract with high incidence among the human population. The present experiment was done in order to verify if the peptide API-101.10 (SEQ ID NO: 10) could prevent yet another inflammatory process in an IBD animal model induced with the trinitrobenzene sulphonic acid (TNBS). TNBS causes an IL-12 mediated $T_H$-1 response characterized by transmural infiltration of neutrophils and macrophage, fissuring ulcerations and submucosal fibrosis characteristic of acute intestinal inflammation and Crohn's disease (Bouma and Strober 2003).

Inflammatory Bowel Disease Model:

Colon inflammation was induced by intra-rectal/colon administration of the hapten trinitrobenzene sulphonic acid (TNBS) on male Sprague-Dawley rats (175-200 g) (Bouma, Nature Rev, 2003; Morris, Gastroenterology, 1989). Animals were anesthetized with isoflurane and TNBS dissolved in 50% ethanol (vol/vol). 120 mg/ml (TNBS) was administered into the colon (total volume of 0.25 ml per rat) using a polyethylene tube (PE50). The cannula was inserted at 8 cm from the anus and kept in place for at least 15 min after TNBS administration in order to prevent expulsion of the solution. Two hours prior to TNBS administration, The API-101 derivative API-101.10 (SEQ ID NO: 10,) 1.1 mg/kg) or 0.9% saline was administered intravenously via the caudal vein (total volume of 0.3 ml). API-101.10 (2.2 mg/kg, 6 times dose used for blood pressure experiments based on t½=2-3 h for various peptides) or 0.9% saline were then continuously infused using primed intraperitoneal alzet pumps. A third group (control) was not injected with TNBS. Six days after administration of TNBS, rats were killed by $CO_2$ inhalation. Day 6 was chosen as an endpoint because by day 7 spontaneous tissue regeneration begins and this can mask the therapeutic effect of the tested peptide or peptide derivative. Colon was removed and examined macroscopically (adhesions, ulcerations, discoloration and bleeding) and histologically (neutrophil infiltration, epithelial injury, crypt distortion and ulcerations) (Anthony et al. 1995; Padol et al. 2000; Dieleman, L A, et al. 1997; Torres M I et al. 1999). Two animals per group were studied.

Histological transversal sections were cut at 4-6 cm from the proximal anal region and colored with the hematoxylin/eosin method.

The TNBS model of inflammatory bowel disease reproduces the inflammatory characteristics and tissue injuries of Crohn's disease (e.g. in humans). As showed in FIG. 14 A and B, morphologically, the colon of the animals injected with TNBS presented thickening, edema and discoloration of the intestinal wall indicating a significant inflammation. Macroscopic characteristics of colons from animals pre-treated with API-101.10 (SEQ ID NO: 10) resemble those of the control animals (FIG. 14 C). Histological features consisted of neutrophil infiltration into the epithelial layer and crypts (see FIG. 16 B), epithelial lining injury as well as the loss of crypts (FIG. 16 B). Pre-treatment of the animals with API-101.10 (SEQ ID NO: 10) prevented TNBS-induced colon damage. In FIG. 16, one can appreciate that the organization and integrity of the crypts in the API-101.10 (SEQ ID NO: 10)-treated colon is conserved even if there is still some inflammation (half the dose of API-101.10 was used as compared to the macroscopic analysis experiment). The injuries on the epithelium lining shown in FIG. 16 B are completely prevented in the API-101.10 (SEQ ID NO: 10) treated animals (FIG. 16 C). Hence, the IL-1R antagonists of the present invention are also extremely efficient in an animal model of inflammatory bowel disease.

EXAMPLE 5

Peptidomimetics API-101.109, API-101.110

To further improve the efficacy and the potency of the antagonists of the present invention, peptidomimetics were synthesized and screened in vitro. In one embodiment, the peptidomimetics are derived from API-101.10 (SEQ ID NO: 10) or API-101.107 (SEQ ID NO: 19) and the primary structures are: for API-101.109 RY(HyVal)PELA (SEO ID NO: 46) (FIG. 20) and for API-101.110 RY($I^2$aa)ELA (SEQ ID NO: 47) (FIG. 21) where HyVal is beta-Hydroxyvaline and $I^2$aa is indolizidin-2-one amino acid (2-oxo-3-amino-azabicyclo[4.3.0]nonane-9-carboxylic acid. These peptidomimetics are also D-peptides.

Methodology:

Preparation of Solid Support

Benzhydrylamine resin hydrochloride (2 g, Advanced Chemtech, Lot # 11988, 100-200 mesh, loading 1.2 mmol/g) was washed for one min three times with 10 ml/g of each of the following reagents: 5% DIEA/$CH_2Cl_2$; $CH_2Cl_2$; DMF. The resin was treated with a solution of N-(Fmoc)aminocaproic acid (1.27 g, 3.6 mmol, 150 mol %), TBTU (1.27 g, 3.96 mmol, 165 mol %), DIEA (690 µL, 3.96 mmol, 165 mol %), and HOBt (535 mg, 3.96 mmol, 165 mol %) in DMF (20 ml, 10 ml/g of resin), and agitated for 1 h when a negative Kaiser test was observed. The resin was washed with 10 ml/g of the following solutions in an alternating sequence: DMF (3×1 min) and isopropyl alcohol (3×1 min). The resin was then treated with piperidine in DMF (20% v/v, 20 ml, 1×2 min, 1×3 min, 1×10 min), followed by an alternating sequence of 10 ml/g of DMF (3×1 min) and isopropyl alcohol (3×1 min). The resin was agitated with a solution of 4-[(R,S)-α-1(9H-fluoren-9-yl)-methoxy-formamido]-2,4-dimethoxybenzyl]-phenoxyacetic acid (Knorr linker, 1.94 g, 3.6 mmol, 150 mol %), TBTU (1.27 g, 3.96 mmol, 165 mol %), and DIEA (690 µL, 3.96 mmol, 165 mol %) in DMF (20 ml) for 1 h. The resin was sequentially washed with 10 ml/g of the following solutions: DMF (3×2 min), isopropyl alcohol (3×2 min), and $CH_2Cl_2$ (3×2 min). Drying of the resin under high vacuum overnight yielded 3.66 g resin.

Determination of Loading

Piperidine (20 g) and DMF (20 g) were mixed. To a quantity of this solution (20 ml, 18.08 g) in a sample vial was added dry resin (20 mg), and the suspension gently agitated by passage of a stream of argon. After 50 min, the resin was allowed to settle. An aliquot of solution (1 ml) was diluted 50-fold with ethanol, and the absorbance measured at 301 nM [(N-(9-fluorenylmethyl)piperidine UV $\lambda_{max}$: 267 nM (ε 17500), 290 (5800) and 301 (7800)]. Two separate determinations (averaged) gave $A_{301}$=0.0785. The following equation: [c (mmol/g)=(OD×50×$10^2$)/7800] gave c=0.50 mmol/g (Meienhofer et al. 1979).

Peptide Synthesis

Amino acids were purchased from Advanced Chemtech (Louisville, Ky.), and used as the following derivatives: N-Fmoc-D-Ala-OH.$H_2O$, N-Fmoc-D-Leu-OH, N-Fmoc-D-Glu(O-t-Bu)-OH, N-Fmoc-D-Pro-OH, N-Fmoc-D-Tyr(O-t-Bu), N-Fmoc-D-Arg(Pmc)-OH. (R)-β-hydroxy-N-(Fmoc) valine was prepared from (R)-β-hydroxy-N-(Boc)valine (Dettwiler et al., 2003) by removal of the Boc group (1:1 TFA (trifluoroacetic acid)/$CH_2Cl_2$), protection with Fmoc-OSu and NaHCO$_3$ in aqueous acetone (Capatsanis et al. 1983), followed by purification by chromatography over silica gel (1:1:98 MeOH/HOAc/CHCl$_3$) and lyophilization from aqueous acetonitrile (78% yield). (3R,6R,9R)-2-Oxo-3-[N-(Fmoc)amino]-1-azabicyclo[4.3.0]-nonane-9-carboxylic acid was prepared from (3R,6R,9R)-methyl 2-oxo-3-amino-1-azabicyclo[4.3.0]-nonane-9-carboxylate (in turn prepared (Lombart et al. 1996) from D-glutamic acid) by Fmoc-protection with Fmoc-OSu and NaHCO$_3$ in aqueous acetone (Capatsanis et al. 1983), followed by selective hydrolysis of the methyl ester (Pascal et al. 1998). Peptide synthesis was performed on a 0.1 mmol scale (200 mg resin), and conducted by deprotection with piperidine in DMF (10 ml/g resin, 20% v/v, 1×2 min, 1×3 min, 1×10 min) followed by washing with DMF (10 ml/g resin, 5×1 min). Fmoc protected amino acid (0.5 mmol, 500 mol %) dissolved in a solution of TBTU in DMF (0.25 M, 2 ml) was added to the resin. After agitation of the resin (5 min), DIEA (0.6 mmol, 600 mol %) was added, and agitation continued for 1 h. The resin was washed with DMF (10 ml/g resin, 5×1 min), and coupling efficiency determined using the Kaiser test. The resin was agitated using a mechanical vortex apparatus during coupling, rinsing and deprotection sequences. Rp-HPLC analysis was performed on an Alltech C18 column (dimensions 250 mm×4.6 mm) using acetonitrile/water/TFA mixtures, where solvent A=water/0.1% TFA and solvent B=MeCN/0.1% TFA (see below). The flow rate was 0.5 ml/min, and detection was performed at 214 nM.

Peptidomimetic API-101.109 (KH-C29099)

Cleavage from the resin (180 mg) with simultaneous side chain deprotection was conducted by treating the resin with 20 ml/g of a cocktail containing TFA (82.5%), thioanisole (5%), water (5%), phenol (5%) and triethyl silane (2.5%) and agitating with a mechanical vortex apparatus for 1 h at room temperature. Subsequent filtration, rinsing with TFA (2×1 ml) and precipitation in Et$_2$O at 0° C. gave the peptide. Isolation of the crude peptide as the dihydrochloride salt by lyophilization from HCl solution (1 M) gave a white powder (18 mg) that was shown to be ≥90% pure by rp-HPLC (RT=14.6 min) using an eluant of 5-40% B in A over 20 min. LRMS calcd for C$_{39}$H$_{64}$N$_{11}$O$_{11}$ (MH$^+$) 862, found 862.

Peptidomimetic API-101.110 (KH-C50110)

Cleavage from the resin (22 mg) with simultaneous side chain deprotection was conducted by treating the resin with 20 ml/g of a cocktail containing TFA (82.5%), thioanisole (5%), water (5%), phenol (5%) and triethyl silane (2.5%) and agitating with a mechanical vortex apparatus for 1 h at room temperature. Subsequent filtration, rinsing with TFA (2×1 ml) and precipitation in Et$_2$O at 0° C. gave the peptide. Isolation of the crude peptide as the dihydrochloride salt by lyophilization from HCl solution (1 M) gave a white powder (5.7 mg) that was shown to be ≥85% pure by rp-HPLC (RT=19.8 min) using an eluant of 5-40% B in A over 20 min. LRMS calculated for C$_{38}$H$_{60}$N$_{11}$O$_{10}$ (MH$^+$) 830, found 830.

Results:

IL-1-induced PGE$_2$ synthesis assay on endothelial cells was used as a screening assay for the peptidomimetics. The peptidomimetic compound API-101.110 (FIG. 21) had a potency of 0.2 pM of IC$_{50}$, which is 10 fold higher than API-101.107 (SEQ ID NO: 19) with twice the efficacy of the later. The compound API-101.109 (FIG. 20) also showed an improved potency in inhibiting PGE$_2$ (IC$_{50}$) (FIG. 19) but its K$_D$ is to high to be an efficient drug.

EXAMPLE 6

Efficacy of API-101.10, API-101.107 and API-101.113 in a Rat Model of Inflammatory Bowel Disease (IBD)

Further experiments were carried-out in order to verify if lead peptides TTI-101.10, previously termed API-101.10 (SEQ ID NO: 10), TTI-101.107 and TTI-101.113 (also termed 101.107 and 101.113, respectively; or API-101.107 and API-101.113, respectively) could prevent the inflammatory features on the animal IBD model described in Example 4. Colon inflammation was induced by intra-rectal/colon administration of the hapten trinitrobenzene sulphonic acid (TNBS) as described in Example 4. Two hours prior to TNBS administration, peptides, peptidomimetics or 0.9% saline were administered intravenously (iv) via the caudal vein (various concentrations of mg/kg/d) (total volume of 0.3 ml). For continous infusion, API-101.10 (or other peptides or peptidomimetics) (2.2 mg/kg, 4 times dose used for blood pressure experiments based on t½=2-3 h of various peptides) or 0.9% saline were then continuously infused using primed intraperitoneal alzet pumps. A third group (control) was not injected with TNBS. For intermittent administration, fifteen minutes after TNBS administration, 101.10 (0.25-1 mg/kg), 101.107 (0.2 mg/kg), 101.113 (0.05-1 mg/kg) were administered by intermittent intraperitoneal injection (ip). Also, these IL-1R antagonists were given twice a day (BID); Remicade® (anti-TNFα) (10 mg/kg) and dexamethasone (0.75 mg/kg) were administered intraperitoneally but only once a day (qd). The intrarectal administration (ir) of 101.10, 101.113 (1 and 2.5 mg/kg), and 5-ASA (50 mg/kg) was done one hour after TNBS administration, and twice a day, except for 5-ASA which is once a day. Finally, 101.10 (1-5 mg/kg) was also administered orally by gavage (po), twice a day. Forty-eight hours after administration of TNBS, rats were killed by CO$_2$ inhalation. Colon was removed and assessed macroscopically (adhesions, ulcerations, discoloration and bleeding) and histologically (neutrophil infiltration, epithelial injury, crypt distortion and ulcerations). One to seven animals per group were studied, according to treatments. Myeloperoxidase (MPO) activity was measured on tissue lysates.

Results:

As mentioned previously, The TNBS animal model is a valid in vivo model for inflammatory disease in humans, and more particularly of inflammatory bowel disease (IBD) since it reproduces the inflammatory characteristics and tissue injuries of Crohn's disease. As shown in Table 2, intraperitoneal continuous and intermittent injections of antagonists of the present invention (e.g. peptides, peptide derivatives and peptidomimetics) at different dosage prevented tissue damages due to inflammation such as formation of ulcers, loss of crypts and epithelium lining injury.

Animals that received intraperitoneal osmotic pumps (continuous infusion) containing 101.10 and 101.107 demonstrated marked reductions in MPO activity, macroscopic and histologic score, superior or equivalent in efficacy to Kineret (Table 2). Intermittent administration of 101.10, 101.107 (one concentration only) and 101.113 revealed a dose-dependent efficacy of twice a day administration which surpasses that observed with currently utilized agents for IBD, namely dexamethasone, Remicade® and 5-ASA. Macroscopic observation of colonic injuries were scored (4 blinded observers) and animals treated with peptides (BID) presented less adhesions and ulcerations (less than 50% compare to TNBS-treated animals). Animals also looked considerably more vigorous.

TABLE 2

Summary of in vivo results

| Treatment | dose (mg/kg/d) | n = | MPO (% of TNBS + Saline) | macroscopic evaluation (median score) | histologic evaluation (median score) |
|---|---|---|---|---|---|
| TNBS + Saline Continuous infusion (ip) | 120 mg/ml | 6 | 100 | 2/2 | 5/5 |
| TNBS + 101.10 | 0.25 | 2 | 34 | nd | 2 |
| TNBS + 101.10 | 0.75 | 2 | 54 | nd | 4.4 (n = 1) |
| TNBS + 101.10 | 2.2 | 3 | 46 ± 22 | nd | 2 (2) |
| TNBS + 101.10 | 4.0 | 2 | 82 | nd | 2 |
| TNBS + 101.107 | 0.5 | 2 | 37 | nd | 1.5 |
| TNBS + Kineret Intermittent injection ip) | 8.0 | 2 | 63 | nd | 2 |
| TNBS + 101.10 | 0.25-BID | 2 | 85 | 0.87 | 2.25 |
| TNBS + 101.10 | 0.50-BID | 2 | 126 | 0.87 | 3 |
| TNBS + 101.10 | 1.0-BID | 6 | 47 ± 9 | 0.8 ± 0.1 | 1.25 (1-2.8)** |
| TNBS + 101.10 | 1.0-qd | 2 | 67 | 1.63 | 5 |
| TNBS + 101.10 (12 h after TNBS) | 1.0-BID | 7 | 123 ± 18* | 1.1 ± 0.1 | 2.6 |
| TNBS + 101.107 | 0.2-BID | 2 | 112 | 1.37† | 2.5 |
| TNBS + 101.113 | 0.05-BID | 1 | 57 | 1.25† | nd |
| TNBS + 101.113 | 0.2-BID | 2 | 112 | 1.13 | 2.6 |
| TNBS + 101.113 | 0.5-BID | 1 | 45 | 0.75† | nd |
| TNBS + 101.113 | 1.0-BID | 1 | 67 | 1.75 | nd |
| TNBS + Saline Intermittent injection (ip) | 120 mg/ml | 6 | 100 | 2/2 | 5/5 |
| TNBS + Remicade | 10.0-qd | 3 | 88 ± 41 | 0.5 | 2.5 (1-3.75)** |
| TNBS + Dexamethasone Intrarectal administration | 0.75-qd | 2 | 60 | 0.87 | 3 |
| TNBS + 101.10 + PEG-400 | 1.0-BID | 2 | 110 | 1.25t | 3.2 |
| TNBS + 101.10 | 2.5-BID | 6 | 111 ± 25 | 1.4 ± 0.1 | nd |
| TNBS + 101.10 + PEG-400 | 2.5-BID | 2 | 59 | 1.17† | 3.9 |
| TNBS + 101.113 | 1.0-BID | 1 | 31 | 1.5 | nd |
| TNBS + 101.113 | 2.5-BID | 1 | 20 | 1.75 | nd |
| TNBS + 5-ASA Oral administration | 50.0-qd | 2 | 49 | 1.5 | 3.3 |
| TNBS + 101.10 | 5.0-BID | 1 | 65 | 0.75 | 2.25 |
| TNBS + 101.10 + PEG-400 | 1.0-BID | 2 | 167 | 1.0 | 3.5 |
| TNBS + 101.10 + PEG-400 | 2.5-BID | 2 | 176 | 1.25 | 3.5 |
| TNBS + 101.10 + PEG-400 | 5.0-BID | 2 | 57 | 1.5 | 3.6 | nd: not determined
*Note: leucocyte infiltration has already occurred
**Range
†Animals were considerably more vigorous

TABLE 3

Histological Injury Scoring System

| | Score |
|---|---|
| No injury | 1 |
| Small ulcer (<5 crypts) | 2 |
| Medium ulcer (5-10 crypts) | 3 |
| Large ulcer (10-20 crypts) | 4 |
| Marked denudation (>20 crypts) | 5 |

(adapted from Peterson et al., Dig Dis Sci, 2000)

FIG. 22 shows a graphical representation of the macroscopic scoring of every peptide for one particular concentration and the list of the evaluated features. Also, as may be seen in FIG. 23, animals treated with intermittent injections of peptides presented 20 to 50% less neutrophil infiltrations (myeloperoxidase assay) as compare to the TNBS control. Examination of histologic sections revealed that peptide-treated animals presented less characteristics of inflammation induced-colonic injury. The histological injury scoring system used is shown in Table 3, and the results are schematized in FIG. 24. Of course, other scoring systems could be used and adapted by the skilled artisan to which the present invention pertains. Hence, one may appreciate the reduction in the amount of ulcers and epithelial lining injury in Panel C and D of FIG. 25, as compared to Panel B representing the inflamed tissue. Furthermore, administration of the agents of the present inventions (e.g. peptide) 12 hours after the TNBS induction resulted in reduction of colonic inflammation also. The high myeloperoxidase activity remaining is due to the fact that neutrophil infiltration had already occurred before treatment.

In order to demonstrate that the peptide, and peptidomimetics of the present invention, can be administered by other means and reduce the inflammation generated with the TNBS, API-101.10 and API-101.113 were injected intrarectally. The inflammation level was assayed macroscopically and histologically as above. As may be seen in Table 2 API-101.10 at 2,5 mg/kg/d reduced substantially (50%) the MPO activity and partially prevented colonic tissues damages.

API-101.10 was also administrated by another means: gavage (twice a day) to demonstrate the stability of the peptide through the digestive tract. At the concentration of 5.0 mg/kg/d API-101.10 substantially reduces the inflammatory features as well as the MPO activity, thereby validating the stability of the compounds of the present invention.

EXAMPLE 7

TTI-101.107 Peptide Derivatives and Mimics

Using TTI-101.107 (SEQ ID NO: 19, and FIG. 15; IC$_{50}$ of 1.2 pM) as a lead peptide, several series of analogs were designed, synthesized and tested to establish the importance of each residue.
Structure vs Activity:

As may be seen in Table 4, when the terminal D-arginine was acetylated to give compound TTI-101.121 (SEQ ID NO: 29), the activity of the peptide was completely lost. On the other hand, the arginine residue may be replaced with ornithine or lysine and the resulting peptide maintains its activity (TTI-101.114, SEQ ID NO: 22; and TTI-101.115, SEQ ID NO: 23). It thus seems that the guanidine group of arginine (as with ornithine) may be important for peptide activity.

From data obtained by the replacements at the D-Threonine and D-valine residues previously shown above (see FIGS. 15 and 19) using peptides TTI-101.105 (SEQ ID NO: 17), and 101.106 (SEQ ID NO:18), and peptidomimetic TTI-101.109, a potential for a turn region about these residues was hypothesized and two peptides mimics were generated by introducing both (3R,6R,9R; TTI-101.110) and (3S,6S,9S; TTI-101.112)-indolizadin-2-one amino acids (R- and S-I2aa). These peptidomimetics shown in FIG. 26, mimic type II and type II' beta-turns, respectively. Peptidomimetic TTI-101.110 exhibited an activity of 10 pM (FIG. 26), comparable to that of peptide 101.107 from which it is derived.

The importance of the glutamate position was addressed using TTI-101.117 (SEQ ID NO: 25), TTI-101.118 (SEQ ID NO: 26) and TTI-101.123 (SEQ ID NO:31), in which glutamate is replaced with aspartate, asparagine and alanine, respectively. The results show (Table 4) that removing the carboxylate or carboxamide is deleterious for peptide function.

Examining the C-terminal D-leucinyl-D-alanine residues, a series of derivatives with deletions and substitutions were generated: TTI-101.113 (SEQ ID NO: 21); TTI-101.119 (SEQ ID NO: 27) and TTI-101.120 (SEQ ID NO:28). Deletion of the D-alanine residue gives rise to hexapeptide TTI-101.113 ((SEQ ID NO:21) Table 4) having a 7-30 pM activity. Modification of the leucine residue resulted in loss of activity range.

Based on the data shown above, two other mimetic compounds were synthesized (see FIG. 26): TTI-101.124 (ry[R-12aa]el (SEQ ID NO: 49) which showed an IC$_{50}$ of 2,4 µM and an efficacy of 100%; FIG. 26) and TTI-101.125 ((D-orn) y[R-12aa]ela (SEQ ID NO: 48) which showed an IC$_{50}$ of 90 pM and 100% efficacy; FIG. 26).
Derivatives of 101.113 Peptide Based on lead peptides (101.107 rytpela (SEQ ID NO: 19), 101.10 rytvela (SEQ ID NO: 10) and 101.113 rytpel (SEQ ID NO: 21), another series of analogs was made to examine further the structure-activity (structure-function relationship) relationship of the peptides and derivatives.

Exploring the importance of the basic amino acid terminal arginine, a series of analogs have shown that the activity was relatively diminished when the guanidine portion was replaced by a basic amine. Indeed, compounds TTI-101.126 (SEQ ID NO: 32), TTI-101.133 (SEQ ID NO: 37) and TTI-101.134 (SEQ ID NO: 38) exhibited little or no activity (Table 5). When the stereochemistry was inverted as in TTI-101.135 (SEQ ID NO: 39), in which the arginine "R" is an L-amino acid, as opposed to a D-amino acid in SEQ ID NO:21, the activity was lowered but not lost completely (Table 5).

As shown further in Table 5, the activity of the peptide 101.113 was also relatively decreased when the aromatic residue tyrosine, with its phenolic group, was replaced with aromatic residue phenylalanine (101.132; SEQ ID NO:36) or tryptophan (101.128; SEQ ID NO: 34). The removal of the hydroxyl group in TTI-101.127 (SEQ ID NO: 33) completely abolished the activity of the peptide, but the replacement of tyrosine with tryptophan lowered, but yet maintained the activity.

Replacing the C-terminal leucine by valine also caused a decrease in activity, demonstrating an importance of the length of the hydrophobic residue, as may be observed in Table 5 with TTI-101.129 (SEQ ID NO:35) (rytpev 400 nM; 50%).

Based on the lead peptidomimetic (TTI-101.125; FIG. 26) another series of mimetics was prepared to explore yet further the structure-activity of the compounds of the present invention.

Using aza-amino acid residues to respectively replace the tyrosine, the leucine and alanine residues, the series 101.136 to 101.140 and 101.141-101.144 were prepared (FIGS. 27 and 28). Because aza-amino acids can improve the resistance of peptides to enzymatic degradation, the maintenance of the activity in certain analogs exemplifies one means for increasing the duration of their in vivo action. These last modifications led to the development of compound TTI-101.140. FIGS. 29 and 30 show the structure and activity of the peptidomimetics 101.125, 101.136-101.144 and in particular the potency and efficiency of mimetic 101-140 which showed an increased activity.

TABLE 4

IL-1 β-induced proliferation and PGE$_2$ synthesis in presence of peptidomimetics (SEQ ID NOS: 21-31)

| Peptides | Sequence (SEQ ID NO:) | Proliferation in TF-1 cells (human) | | PGE2 synthesis in endothelial cells (porcine) | |
|---|---|---|---|---|---|
| | | IC$_{50}$ | Emax (%) | IC$_{50}$ | Emax (%) |
| 101.113 | rytpel (21) | 30 pM | 100 | 7.4 pM | 80 |
| 101.114 | kytpela (22) | nd | nd | 2 pM | 50 |
| 101.115 | [orn]ytpela (23) | ~1 pM | 100 | nd | nd |
| 101.116 | rwtpela (24) | 0.5 nM | 75 | 13 pM | 45 |
| 101.117 | rytpdla (25) | nd | nd | 10 pM | 100 |
| 101.118 | rytpqla (26) | nd | nd | nd | nd |
| 101.119 | rytpefa (27) | nd | nd | nd | nd |
| 101.120 | rytpema (28) | nd | nd | nd | nd |
| 101.121 | [Ac]rytpela (29) | nd | nd | nd | nd |
| 101.122 | rytpepa (30) | nd | nd | nd | nd |
| 101.123 | rytpala (31) | nd | nd | nd | nd |

TABLE 5

Characterization of 101.113 peptide derivatives IL-Iβ-induced TF-1 proliferation (SEQ ID NOS: 21 AND 32-39)

| Peptide | Sequence (SEQ ID NO:) | IC50 | Emax (%) |
|---|---|---|---|
| 101.113 | rytpel (21) | 7 pM | 70 |
| 101.126 | [Orn]ytpel (32) | * | 0 |
| 101.127 | rfvpela (33) | nd | <30 |
| 101.128 | rwtpel (34) | 3 nM | 100 |

TABLE 5-continued

Characterization of 101.113 peptide derivatives IL-1β-induced TF-1 proliferation (SEQ ID NOS: 21 AND 32-39)

| Peptide | Sequence (SEQ ID NO:) | IC50 | Emax (%) |
|---|---|---|---|
| 101.129 | rytpev (35) | 400 nM | 50 |
| 101.132 | rftpel (36) | 4 nM | 35 |
| 101.133 | kytpel (37) | nd | <10 |
| 101.134 | [Cit]ytpel (38) | 10 μM | 10 |
| 101.135 | Rytpel (39) | 2 nM | 63 |

*Could not be determined
The "R" denotes an L-aa

CONCLUSIONS

In summary, the present invention describes efficient and potent antagonists of IL-1R/IL-1RacP receptor that can abrogate the biological effects of the interleukin-1 both in vitro, ex vivo and in vivo. These peptides were effective in vitro on different cell types and against different biological effects (proliferation and PGE$_2$ synthesis), ex vivo by abolishing the vasomotor effect of IL-1 on pial vessels and PGE$_2$ synthesis on fresh sample tissues. Moreover these API-101 derivatives were also very effective in vivo when administrated systemically and directly into the stomach. The last result obtained with the stomach delivery show that the peptides of the present invention have the potential of being active when administered orally. This was indeed demonstrated when gavage was used. More importantly, in an established rat model of Inflammatory Bowel Disease (IBD), API-101.10 could prevent colon damages induced by injection of TNBS in rat. Based on the results with other derivatives (in the 101.100 series), it has been demonstrated that these peptide derivatives and peptidomimetics thereof are potent anti-inflammatory agents, as demonstrated by their role in preventing colon damage induced by injection of TNBS in rat.

The present invention shows that the peptides and peptidomimetics of the present invention have clear effects on a number of pathways involving IL-1R/IL-1RacP. The therapeutic and prophylactic potential of the present invention has therefore broad impacts for animals in general and more particularly for mammals and especially for humans.

Based on the disclosure herein, those skilled in the art can develop peptides, peptide derivatives and peptidomimetics screening assays which are useful for identifying further IL-1R/IL-1RacP receptor inhibiting compounds or improve those exemplified herein. The assays of the present invention may be developed. for low-throughput, high-throughput, or ultra-high throughput screening formats. Of course, assays of the present invention include assays that are amenable to automation.

Thus, working with peptides possessing natural amino acids, the present invention demonstrate that they are potent and efficacious compounds in vitro and in vivo studies (e.g. TTI-101.107 (SEQ ID NO: 19 and 113 [SEQ ID NO:21]). Furthermore, the present invention provides an initial description of the pharmacophore and conformation necessary for activity and the peptides and mimetics derived therefrom.

Of note, the invention provides a hexapeptide lead: TTI-101.113 (rytpel ([SEQ ID NO:21] having a very significant activity (7.4 pM; 80% efficacy). Further mimics or mimetics were generated with indolizadinone amino acid to replace the central D-threonine-d-valine(D-Pro) region thereby enabling the identification of lead mimics TTI-101.125 and TTI-101.140.

Of course the combination of antagonists of the present invention or a combination thereof with known drugs could further increase the medical, clinical and drug development potential of the present invention.

Although the present invention has been described hereinabove by way of illustrative embodiments thereof, it will be appreciated by one skilled in the art from reading of this disclosure that various changes in form and detail can be made without departing from the spirit and scope of the invention as defined in the appended claims.

REFERENCES

Anthony D., Savage F. et al, (1995). "The characterization of a rabbit model of inflammatory bowel disease." Int. J. Exp. Path 76 :215-224.

Asadullah K, Sabat R, Friedrich M, Volk H D, Sterry W. Interleukin-10: an important immunoregulatory cytokine with major impact on psoriasis. Curr Drug Targets Inflamm Allergy. 2004 June; 3(2):185-92

Barnstable C J, Tombran-Tink J. Neuroprotective and antiangiogenic actions of PEDF in the eye: molecular targets and therapeutic potential. Prog. Retin Eye Res. 2004. September 23(5) 561-77.

Baker, F. L., L. J. Sanger, et al. (1995). "Cell proliferation kinetics of normal and tumour tissue in vitro: quiescent reproductive cells and the cycling reproductive fraction." Cell Prolif 28(1): 1-15.

Beauchamp, M. H., A. K. Martinez-Bermudez, et al. (2001). "Role of thromboxane in retinal microvascular degeneration in oxygen-induced retinopathy." J Appl Physiol 90(6): 2279-88.

Bouma, G. and W. Strober (2003). "The immunological and genetic basis of inflammatory bowel disease." Nat Rev Immunol 3(7): 521-33.

Brady, L. and G. Dodson (1994). "Drug design. Reflections on a peptide." Nature 368(6473): 692-3.

Brault, S., A. K. Martinez-Bermudez, et al., (2003). "Selective neuromicrovascular endothelial cell death by 8-Isoprostaglandin F2alpha: possible role in ischemic brain injury." Stroke 34(3): 776-82.

Casadio, R., E. Frigimelica, et al. (2001). "Model of interaction of the IL-1 receptor accessory protein IL-1RAcP with the IL-1 beta/IL-1R(I) complex." FEBS Lett 499(1-2): 65-8.

Cheviron, N., C. Grillon, et al. (1996). "The antiproliferative activity of the tetrapeptide Acetyl-N-SerAspLysPro, an inhibitor of haematopoietic stem cell proliferation, is not mediated by a thymosin beta 4-like effect on actin assembly." Cell Prolif 29(8): 437-46.

Cluzeau, J and Lubell W D. (2004. "Conformationally constrained dipeptide Surrogates with Aromatic Side-Chains: Synthesis of 4-Aryl lndolizidin-9-one Intermediate". J. Org. Chem. 69: 1504-1512.

Cullinan, E. B., L. Kwee, et al. (1998). "IL-1 receptor accessory protein is an essential component of the IL-1 receptor." J Immunol 161(10): 5614-20.

Daun J M, Fenton, M J. Interleukin-1/Toll receptor family members: receptor structure and sighanl transduction pathways. J. Interferon Cytokine Res. 2000 October, 20 (10); 843-55.

Dettwiler, J. E. and Lubell, W. D.; J. Org. Chem., 2003, 68, 177-179.

Dieleman L A., Pena A S. et al. (1997). Role of Animal Models for the pathogenesis and treatment of inflammatory bowel disease. *Scand. J Gastroenterol.* 32 Suppl 223: 99-104.

Dietrich, E and Lubell W D. (2003). "Efficient Synthesis of Enantipure Pyrrolizidinone Amino Acid" J. Org. Chem. 68: 6988-6996.

Dunne, A. and L. A. O'Neill (2003). "The interleukin-1 receptor/Toll-like receptor superfamily: signal transduction during inflammation and host defense." *Sci STKE* 2003(171): re3.

Elliott, K., D. Sakamuro, et al. (1999). "Bin1 functionally interacts with Myc and inhibits cell proliferation via multiple mechanisms." *Oncogene* 18(24): 3564-73.

Feng Z, Lubell W D. (2001) "Mimicry of peptide Back-bone geometry and heteroatomic side-chain functionality: Synthesis of 7-[3-Azidopropyl]indolizidin-2-one amino acid as a constrained Ala-Lys dipeptide Surrogate" J. Org. Chem 66: 1181-1185.

Gabay, C. (2000). "IL-1 inhibitors: novel agents in the treatment of rheumatoid arthritis." *Expert Opin Investig Drugs* 9(1): 113-27.

Gosselin F and Lubell W D. (1998). "An olefination entry for the synthesis of enantiopure a,w-diamino-dicarboxylates and azabicyclo[X.Y.O]alkane amino acids." J. Org. Chem. 63: 7463-71

Gosselin F and Lubell W D. (2000). "Rigid Dipeptide Surrogates: Suntheses of Enantiopure Quinolozidinone and Pyrroloazepinone Amino Acids from a Common Diaminodicarboxylate Precursor". J. Org. Chem. 65: 2163-2171.

Halab, L. et al. (2000). "Design, synthesis and conformational Analysis of Azacycloalkane amino acids as conformationally constrianed probes for mimicry of peptide secondary structures." Biopolymers, Peptide Science 55:101-22.

Hallegua, D. S. and M. H. Weisman (2002). "Potential therapeutic uses of interleukin 1 receptor antagonists in human diseases." *Ann Rheum Dis* 61(11): 960-7.

Hanessian S, McNaughton-Smith et al. (1997) "Design and synthesis of conformationally constrained amino acids as versatile scaffolds and peptide mimetics". Tetrahedron. 53: 12789-12854.

Hardy, P., A. M. Nuyt, et al. (1999). "Developmentally increased cerebrovascular NO in newborn pigs curtails cerebral blood flow autoregulation." *Pediatr Res* 46(4): 375-82.

Hou, X., F. Gobeil, Jr., et al. (2003). "Increased platelet-activating factor-induced periventricular brain microvascular constriction associated with immaturity." *Am J Physiol Regul Integr Comp Physiol* 284(4): R928-35.

Hou, X., F. Gobeil, Jr., et al. (2000). "Augmented vasoconstriction and thromboxane formation by 15-F(2t)-isoprostane (8-iso-prostaglandin F(2alpha)) in immature pig periventricular brain microvessels." *Stroke* 31(2): 516-24; discussion 525.

Hou, X., L. J. Roberts, 2nd, et al. (2001). "2,3-Dinor-5,6-dihydro-15-F(2t)-isoprostane: a bioactive prostanoid metabolite." *Am J Physiol Regul Integr Comp Physiol* 281 (2): R391-400.

Hu, Z. W., X. Y. Shi, et al. (1999). "alpha1-Adrenergic receptor stimulation of mitogenesis in human vascular smooth muscle cells: role of tyrosine protein kinases and calcium in activation of mitogen-activated protein kinase." *J Pharmacol Exp Ther* 290(1): 28-37.

Jameson, B. A., J. M. McDonnell, et al., (1994). "A rationally designed CD4 analogue inhibits experimental allergic encephalomyelitis." *Nature* 368(6473): 744-6.

Kashiwamura, S. Ueda, H. and Okamura, H. (2002) "Roles of interleukin-18 in tissue destruction and compensatory reactions. J Immunother 25 Suppl, S4-11.

Kumar, S., P. C. McDonnell, et al. (2000). "Identification and initial characterization of four novel members of the interleukin-1 family." *J Biol Chem* 275(14): 10308-14.

Lapatsanis, L.; Milias, G.; Froussios, K.; Kolovos, M. *Synthesis,* 1983, 671-673.

Laye, S., J. Lundkvist, et al., (1998). "Human/mouse interleukin-1 receptor/receptor accessory protein interactions in IL-1 beta-induced NFkappaB activation." *FEBS Lett* 429(3): 307-11.

Li, D. Y., P. Hardy, et al. (1997). "Key role for cyclooxygenase-2 in PGE2 and PGF2alpha receptor regulation and cerebral blood flow of the newborn." *Am J Physiol* 273(4 Pt 2): R1283-90.

Li M C, He SH.IL-10 and its related cytokines for treatment of inflammatory bowel disease. World J Gastroenterol. 2004 Mar. 1; 10(5):620-5.

Lombart, H.-G. and Lubell, W. D.; *J. Org. Chem.,* 1996, 61, 9437-9446.

Malinowsky, D., J. Lundkvist, et al. (1998). "Interleukin-1 receptor accessory protein interacts with the type II interleukin-1 receptor." *FEBS Lett* 429(3): 299-302.

Masic L P and Kikelj D. (2001). Tetrahedron 57: 7073.

Meienhofer, J.; Waki, M.; Heimer, E. P.; Lambros, T. J.; Makofske, R. C.; Chang, C. D.; *Int. J. Pept. Protein Res.,* 1979, 13, 35-42.

Merrifield, R. B. (1964). "Solid-Phase Peptide Synthesis. 3. An Improved Synthesis of Bradykinin." Biochemistry 14: 1385-90.

Najarian, T., A. M. Marrache, et al. (2000). "Prolonged hypercapnia-evoked cerebral hyperemia via K(+) channel- and prostaglandin E(2)-dependent endothelial nitric oxide synthase induction." *Circ Res* 87(12): 1149-56.

Padol I., Huang, J Q. et al. (2000). Therapeutic effects of the endothelin receptor antagonist Ro 48-5695 in the TNBS/DNBS rat model of colitis. *Eur J of Gastroenterol Hepatol.* 12:257-265.

Pascal, R. and Sola, R.; Terahedron. Lett., 1998, 39, 5031-5034.

PolyaK F, Lubell W D. (1998). "Rigid dipeptide mimics: synthesis of enantiopure enolization and alkylation of d-Oxo a,w-Di-[N-(9-(9-phenylfluorenyl))amino]azelate Esters." *J. Org. Chem.* 63: 5937-5949.

Polyak, F, Lubell W D. "Mimicry of peptides back-bone geometry and heteroatomic side-chain functionality: Synthesis of Enantiopure Indolizidin-2-one Amino Acids possessing Alcohol, Acid and Amine Functional Groups" J. Org. Chem. 66:1171-1180

Powell, M. F., T. Stewart, et al. (1993). "Peptide stability in drug development. II. Effect of single amino acid substitution and glycosylation on peptide reactivity in human serum." Pharm Res 10(9): 1268-73.

Schuerwegh, A J et al. Influence of pro-inflammatory (IL-1, IL-6, THF-alpha, IFN-gamma) and anti-inflammatory (114) cytokines on chondrocytes function.

Sims, J. E. "IL-1 and IL-18 receptors, and their extended families." Curren Opin in Immunology 2002. February 14(1)117-122.

Sims, J. E., R. B. Acres, et al. (1989). "Cloning the interleukin 1 receptor from human T cells." *Proc Natl Acad Sci USA* 86(22): 8946-50.

Torres M I, Garcia-Martin M., et al., (1999). Experimenta colitis induced by trinitrobenzenesulfonic acid. An ultrastructural and histochemical study. *Digestive Diseases and Sciences.* 44: No. 12: 2523-2529.

Vigers, G. P., L. J. Anderson, et al. (1997). "Crystal structure of the type-I interleukin-1 receptor complexed with interleukin-1beta." *Nature* 386(6621): 190-4.

Vigers, G. P., D. J. Dripps, et al. (2000). "X-ray crystal structure of a small antagonist peptide bound to interleukin-1 receptor type 1." *J Biol Chem* 275(47): 36927-33.

What is claimed is:

1. A peptide that is:
   (a) 5 to 16 amino acids long and has an amino acid sequence selected from the group consisting of: RYTPEL (SEQ ID NO:21), RYTVQLA (SEQ ID NO:15), KYTPELA (SEQ ID NO:22), RYTPDLA (SEQ ID NO:25), RYVVELA (SEQ ID NO:18), RWTPELA (SEQ ID NO:24), RYTPEL (SEQ ID NO:39), RWTPEL (SEQ ID NO:34), APRYTVALA (SEQ ID NO:7), RYTPEV (SEQ ID NO:35), and RFTPEL (SEQ ID NO:36); or
   (b) 5 to 9 amino acids long and has an amino acid sequence selected from the group consisting of RYTVELA (SEQ ID NO:10), RYTVEL (SEQ ID NO:20), PRYTVELA (SEQ ID NO:9), YTVELA (SEQ ID NO:11), and TVELA (SEQ ID NO:12).

2. The peptide of claim 1, wherein the peptide has an amino acid sequence selected from the group consisting of: RYTPEL (SEQ ID NO:21), RYTVQLA (SEQ ID NO:15), KYTPELA (SEQ ID NO:22), and RYTPDLA (SEQ ID NO:25).

3. The peptide of claim 1, wherein the peptide consists of the amino acid sequence RYTVELA (SEQ ID NO:10).

4. A method for treating an IL-1-related disease, disorder or condition in an animal comprising: administering to said animal a therapeutically effective amount of a peptide according to claim 1, wherein the IL-1-related disease, disorder or condition is an inflammatory bowel disease, an inflammatory joint disease or psoriasis.

5. A pharmaceutical composition comprising at least one peptide of claim 1 and a pharmaceutically acceptable excipient.

6. The method of claim 4, wherein the IL-1-related disease, disorder or condition is an inflammatory bowel disease.

7. The method of claim 1, wherein said animal is a human patient.

8. The peptide of claim 1, wherein the amino acid sequence contains at least one D-amino acid.

9. The peptide of claim 1, wherein said peptide contains amino acids selected from the group consisting of L-amino acid, D-amino acid, and a mixture thereof.

10. The peptide of claim 1, wherein the amino acid sequence comprises one or more modifications to increase protease resistance, serum stability and/or bioavailability.

11. The method of claim 6, wherein the inflammatory bowel disease is Crohn's disease.

12. The method of claim 6, wherein the inflammatory bowel disease is ulcerative colitis.

13. The method of claim 4, wherein the IL-1-related disease, disorder or condition is an inflammatory joint disease.

14. The method of claim 13, wherein the inflammatory joint disease is rheumatoid arthritis.

15. The method of claim 13, wherein the inflammatory joint disease is osteoarthritis.

16. The method of claim 4, wherein the IL-1-related disease, disorder or condition is psoriasis.

* * * * *

SEQUENCE LISTING

```
<160> NUMBER OF SEQ ID NOS: 49

<210> SEQ ID NO 1
<211> LENGTH: 9
<212> TYPE: PRT
<213> ORGANISM: Artificial
<220> FEATURE:
<223> OTHER INFORMATION: Synthetic construct

<400> SEQUENCE: 1

Ala Pro Arg Tyr Thr Val Glu Leu Ala
1               5

<210> SEQ ID NO 2
<211> LENGTH: 9
<212> TYPE: PRT
<213> ORGANISM: Artificial
<220> FEATURE:
<223> OTHER INFORMATION: Synthetic construct

<400> SEQUENCE: 2

Ala Ala Arg Tyr Thr Val Glu Leu Ala
1               5

<210> SEQ ID NO 3
<211> LENGTH: 9
<212> TYPE: PRT
<213> ORGANISM: Artificial
<220> FEATURE:
<223> OTHER INFORMATION: Synthetic construct

<400> SEQUENCE: 3

Ala Pro Ala Tyr Thr Val Glu Leu Ala
1               5

<210> SEQ ID NO 4
<211> LENGTH: 9
<212> TYPE: PRT
<213> ORGANISM: Artificial
<220> FEATURE:
<223> OTHER INFORMATION: Synthetic construct

<400> SEQUENCE: 4

Ala Pro Arg Ala Thr Val Glu Leu Ala
1               5

<210> SEQ ID NO 5
<211> LENGTH: 9
<212> TYPE: PRT
<213> ORGANISM: Artificial
<220> FEATURE:
<223> OTHER INFORMATION: Synthetic construct

<400> SEQUENCE: 5

Ala Pro Arg Tyr Ala Val Glu Leu Ala
1               5

<210> SEQ ID NO 6
<211> LENGTH: 9
<212> TYPE: PRT
<213> ORGANISM: Artificial
<220> FEATURE:
```

<223> OTHER INFORMATION: Synthetic construct

<400> SEQUENCE: 6

Ala Pro Arg Tyr Thr Ala Glu Leu Ala
1               5

<210> SEQ ID NO 7
<211> LENGTH: 9
<212> TYPE: PRT
<213> ORGANISM: Artificial
<220> FEATURE:
<223> OTHER INFORMATION: Synthetic construct

<400> SEQUENCE: 7

Ala Pro Arg Tyr Thr Val Ala Leu Ala
1               5

<210> SEQ ID NO 8
<211> LENGTH: 9
<212> TYPE: PRT
<213> ORGANISM: Artificial
<220> FEATURE:
<223> OTHER INFORMATION: Synthetic construct

<400> SEQUENCE: 8

Ala Pro Arg Tyr Thr Val Glu Ala Ala
1               5

<210> SEQ ID NO 9
<211> LENGTH: 8
<212> TYPE: PRT
<213> ORGANISM: Artificial
<220> FEATURE:
<223> OTHER INFORMATION: Synthetic construct

<400> SEQUENCE: 9

Pro Arg Tyr Thr Val Glu Leu Ala
1               5

<210> SEQ ID NO 10
<211> LENGTH: 7
<212> TYPE: PRT
<213> ORGANISM: Artificial
<220> FEATURE:
<223> OTHER INFORMATION: Synthetic construct

<400> SEQUENCE: 10

Arg Tyr Thr Val Glu Leu Ala
1               5

<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Tyr Thr Val Glu Leu Ala
1               5

<210> SEQ ID NO 12
<211> LENGTH: 5
<212> TYPE: PRT
<213> ORGANISM: Artificial
<220> FEATURE:
<223> OTHER INFORMATION: Synthetic construct

```
<400> SEQUENCE: 12

Thr Val Glu Leu Ala
1               5

<210> SEQ ID NO 13
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Citrulline

<400> SEQUENCE: 13

Xaa Tyr Thr Val Glu Leu Ala
1               5

<210> SEQ ID NO 14
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Citrulline

<400> SEQUENCE: 14

Xaa Tyr Thr Val Gln Leu Ala
1               5

<210> SEQ ID NO 15
<211> LENGTH: 7
<212> TYPE: PRT
<213> ORGANISM: Artificial
<220> FEATURE:
<223> OTHER INFORMATION: Synthetic construct

<400> SEQUENCE: 15

Arg Tyr Thr Val Gln Leu Ala
1               5

<210> SEQ ID NO 16
<211> LENGTH: 7
<212> TYPE: PRT
<213> ORGANISM: Artificial
<220> FEATURE:
<223> OTHER INFORMATION: Synthetic construct

<400> SEQUENCE: 16

Arg Phe Thr Val Glu Leu Ala
1               5

<210> SEQ ID NO 17
<211> LENGTH: 7
<212> TYPE: PRT
<213> ORGANISM: Artificial
<220> FEATURE:
<223> OTHER INFORMATION: Synthetic construct

<400> SEQUENCE: 17

Arg Tyr Ser Val Glu Leu Ala
1               5

<210> SEQ ID NO 18
```

```
<211> LENGTH: 7
<212> TYPE: PRT
<213> ORGANISM: Artificial
<220> FEATURE:
<223> OTHER INFORMATION: Synthetic construct

<400> SEQUENCE: 18

Arg Tyr Val Val Glu Leu Ala
1               5

<210> SEQ ID NO 19
<211> LENGTH: 7
<212> TYPE: PRT
<213> ORGANISM: Artificial
<220> FEATURE:
<223> OTHER INFORMATION: Synthetic construct

<400> SEQUENCE: 19

Arg Tyr Thr Pro Glu Leu Ala
1               5

<210> SEQ ID NO 20
<211> LENGTH: 6
<212> TYPE: PRT
<213> ORGANISM: Artificial
<220> FEATURE:
<223> OTHER INFORMATION: Synthetic construct

<400> SEQUENCE: 20

Arg Tyr Thr Val Glu Leu
1               5

<210> SEQ ID NO 21
<211> LENGTH: 6
<212> TYPE: PRT
<213> ORGANISM: Artificial
<220> FEATURE:
<223> OTHER INFORMATION: Synthetic construct

<400> SEQUENCE: 21

Arg Tyr Thr Pro Glu Leu
1               5

<210> SEQ ID NO 22
<211> LENGTH: 7
<212> TYPE: PRT
<213> ORGANISM: Artificial
<220> FEATURE:
<223> OTHER INFORMATION: Synthetic construct

<400> SEQUENCE: 22

Lys Tyr Thr Pro Glu Leu Ala
1               5

<210> SEQ ID NO 23
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Ornithine

<400> SEQUENCE: 23

Xaa Tyr Thr Pro Glu Leu Ala
1               5
```

```
<210> SEQ ID NO 24
<211> LENGTH: 7
<212> TYPE: PRT
<213> ORGANISM: Artificial
<220> FEATURE:
<223> OTHER INFORMATION: Synthetic construct

<400> SEQUENCE: 24

Arg Trp Thr Pro Glu Leu Ala
1               5

<210> SEQ ID NO 25
<211> LENGTH: 7
<212> TYPE: PRT
<213> ORGANISM: Artificial
<220> FEATURE:
<223> OTHER INFORMATION: Synthetic construct

<400> SEQUENCE: 25

Arg Tyr Thr Pro Asp Leu Ala
1               5

<210> SEQ ID NO 26
<211> LENGTH: 7
<212> TYPE: PRT
<213> ORGANISM: Artificial
<220> FEATURE:
<223> OTHER INFORMATION: Synthetic construct

<400> SEQUENCE: 26

Arg Tyr Thr Pro Gln Leu Ala
1               5

<210> SEQ ID NO 27
<211> LENGTH: 7
<212> TYPE: PRT
<213> ORGANISM: Artificial
<220> FEATURE:
<223> OTHER INFORMATION: Synthetic construct

<400> SEQUENCE: 27

Arg Tyr Thr Pro Glu Phe Ala
1               5

<210> SEQ ID NO 28
<211> LENGTH: 7
<212> TYPE: PRT
<213> ORGANISM: Artificial
<220> FEATURE:
<223> OTHER INFORMATION: Synthetic construct

<400> SEQUENCE: 28

Arg Tyr Thr Pro Glu Met Ala
1               5

<210> SEQ ID NO 29
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Acetyl-Arg

<400> SEQUENCE: 29

Arg Tyr Thr Pro Glu Leu Ala
```

```
<210> SEQ ID NO 30
<211> LENGTH: 7
<212> TYPE: PRT
<213> ORGANISM: Artificial
<220> FEATURE:
<223> OTHER INFORMATION: Synthetic construct

<400> SEQUENCE: 30

Arg Tyr Thr Pro Glu Pro Ala
1               5

<210> SEQ ID NO 31
<211> LENGTH: 7
<212> TYPE: PRT
<213> ORGANISM: Artificial
<220> FEATURE:
<223> OTHER INFORMATION: Synthetic construct

<400> SEQUENCE: 31

Arg Tyr Thr Pro Ala Leu Ala
1               5

<210> SEQ ID NO 32
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Ornithine

<400> SEQUENCE: 32

Xaa Tyr Thr Pro Glu Leu
1               5

<210> SEQ ID NO 33
<211> LENGTH: 7
<212> TYPE: PRT
<213> ORGANISM: Artificial
<220> FEATURE:
<223> OTHER INFORMATION: Synthetic construct

<400> SEQUENCE: 33

Arg Phe Val Pro Glu Leu Ala
1               5

<210> SEQ ID NO 34
<211> LENGTH: 6
<212> TYPE: PRT
<213> ORGANISM: Artificial
<220> FEATURE:
<223> OTHER INFORMATION: Synthetic construct

<400> SEQUENCE: 34

Arg Trp Thr Pro Glu Leu
1               5

<210> SEQ ID NO 35
<211> LENGTH: 6
<212> TYPE: PRT
<213> ORGANISM: Artificial
<220> FEATURE:
<223> OTHER INFORMATION: Synthetic construct

<400> SEQUENCE: 35
```

```
Arg Tyr Thr Pro Glu Val
1               5

<210> SEQ ID NO 36
<211> LENGTH: 6
<212> TYPE: PRT
<213> ORGANISM: Artificial
<220> FEATURE:
<223> OTHER INFORMATION: Synthetic construct

<400> SEQUENCE: 36

Arg Phe Thr Pro Glu Leu
1               5

<210> SEQ ID NO 37
<211> LENGTH: 6
<212> TYPE: PRT
<213> ORGANISM: Artificial
<220> FEATURE:
<223> OTHER INFORMATION: Synthetic construct

<400> SEQUENCE: 37

Lys Tyr Thr Pro Glu Leu
1               5

<210> SEQ ID NO 38
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Citrulline

<400> SEQUENCE: 38

Xaa Tyr Thr Pro Glu Leu
1               5

<210> SEQ ID NO 39
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = L-Arginine

<400> SEQUENCE: 39

Xaa Tyr Thr Pro Glu Leu
1               5

<210> SEQ ID NO 40
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa = Ala or is absent

<400> SEQUENCE: 40

Arg Tyr Thr Pro Glu Leu Xaa
1               5
```

```
<210> SEQ ID NO 41
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Leucine, Valine, Methionine, Alanine,
      Norleucine, Isoleucine or is absent
<220> FEATURE:
<221> NAME/KEY: MISC_FEATURE
<222> LOCATION: (2)..(2)
<223> OTHER INFORMATION: Xaa = Alanine, Proline, aminoisobutyric acid or
      is absent
<220> FEATURE:
<221> NAME/KEY: MISC_FEATURE
<222> LOCATION: (3)..(3)
<223> OTHER INFORMATION: Xaa = Histidine, Lysine, Alanine, Arginine,
      Ornithine or is absent
<220> FEATURE:
<221> NAME/KEY: MISC_FEATURE
<222> LOCATION: (4)..(4)
<223> OTHER INFORMATION: Xaa = Phenylalanine, Tyrosine, Alanine,
      Tryptophan, Histidine, Norleucine, Isoleucine, an alpha-amino acid
      having a hydrophobic side chain or is absent
<220> FEATURE:
<221> NAME/KEY: MISC_FEATURE
<222> LOCATION: (5)..(5)
<223> OTHER INFORMATION: Xaa = Threonine, Serine, Valine,
      Hydroxyproline, or a neutral Hydrophilic amino acid
<220> FEATURE:
<221> NAME/KEY: MISC_FEATURE
<222> LOCATION: (6)..(6)
<223> OTHER INFORMATION: Xaa = Isoleucine, Leucine, Valine, Proline,
      Methionine, Hydroxyproline, or an alpha-amino acid having a
      hydrophobic side chain
<220> FEATURE:
<221> NAME/KEY: MISC_FEATURE
<222> LOCATION: (7)..(7)
<223> OTHER INFORMATION: Xaa = Aspartic Acid, Asparagine, Glutamic Acid,
      Glutamine, Serine, or Histidine
<220> FEATURE:
<221> NAME/KEY: MISC_FEATURE
<222> LOCATION: (8)..(8)
<223> OTHER INFORMATION: Xaa = Alanine, Valine, Isoleucine, Leucine,
      Methionine, Phenylalanine, Tryptophan, Norleucine, Isoleucine, or
      a neutral aliphatic amino acid
<220> FEATURE:
<221> NAME/KEY: MISC_FEATURE
<222> LOCATION: (9)..(9)
<223> OTHER INFORMATION: Xaa = Alanine, Valine, Isoleucine, Leucine,
      Methionine, Phenylalanine, Tryptophan, a neutral aliphatic amino
      acid or is absent

<400> SEQUENCE: 41

Xaa Xaa Xaa Xaa Xaa Xaa Xaa Xaa Xaa
1               5

<210> SEQ ID NO 42
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Leucine, Valine, Methionine, Alanine,
      Norleucine, Isoleucine or is absent
<220> FEATURE:
<221> NAME/KEY: MOD_RES
<222> LOCATION: (1)..(1)
<223> OTHER INFORMATION: attachment of a hydrogen, a straight chained or
      branched alkyl group of 1-8 carbons, an RCO - group, where R is a
```

-continued

```
      straight chained or branched alkyl group of 1-8 carbons, a
      tertiary amine, propianoyl, butanoyl, isopropianoyl, isobutanoyl
      or no residue
<220> FEATURE:
<221> NAME/KEY: MISC_FEATURE
<222> LOCATION: (2)..(2)
<223> OTHER INFORMATION: Xaa = Proline, Alanine, Aminoisobutyric Acid or
      is absent
<220> FEATURE:
<221> NAME/KEY: MISC_FEATURE
<222> LOCATION: (3)..(3)
<223> OTHER INFORMATION: Xaa = Histidine, Lysine, Alanine, Arginine,
      Ornithine or is absent
<220> FEATURE:
<221> NAME/KEY: MISC_FEATURE
<222> LOCATION: (4)..(4)
<223> OTHER INFORMATION: Xaa = Phenylalanine, Tyrosine, Alanine,
      Tryptophan, Histidine, Norleucine, Isoleucine, an alpha-amino acid
      having a hydrophobic side chain or is absent
<220> FEATURE:
<221> NAME/KEY: MISC_FEATURE
<222> LOCATION: (5)..(5)
<223> OTHER INFORMATION: Xaa = Threonine, Serine, Valine,
      Hydroxyproline, or a neutral Hydrophilic amino acid
<220> FEATURE:
<221> NAME/KEY: MISC_FEATURE
<222> LOCATION: (6)..(6)
<223> OTHER INFORMATION: Xaa = Isoleucine,Leucine, Valine, Proline,
      Methionine, Hydroxyproline, or an alpha-amino acid having a
      hydrophobic side chain
<220> FEATURE:
<221> NAME/KEY: MISC_FEATURE
<222> LOCATION: (7)..(7)
<223> OTHER INFORMATION: Xaa = Aspartic Acid, Asparagine, Glutamic Acid,
      Glutamine, Serine, or Histidine
<220> FEATURE:
<221> NAME/KEY: MISC_FEATURE
<222> LOCATION: (8)..(8)
<223> OTHER INFORMATION: Xaa = Alanine, Valine, Isoleucine, Leucine,
      Methionine, Phenylalanine, Tryptophan, Norleucine, Isoleucine, or
      a neutral aliphatic amino acid
<220> FEATURE:
<221> NAME/KEY: MISC_FEATURE
<222> LOCATION: (9)..(9)
<223> OTHER INFORMATION: Xaa = Alanine, Valine, Isoleucine, Leucine,
      Methionine, Phenylalanine, Tryptophan, a neutral aliphatic amino
      acid or is absent

<400> SEQUENCE: 42

Xaa Xaa Xaa Xaa Xaa Xaa Xaa Xaa Xaa
1               5

<210> SEQ ID NO 43
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Leucine, Valine, Methionine, Alanine,
      Norleucine, Isoleucine or is absent
<220> FEATURE:
<221> NAME/KEY: MISC_FEATURE
<222> LOCATION: (2)..(2)
<223> OTHER INFORMATION: Xaa = Proline, Alanine, Aminoisobutyric Acid or
      is absent
<220> FEATURE:
<221> NAME/KEY: MISC_FEATURE
<222> LOCATION: (3)..(3)
<223> OTHER INFORMATION: Xaa = Histidine, Lysine, Alanine, Arginine,
      Ornithine or is absent
<220> FEATURE:
<221> NAME/KEY: MISC_FEATURE
<222> LOCATION: (4)..(4)
<223> OTHER INFORMATION: Xaa = Phenylalanine, Tyrosine, Alanine,
      Tryptophan, Histidine, Norleucine, Isoleucine, an alpha-amino acid
```

```
      having a hydrophobic side chain or is absent
<220> FEATURE:
<221> NAME/KEY: MISC_FEATURE
<222> LOCATION: (5)..(5)
<223> OTHER INFORMATION: Xaa = Threonine, Serine, Valine,
      Hydroxyproline, or a neutral Hydrophilic amino acid
<220> FEATURE:
<221> NAME/KEY: MISC_FEATURE
<222> LOCATION: (6)..(6)
<223> OTHER INFORMATION: Xaa = Isoleucine,Leucine, Valine, Proline,
      Methionine, Hydroxyproline, or an alpha-amino acid having a
      hydrophobic side chain
<220> FEATURE:
<221> NAME/KEY: MISC_FEATURE
<222> LOCATION: (7)..(7)
<223> OTHER INFORMATION: Xaa = Aspartic Acid, Asparagine, Glutamic Acid,
      Glutamine, Serine, or Histidine
<220> FEATURE:
<221> NAME/KEY: MISC_FEATURE
<222> LOCATION: (8)..(8)
<223> OTHER INFORMATION: Xaa = Alanine, Valine, Isoleucine, Leucine,
      Methionine, Phenylalanine, Tryptophan, Norleucine, Isoleucine, or
      a neutral aliphatic amino acid
<220> FEATURE:
<221> NAME/KEY: MISC_FEATURE
<222> LOCATION: (9)..(9)
<223> OTHER INFORMATION: Xaa = Alanine, Valine, Isoleucine, Leucine,
      Methionine, Phenylalanine, Tryptophan, a neutral aliphatic amino
      acid or is absent
<220> FEATURE:
<221> NAME/KEY: MOD_RES
<222> LOCATION: (9)..(9)
<223> OTHER INFORMATION: modified with Hydrogen, NH2, aliphatic amine of
      1 to 10 carbons, isobutylamine, iso-valerylamine, cyclohexamine,
      aromatic amine, arylalkyl amine, tertiary amine, or no residue

<400> SEQUENCE: 43

Xaa Xaa Xaa Xaa Xaa Xaa Xaa Xaa Xaa
1               5

<210> SEQ ID NO 44
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Leucine, Valine, Methionine, Alanine,
      Norleucine, Isoleucine or is absent
<220> FEATURE:
<221> NAME/KEY: MOD_RES
<222> LOCATION: (1)..(1)
<223> OTHER INFORMATION: attachment of a hydrogen, a straight chained or
      branched alkyl group of 1 to 8 carbons, an RCO group, where R is a
      straight or branched alkyl group of 1 to 8 carbons, tertiary
      amine, propianoyl, butanoyl, isopropianoyl, isobutanoyl, or no
      residue
<220> FEATURE:
<221> NAME/KEY: MISC_FEATURE
<222> LOCATION: (2)..(2)
<223> OTHER INFORMATION: Xaa = Proline, Alanine, Aminoisobutyric Acid or
      is absent
<220> FEATURE:
<221> NAME/KEY: MISC_FEATURE
<222> LOCATION: (3)..(3)
<223> OTHER INFORMATION: Xaa = Histidine, Lysine, Alanine, Arginine,
      Ornithine or is absent
<220> FEATURE:
<221> NAME/KEY: MISC_FEATURE
<222> LOCATION: (4)..(4)
<223> OTHER INFORMATION: Xaa = Phenylalanine, Tyrosine, Alanine,
      Tryptophan, Histidine, Norleucine, Isoleucine, an alpha-amino acid
      having a hydrophobic side chain or is absent
<220> FEATURE:
<221> NAME/KEY: MISC_FEATURE
<222> LOCATION: (5)..(5)
```

```
<223> OTHER INFORMATION: Xaa = Threonine, Serine, Valine,
      Hydroxyproline, or a neutral Hydrophilic amino acid
<220> FEATURE:
<221> NAME/KEY: MISC_FEATURE
<222> LOCATION: (6)..(6)
<223> OTHER INFORMATION: Xaa = Isoleucine, Leucine, Valine, Proline,
      Methionine, Hydroxyproline, or an alpha-amino acid having a
      hydrophobic side chain
<220> FEATURE:
<221> NAME/KEY: MISC_FEATURE
<222> LOCATION: (7)..(7)
<223> OTHER INFORMATION: Xaa = Aspartic Acid, Asparagine, Glutamic Acid,
      Glutamine, Serine, or Histidine
<220> FEATURE:
<221> NAME/KEY: MISC_FEATURE
<222> LOCATION: (8)..(8)
<223> OTHER INFORMATION: Xaa = Alanine, Valine, Isoleucine, Leucine,
      Methionine, Phenylalanine, Tryptophan, Norleucine, Isoleucine, or
      a neutral aliphatic amino acid
<220> FEATURE:
<221> NAME/KEY: MISC_FEATURE
<222> LOCATION: (9)..(9)
<223> OTHER INFORMATION: Xaa = Alanine, Valine, Isoleucine, Leucine,
      Methionine, Phenylalanine, Tryptophan, a neutral aliphatic amino
      acid or is absent
<220> FEATURE:
<221> NAME/KEY: MOD_RES
<222> LOCATION: (9)..(9)
<223> OTHER INFORMATION: modified with Hydrogen, NH2, aliphatic amine of
      1 to 10 carbons, isobutylamine, iso-valerylamine, cyclohexamine,
      aromatic amine, arylalkyl amine, tertiary amine, or no residue

<400> SEQUENCE: 44

Xaa Xaa Xaa Xaa Xaa Xaa Xaa Xaa Xaa
1               5

<210> SEQ ID NO 45
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Arg, Lys, Ornithine, or no residue
<220> FEATURE:
<221> NAME/KEY: MOD_RES
<222> LOCATION: (1)..(1)
<223> OTHER INFORMATION: modified by Hydrogen, a straight chained or
      branched alkyl group of 1-8 carbons, an acyl group (RCO-) wherein
      R is straight chained or branched alkyl group of 1-8 carbons, or
      is no residue
<220> FEATURE:
<221> NAME/KEY: MISC_FEATURE
<222> LOCATION: (2)..(2)
<223> OTHER INFORMATION: Xaa = Tyr, Phe, His, Trp, or is no residue
<220> FEATURE:
<221> NAME/KEY: MISC_FEATURE
<222> LOCATION: (3)..(3)
<223> OTHER INFORMATION: Xaa = Thr, Ser, Val, Leu, Pro, Ala or is no
      residue
<220> FEATURE:
<221> NAME/KEY: MISC_FEATURE
<222> LOCATION: (4)..(4)
<223> OTHER INFORMATION: Xaa = Valine, Proline or is no residue
<220> FEATURE:
<221> NAME/KEY: MISC_FEATURE
<222> LOCATION: (5)..(5)
<223> OTHER INFORMATION: Xaa = Alanine, Glutamic Acid, Glutamine,
      Aspartic Acid, Asparagine, Histidine, or is no residue
<220> FEATURE:
<221> NAME/KEY: MISC_FEATURE
<222> LOCATION: (6)..(7)
<223> OTHER INFORMATION: Xaa = Alanine, Valine, Leucine, Phenylalanine,
```

```
            Tryptophan or no residue
<220> FEATURE:
<221> NAME/KEY: MOD_RES
<222> LOCATION: (7)..(7)
<223> OTHER INFORMATION: modified by hydrogen, NH2, aliphatic amine of
      1-10 carbons, an aromatic amine, an arylalkyl amine, or no residue

<400> SEQUENCE: 45

Xaa Xaa Xaa Xaa Xaa Xaa Xaa
1               5

<210> SEQ ID NO 46
<211> LENGTH: 7
<212> TYPE: PRT
<213> ORGANISM: Artificial
<220> FEATURE:
<223> OTHER INFORMATION: Synthetic construt
<220> FEATURE:
<221> NAME/KEY: MISC_FEATURE
<222> LOCATION: (3)..(3)
<223> OTHER INFORMATION: Xaa = beta-hydroxy Valine

<400> SEQUENCE: 46

Arg Tyr Xaa Pro Glu Leu Ala
1               5

<210> SEQ ID NO 47
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = indolizidin-2-one amino acid

<400> SEQUENCE: 47

Arg Tyr Xaa Glu Leu Ala
1               5

<210> SEQ ID NO 48
<211> LENGTH: 6
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = D-Ornithine
<220> FEATURE:
<221> NAME/KEY: MISC_FEATURE
<222> LOCATION: (3)..(3)
<223> OTHER INFORMATION: Xaa = (3R,6R,9R)-indolizidin-2-one amino acid

<400> SEQUENCE: 48

Xaa Tyr Xaa Glu Leu Ala
1               5

<210> SEQ ID NO 49
<211> LENGTH: 5
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (3)..(3)
```

```
<223> OTHER INFORMATION: Xaa = (3R,6R,9R)-indolizidin-2-one amino acid

<400> SEQUENCE: 49

Arg Tyr Xaa Glu Leu
1               5
```